(12) United States Patent
Thapliyal

(10) Patent No.: US 10,575,975 B2
(45) Date of Patent: Mar. 3, 2020

(54) PERSONALIZED PROSTHESIS AND METHODS OF DEPLOYMENT

(71) Applicant: AneuMed, Inc., Los Altos, CA (US)

(72) Inventor: Hira V Thapliyal, Los Altos, CA (US)

(73) Assignee: AneuMed, Inc., Los Altos, CA (US)

( * ) Notice: Subject to any disclaimer, the term of this patent is extended or adjusted under 35 U.S.C. 154(b) by 254 days.

(21) Appl. No.: 15/136,577

(22) Filed: Apr. 22, 2016

(65) Prior Publication Data

US 2016/0310303 A1  Oct. 27, 2016

Related U.S. Application Data

(60) Provisional application No. 62/151,356, filed on Apr. 22, 2015, provisional application No. 62/232,727, (Continued)

(51) Int. Cl.
*A61F 2/966* (2013.01)
*A61F 2/856* (2013.01)
(Continued)

(52) U.S. Cl.
CPC .............. *A61F 2/966* (2013.01); *A61F 2/07* (2013.01); *A61F 2/856* (2013.01); *A61F 2/90* (2013.01);
(Continued)

(58) Field of Classification Search
None
See application file for complete search history.

(56) References Cited

U.S. PATENT DOCUMENTS

| 4,436,684 A | 3/1984 | White |
| 5,116,365 A | 5/1992 | Hillstead |

(Continued)

FOREIGN PATENT DOCUMENTS

| CN | 1336160 A | 2/2002 |
| CN | 1421182 A | 6/2003 |

(Continued)

OTHER PUBLICATIONS

International Search Report dated Sep. 1, 2016 for international application PCT/US2016/029047.
(Continued)

*Primary Examiner* — Martin T Ton
(74) *Attorney, Agent, or Firm* — Schwegman Lundberg & Woessner, P.A.

(57) ABSTRACT

A personalized prosthesis for implantation at a treatment site of a patient includes a self-expanding mesh and/or membrane having collapsed and expanded configurations. The collapsed configuration is adapted to be delivered to the treatment site, and the expanded configuration is oversized relative to the treatment site and configured to engage the personalized prosthesis with the treatment site. The self-expanding mesh is configured to reduce in one or more dimensions in response to being constrained in the one or more dimensions, such that the mesh in the expanded configuration self-adjusts to the treatment site without buckling of the mesh. The self-expanding mesh or membrane forms a central lumen configured to allow blood or other body fluids to flow therethrough. Methods of manufacturing and delivery of the personalized prosthesis are also disclosed.

15 Claims, 63 Drawing Sheets

Related U.S. Application Data filed on Sep. 25, 2015, provisional application No. 62/253,846, filed on Nov. 11, 2015.

(51) Int. Cl.
*A61F 2/90* (2013.01)
*A61F 2/07* (2013.01)
*A61F 2/06* (2013.01)

(52) U.S. Cl.
CPC ... *A61F 2002/061* (2013.01); *A61F 2002/077* (2013.01); *A61F 2002/9665* (2013.01); *A61F 2230/0069* (2013.01); *A61F 2240/002* (2013.01)

(56) References Cited

U.S. PATENT DOCUMENTS

| | | | |
|---|---|---|---|
| 6,165,193 | A | 12/2000 | Greene, Jr. et al. |
| 6,221,100 | B1 | 4/2001 | Strecker |
| 6,264,689 | B1 | 7/2001 | Colgan et al. |
| 6,383,216 | B1 | 5/2002 | Kavteladze et al. |
| 6,395,018 | B1 | 5/2002 | Castaneda |
| 6,500,190 | B2 | 12/2002 | Greene et al. |
| 6,695,833 | B1 | 2/2004 | Frantzen |
| 7,029,487 | B2 | 4/2006 | Greene et al. |
| 7,198,675 | B2 | 4/2007 | Fox et al. |
| 7,201,762 | B2 | 4/2007 | Greene et al. |
| 7,483,558 | B2 | 1/2009 | Greene et al. |
| 7,530,988 | B2 | 5/2009 | Evans et al. |
| 7,666,220 | B2 | 2/2010 | Evans et al. |
| 7,769,603 | B2 | 8/2010 | Jung et al. |
| 7,790,273 | B2 | 9/2010 | Lee et al. |
| 7,799,047 | B2 | 9/2010 | Greene, Jr. et al. |
| 7,951,448 | B2 | 5/2011 | Lee et al. |
| 8,361,137 | B2 | 1/2013 | Perouse |
| 8,870,941 | B2 | 10/2014 | Evans et al. |
| 8,906,084 | B2 | 12/2014 | Evans et al. |
| 8,926,682 | B2 | 1/2015 | Herbowy et al. |
| 8,945,199 | B2 | 2/2015 | Ganpath et al. |
| 9,744,060 | B2 | 8/2017 | Thapliyal |
| 2002/0022875 | A1 | 2/2002 | Strecker |
| 2002/0055771 | A1 | 5/2002 | Sandock |
| 2004/0034403 | A1 | 2/2004 | Schmitt |
| 2004/0079737 | A1 | 4/2004 | Pinchasik |
| 2005/0049667 | A1 | 3/2005 | Arbefeuille et al. |
| 2006/0058638 | A1 | 3/2006 | Boese et al. |
| 2006/0095069 | A1 | 5/2006 | Shah et al. |
| 2007/0043432 | A1 | 2/2007 | Perouse |
| 2007/0100419 | A1 | 5/2007 | Licata et al. |
| 2007/0293936 | A1 | 12/2007 | Dobak, III |
| 2008/0039923 | A1 | 2/2008 | Taylor et al. |
| 2008/0228216 | A1 | 9/2008 | Strauss et al. |
| 2008/0294267 | A1* | 11/2008 | Chanduszko ............ A61F 2/91 623/23.7 |
| 2009/0248131 | A1 | 10/2009 | Greenan |
| 2009/0309273 | A1 | 12/2009 | Parker |
| 2010/0114296 | A1 | 5/2010 | Case et al. |
| 2010/0185270 | A1 | 7/2010 | Ramzipoor et al. |
| 2010/0198333 | A1 | 8/2010 | Macatangay et al. |
| 2010/0274340 | A1 | 10/2010 | Hartley et al. |
| 2011/0016690 | A1 | 1/2011 | Narainasamy et al. |
| 2011/0313503 | A1 | 12/2011 | Berra et al. |
| 2011/0313505 | A1 | 12/2011 | Mchugo |
| 2013/0289690 | A1* | 10/2013 | Thapliyal ............ A61F 2/90 623/1.2 |
| 2014/0343683 | A1* | 11/2014 | Jeon ............ A61F 2/04 623/23.7 |
| 2015/0039083 | A1* | 2/2015 | Rafiee ............ A61F 2/2436 623/2.11 |
| 2015/0073526 | A1 | 3/2015 | Kluck |
| 2015/0100113 | A1 | 4/2015 | Davidson et al. |
| 2015/0374518 | A1 | 12/2015 | Thapliyal |

FOREIGN PATENT DOCUMENTS

| | | |
|---|---|---|
| CN | 1669538 A | 9/2005 |
| CN | 101332133 A | 12/2008 |
| CN | 101972181 A | 2/2011 |
| CN | 104039269 A | 9/2014 |
| EP | 1057459 A1 | 12/2000 |
| EP | 1177779 A2 | 2/2002 |
| EP | 1574169 A2 | 9/2005 |
| EP | 3285687 A1 | 2/2018 |
| FR | 2858208 A1 | 2/2005 |
| JP | 2002035135 A | 2/2002 |
| JP | 2002132934 A | 5/2002 |
| JP | 2005514988 A | 5/2005 |
| JP | 2010528681 A | 8/2010 |
| JP | 2011516156 A | 5/2011 |
| WO | WO-9209246 A1 | 6/1992 |
| WO | WO-2004022150 A1 | 3/2004 |
| WO | WO-2008051941 A2 | 5/2008 |
| WO | WO-2016172629 A1 | 10/2016 |

OTHER PUBLICATIONS

"U.S. Appl. No. 13/663,160, Final Office Action dated Nov. 3, 2014", 11 pgs.
"U.S. Appl. No. 13/663,160, Non Final Office Action dated Jun. 10, 2015", 8 pgs.
"U.S. Appl. No. 13/663,160, Non Final Office Action dated Jun. 13, 2014", 14 pgs.
"U.S. Appl. No. 14/850,586, Non Final Office Action dated Aug. 26, 2016", 13 pgs.
"U.S. Appl. No. 14/850,586, Notice of Allowance dated May 10, 2017", 9 pgs.
"U.S. Appl. No. 14/850,586, Preliminary Amendment filed Jan. 7, 2016", 7 pgs.
"U.S. Appl. No. 14/850,586. Response filed Jan. 23, 2017 to Non Final Office Action dated Aug. 26, 2016", 6 pgs.
"Chinese Application Serial No. 201680023474.5, Office Action mailed", W/ English Translation, 14 pgs.
"Chinese Application Serial No. 201680023474.5, Office Action dated Aug. 27, 2018", w/ English Claims, 13 pgs.
"European Application Serial No. 12845551.6, Extended European Search Report dated Aug. 20, 2015", 7 pgs.
"International Application Serial No. PCT/US2012/062595, International Search Report dated Mar. 8, 2013", 4 pgs.
"International Application Serial No. PCT/US2012/062595, Written Opinion dated Mar. 8, 2013", 7 pgs.
"International Application Serial No. PCT/US2016/029047, International Preliminary Report on Patentability dated Nov. 2, 2017", 8 pgs.
"International Application Serial No. PCT/US2016/029047, Invitation to Pay Additional Fees and Partial Search Report dated Jun. 30, 2016", 3 pgs.
"International Application Serial No. PCT/US2016/029047, Written Opinion dated Sep. 1, 2016", 6 pgs.
"PSI—Patient Specific Implants", Synthes CMF, [Online] Retrieved from the internet: <http://synthes.vo.llnwd.net/o16/LLNWMB8/US%20Mobile/Synthes%20North%20America/Product%20Support%20Materials/Brochures/MXBROPSI-J5245G.pdf>, Retrieved by the examiner on Feb. 26, 2013. (Jul. 11, 2011).
"European Application Serial No. 16784029.7, Extended European Search Report dated Jun. 6, 2019", 8 pgs.
"Chinese Application Serial No. 201680023474.5, Office Action dated Oct. 16, 2019", w/ English translation, 10 pgs.
"European Application Serial No. 16784029.7, Response filed Jan. 2, 2020 to Extended European Search Report dated Jun. 6, 2019", 9 pgs.

* cited by examiner

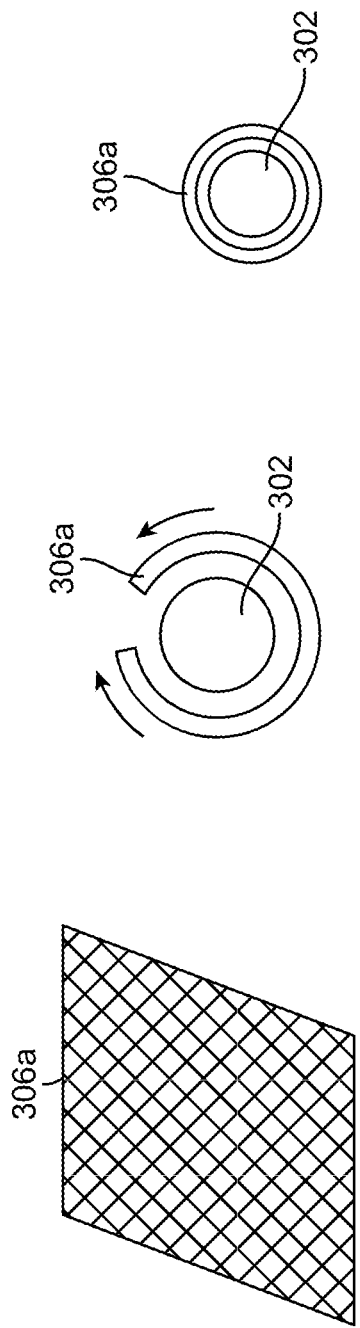

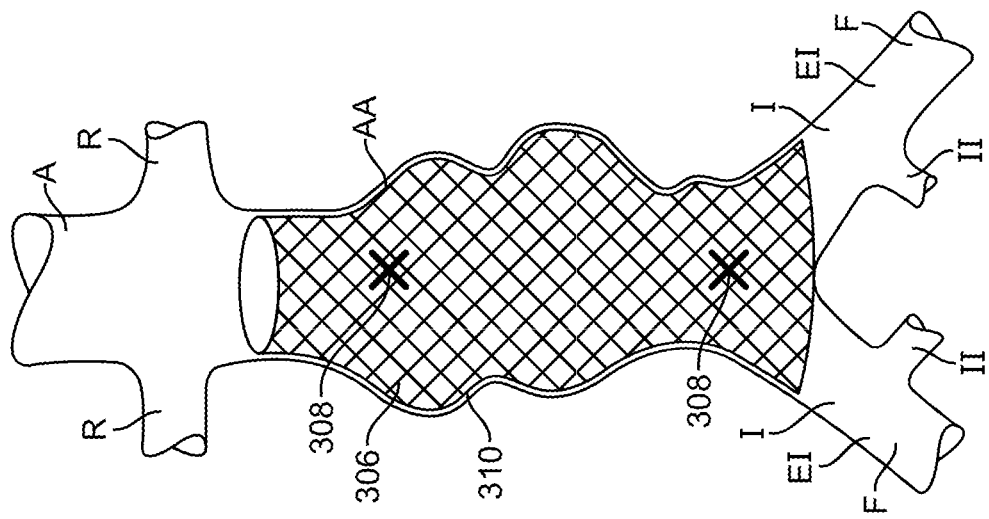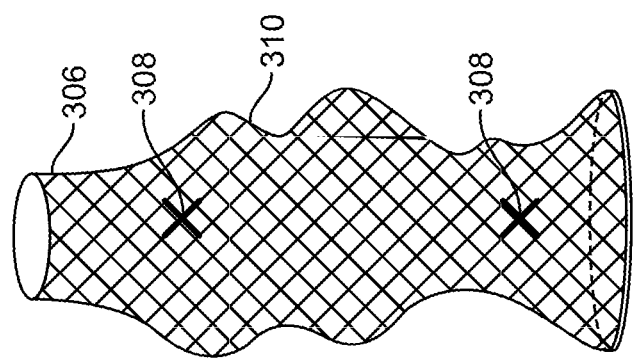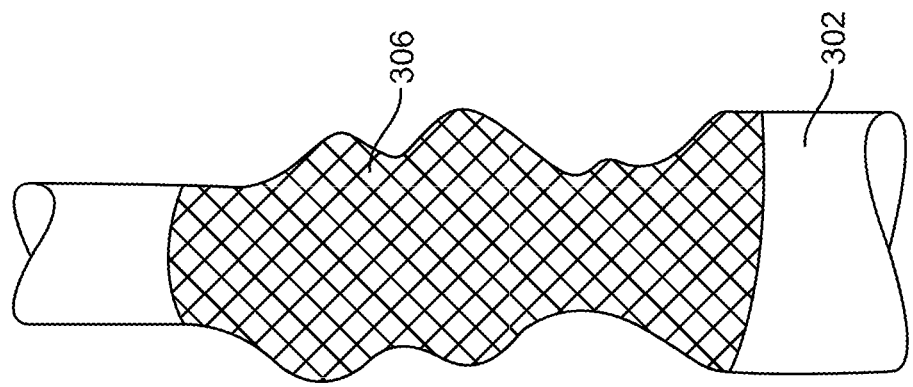

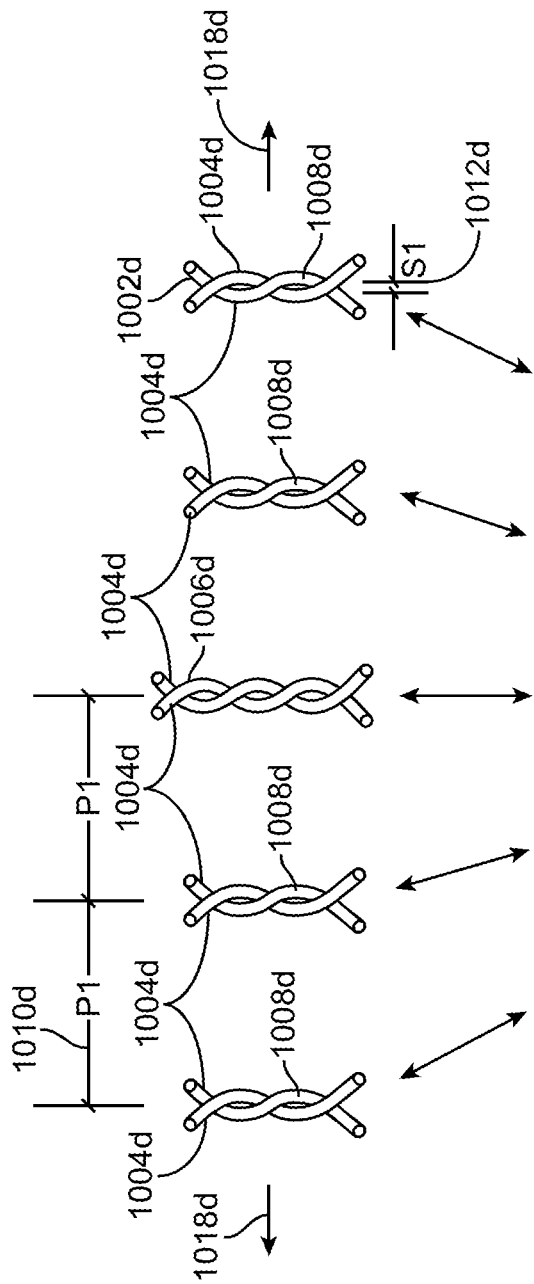
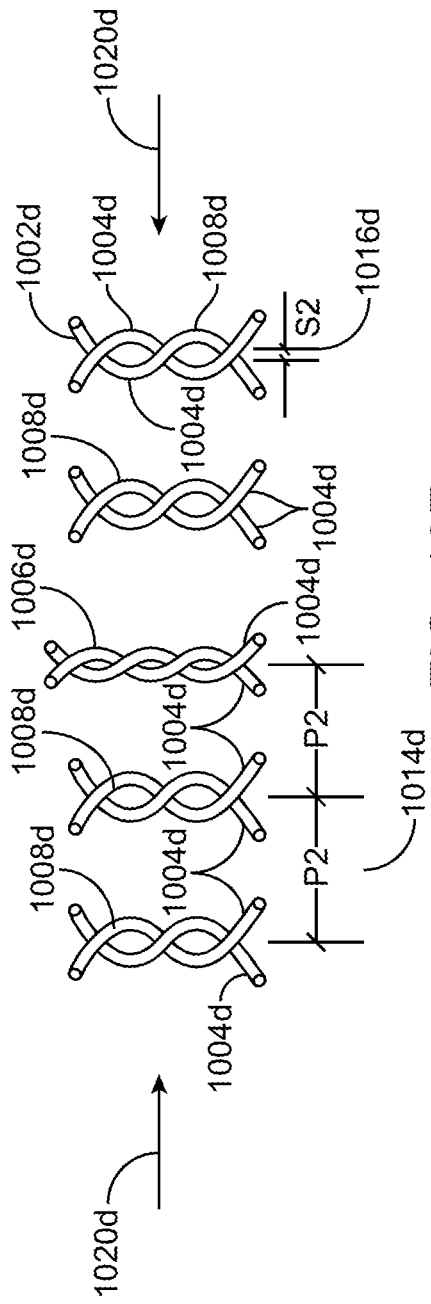
FIG. 12E
FIG. 12F

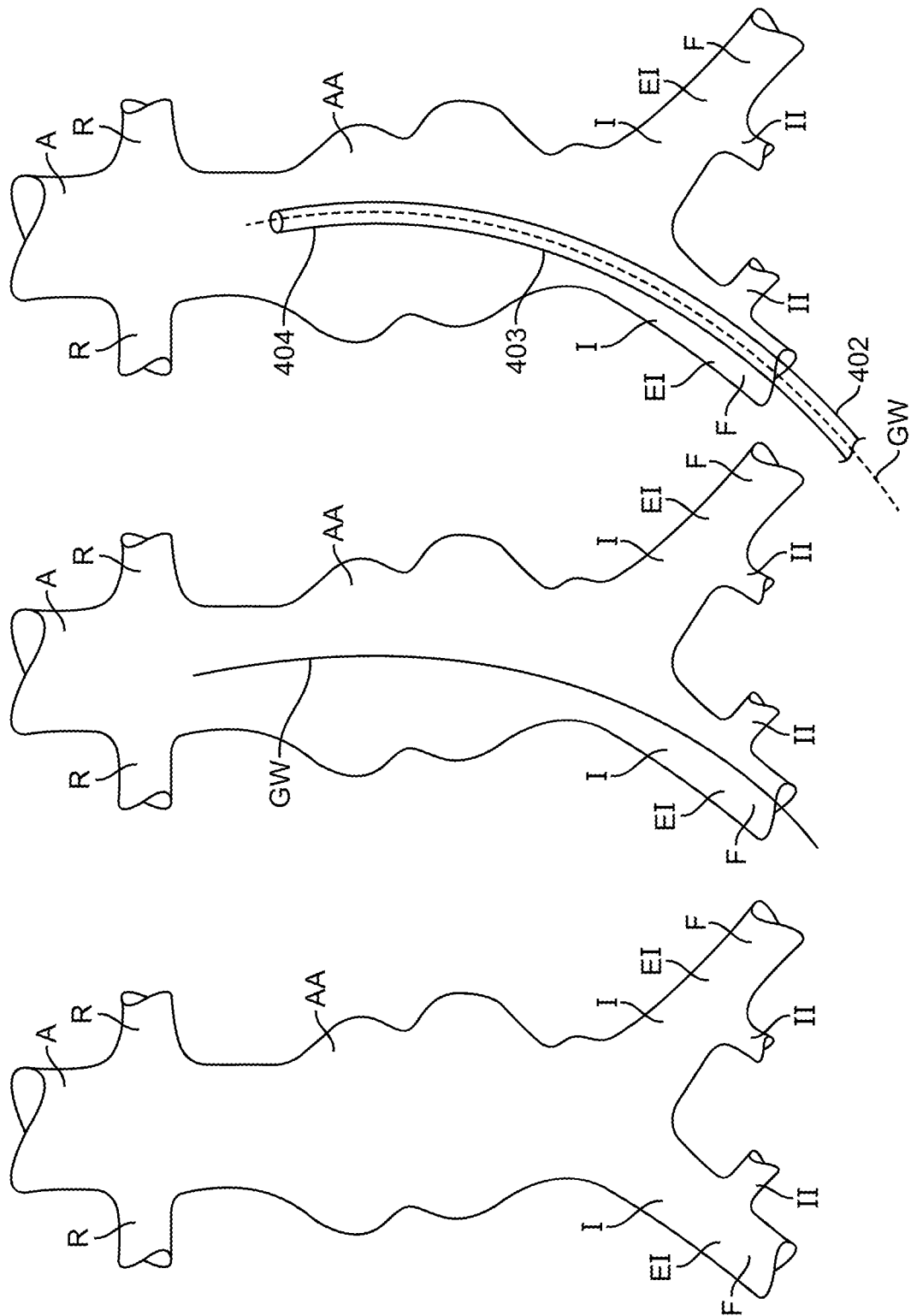

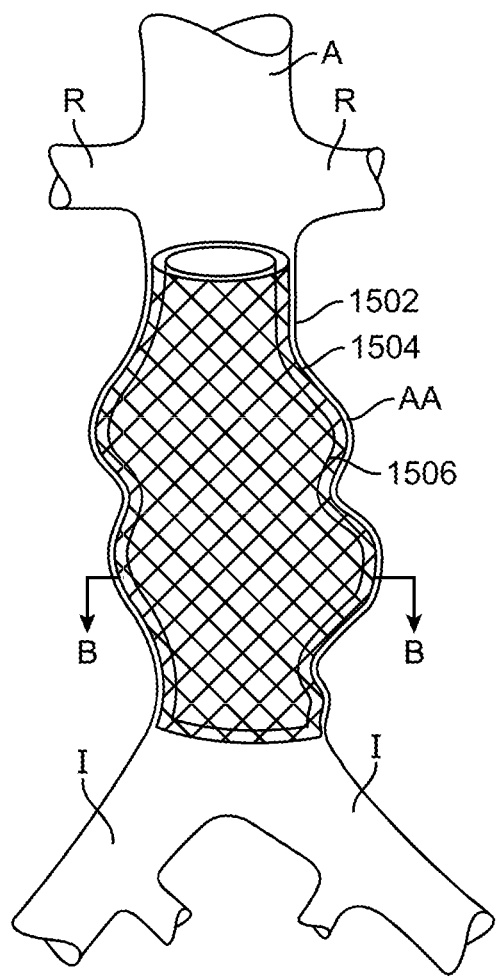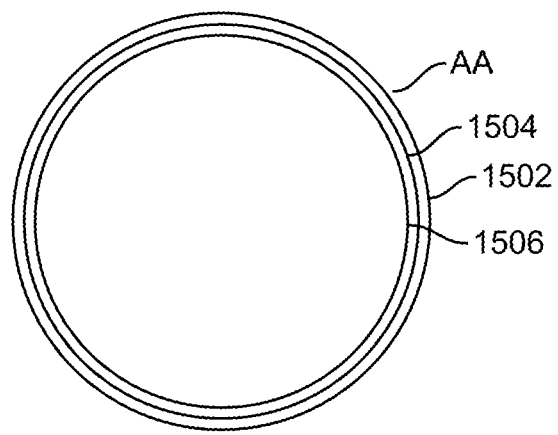
FIG. 34A
VIEW B-B
FIG. 34B

PERSONALIZED PROSTHESIS AND METHODS OF DEPLOYMENT

RELATED APPLICATIONS

The present application is a non-provisional of, and claims the benefit of U.S. Provisional Patent Application No. 62/151,356, filed on Apr. 22, 2015, U.S. Provisional Patent Application No. 62/232,727, filed on Sep. 25, 2015, and U.S. Provisional Patent Application No. 62/253,846, filed on Nov. 11, 2015, the entire contents of which are incorporated herein by reference.

The present application is related to U.S. patent application Ser. No. 14/850,586 filed Sep. 10, 2015; the entire contents of which are incorporated herein by reference.

BACKGROUND OF THE INVENTION

1. Field of the Invention

The present application generally relates to medical prostheses, methods for fabricating the prostheses, and methods for treating diseased or damaged tissue. More specifically, the present application relates to treatment of blood vessels or other body lumens and body cavities, including aneurysms such as in the aorta or in the brain.

An aneurysm is the localized dilation of a blood vessel which presents a serious medical condition. Such distention is the result of localized weakening of the vessel often caused by atherosclerosis, infection, or congenital defects. Most commonly aneurysms occur in arteries at the base of the brain or in the aorta. Cases of significant distention risk the possibility of vessel rupture and the resulting internal hemorrhage is a life threatening medical emergency that requires immediate surgical intervention. Aneurysms that are large enough to present an unacceptable level of risk of rupture are treated with preemptive surgery.

The most reliable surgical remedy for aneurysms is excision of the aneurysm and repair of the afflicted blood vessel with a graft. However, this procedure requires highly invasive surgery and often requires clamping of a major vessel such as the aorta, which can place a large strain on the patient's heart. Patients requiring aneurysm treatment often have co-morbid risk factors such as diabetes, heart disease, and hypertension, and thus such patients can be poor candidates for such a stressful operation. Accordingly, newer endovascular grafting methods for minimally invasive intervention of aneurysms are favored over traditional grafts for some patients. These endovascular installed grafts or "endoluminal grafts" are installed by accessing the aneurysm through the femoral arteries and have stent-like scaffolding supports at its terminal ends. Endoluminal grafts, however, in some situations are more prone to post-operative complications than traditionally installed grafts. Within two years of installation, a significant number of aortic endoluminal grafts exhibit leakage at the proximal interface to the aorta, necessitating further endovascular surgical intervention. Additionally, a small portion of endoluminal grafts drift inside the repaired blood vessel and expose the aneurysm. Repair of a drifted graft requires open surgery in a patient who is likely a poor candidate for such a procedure.

Endoluminal grafting must overcome geometrical problems stemming from morphological variations in aneurysm presentation and location. While most aneurysms are "fusiform," exhibiting distention along the entire circumference of the afflicted blood vessel, varied geometries exist. Some aneurysms display ballooning of the vessel on one side at a narrow neck (also referred to as saccular), or may have otherwise treacherous geometries. Other aneurysms may be located in close proximity to sensitive structures such as renal arteries. Endoluminal grafts in certain situations may encounter higher incidence of failure with non-fusiform geometries and may be unsuitable for implantation where the implants and their delivery techniques prove too incompatible or cumbersome for aneurysm geometry or location.

Since the introduction of the stent graft in 1992, there is a persistent problem of endoleaks. The purpose of the placement of the stent graft is to direct the blood flow through the lumen of the stent graft and isolate the aneurysm sac. Clinical success is determined by the complete exclusion of the sac. However, in more than 20% of the cases, the aneurysm sac is not effectively excluded whereby blood 'leaks' in to the sac. This leak is defined as 'endoleak'. The result is the sac continues to grow due to the persistent pressure of the blood against a weakened blood vessel wall, the risk of the blood vessel wall rupture is not mitigated, and the treatment is deemed to be a failure. Endoleak is a major cause of complication, and the post-operative management of the endoleaks is cumbersome and messy.

There are actually five kinds of endoleaks associated with the currently marketed stent grafts. Type I endoleak refers to the leakage of the blood flow into the sac because of an incomplete seal at the ends of the stent graft. Type II endoleak occurs when blood flows into the sac from the side branches in a retrograde fashion. Type III endoleak is defined when there is an ineffective seal at the joints of two limbs of the stent graft. Type IV endoleak happens in there is a defect, such as porosity in the graft material. Finally, Type V endoleak, known as endotension, is not really a leak, but a persistence of blood pressure in the aneurysm sac which continues to enlarge the sac towards eventual rupture if left untreated.

The most persistent endoleak is Type II where the blood comes into the aneurysm pocket from the side branches. The current therapy is to block the side branches from having any flow outward or inward. Preferred embodiments of the current invention may provide a more effective method of achieving the same.

Given these concerns, there is strong unmet need for improved endoluminal grafts and delivery methods. Such an improved design preferably facilitates more reliable repair of aneurysms over a wider space of geometries and the ability to be delivered with such finesse as to shorten procedure time and expand the number of aneurysms that are treatable endovascularly. It would also be desirable if such improved endoluminal grafts also fit the patient's anatomy more accurately and therefore help prevent endoleaks and more securely anchor the endograft in the aneurysm and prevent drifting. At least some of these objectives will be met by the devices described herein.

2. Description of Background Art

Patents and Publications related to personalizable implants include but are not limited to U.S. Pat. Nos. 8,945,199; 8,926,682; 8,906,084; 8,870,941; 7,951,448; 7,799,047; 7,790,273; 7,769,603; 7,666,220; 7,530,988; 7,483,558; 7,201,762; 7,029,487; 6,695,833; 6,500,190; 6,165,193; 4,436,684; and U.S. Patent Publication Nos. 2011/0016690; 2008/0228216; 2008/0039923; and 2006/0058638.

SUMMARY OF THE INVENTION

The present application generally relates to medical prostheses, structures of the prosthesis and the delivery system, and methods for deploying the prosthesis at the intended site in the body. More specifically, the present application relates to treatment of blood vessels or other body lumens and body cavities, including aneurysms such as in the aorta, other arteries, or arteries in the brain. The techniques disclosed herein generally result in a personalized prosthesis that is designed and manufactured to match the anatomy of the patient's diseased or damaged tissue. The personalized prostheses may be commercially distributed once appropriate regulatory approvals have been obtained (e.g. Food and Drug Administration), and are not necessarily the same as "custom devices" defined in 21 CFR § 812.3(b), which applies to non-commercial distribution of medical devices under certain circumstances, such as compassionate use.

The prostheses disclosed herein, such as mesh alone, membrane covered mesh, or membrane alone may be implanted into a treatment site such as an aneurysm to stabilize the aneurysm and to help prevent it from growing larger. This applies to incipient aneurysms (e.g. untreated early stage aneurysms usually less than 50 mm in diameter) or larger, later stage aneurysms may also be treated using the prostheses described herein.

In one aspect, disclosed herein is a system for treating tissue at a treatment site in a bodily lumen. The system comprises a self-expanding prosthesis having a collapsed configuration and an expanded configuration in which an outer surface of the prosthesis is sized and shaped to match contours of an inner wall of the treatment site. The system further comprises a retractable sheath disposed over and constraining the self-expanding prosthesis in the collapsed configuration. The self-expanding prosthesis and retractable sheath are positioned at the treatment site, and progressive retraction of the sheath allows the prosthesis to progressively self-expand to the expanded configuration from a first end portion of the prosthesis to a second end portion of the prosthesis opposite the first end portion. The prosthesis is further configured to self-orient as the prosthesis is moved axially toward the treatment site so that contours of the outer surface of the prosthesis rotationally align with the contours of the inner wall of the treatment site. The bodily lumen may comprise a blood vessel and the treatment site may comprise an aneurysm in the blood vessel.

The prosthesis may be configured to self-expand or self-orient when the prosthesis is disposed in the treatment site. The prosthesis may be configured to self-expand or self-orient when a portion of the prosthesis extends beyond the treatment site.

The prosthesis may progressively self-expand in the treatment site as the prosthesis is moved toward the treatment site. The prosthesis may progressively self-expand such that the first end portion is fully expanded while the second end portion remains constrained by the sheath.

The system may further comprise one or more actuation elements coupled to a proximal portion or a distal portion of the prosthesis, wherein the one or more actuation elements are configured to push or pull the prosthesis. The one or more actuation elements may comprise one or more wires coupled to the proximal or the distal portion of the prosthesis.

The system may further comprise an expandable member disposed under the prosthesis, the expandable member configured for tacking the prosthesis into the treatment site. The expandable member may comprise an expandable wire basket or a balloon.

The prosthesis may comprise an inner surface and an outer surface, and the inner surface may be substantially smooth, and while the outer surface may be textured. The prosthesis may be formed with one or more filaments twisted with one another to form a directional pattern in the prosthesis.

The prosthesis may be disposed in a twisted configuration in the retractable sheath. The prosthesis may be biased to twist in a pre-determined direction upon self-orientation. The prosthesis may self-orient with sufficient force to overcome static friction between the prosthesis engaged with tissue in the treatment region.

The system may further comprise one or more lateral apertures in the prosthesis, the one or more lateral apertures sized to match one or more ostia along the treatment region. The one or more lateral apertures may align with the one or more ostia after self-orienting of the prosthesis. A location of the one or more lateral apertures may be based on one or more images of the treatment region.

In another aspect, disclosed herein is a method for deploying a prosthesis personalized for a patient in a bodily lumen of the patient. The method comprises advancing the prosthesis in a collapsed configuration through the bodily lumen toward a target region in the bodily lumen. The method further comprises allowing the prosthesis to progressively self-expand from the collapsed configuration to an expanded configuration in which an outer surface of the prosthesis is sized and shaped to match contours of an inner wall of the target region. The method further comprises self-orienting the prosthesis such that contours of the outer surface of the prosthesis rotationally align with the contours of the inner wall.

Advancing the prosthesis may comprise advancing the prosthesis so that a portion of the prosthesis extends beyond the target region. Allowing the prosthesis to progressively self-expand may comprise removing a sheath from the prosthesis. Allowing the prosthesis to progressively self-expand may comprise self-expanding from a far end portion to a near end portion of the prosthesis. The far end portion may be further from an operator of prosthesis than the near end portion.

Self-orienting may comprise moving the prosthesis toward the target region. Moving the prosthesis toward the target region may concurrently remove a constraint from the prosthesis, the constraint provided by the target region. Self-orienting may comprise self-rotating of the prosthesis about a longitudinal axis of the bodily lumen and rotationally aligning contours of the outer surface of the prosthesis with the contours of the target region.

Self-orienting may comprise urging the prosthesis to self-orient with the target region due to mismatching between contours of the expanded outer surface of the prosthesis and contours of the inner wall in contact with the expanded outer surface. Release of potential energy from the mismatching into a lower energy state may urge the prosthesis to self-orient and conform with the target region.

The bodily lumen may comprise a blood vessel and the target region may comprise an aneurysm in the blood vessel. A far end portion of the prosthesis may be closer to a heart of the patient than a near end portion of the prosthesis.

The method may further comprise translating or rotating the prosthesis to facilitate the self-orientation of the prosthesis. The translating may comprise pulling a far end or a near end of the prosthesis. Translating or rotating the prosthesis may overcome static friction between a surface of the prosthesis and a surface of the target.

The prosthesis may further comprise a polymeric coating covering the self-expanding wire mesh. The prosthesis may have a central lumen for fluid flow therethrough.

Self-orienting may comprise aligning one or more ostia in the bodily lumen of the target region with one or more lateral apertures in the prosthesis that are sized to match the one or more ostia. A location of the one or more lateral apertures may be based on one or more images of the target region.

The method may further comprise visualizing the prosthesis as the prosthesis is advanced or allowed to progressively self-expand. The method may further comprise tacking the prosthesis into the target with an expandable member. The method may further comprise loading the prosthesis onto a delivery catheter, wherein the prosthesis is loaded in a twisted configuration onto the delivery catheter.

In another aspect, a personalized prosthesis for implantation at a treatment site comprises a self-expanding mesh having a collapsed configuration and an expanded configuration, wherein the collapsed configuration is adapted to be delivered to the treatment site, and wherein the expanded configuration is adapted to expand the personalized prosthesis into engagement with the treatment site. The mesh in the expanded configuration may be personalized to match the treatment site, the mesh having an outer surface that substantially matches the treatment site shape. The self-expanding mesh may form a central lumen configured to allow blood or other body fluids to pass therethrough. The mesh may be configured to be reduced in size in one or more dimensions in response to being constrained in the one or more dimensions.

The mesh may be formed from a plurality of twisted wires, the twisted wires having a pattern comprising a first twist with a first number of loops and an adjacent second twist with a second number of loops, the second number of loops different from the first number of loops. The first twist can allow movement of wires in the loop relative to one another and the second twist can constrain movement of wires in the loop relative to one another. Thereby, the mesh in the expanded configuration can self-adjust to conform to the treatment site without buckling of the mesh. The first twist may comprise two loops and the second twist may comprise three loops, wherein the wires in the first twist move relative to one another to at least partially open one or more of the two loops in response to the mesh in the expanded configuration being constrained within the treatment site.

The pattern of the twisted wires may comprise repeating sub-patterns each comprising three of the first twists adjacent to one of the second twists. The pattern of the twisted wires may comprise repeating sub-patterns each comprising two of the first twists adjacent to one of the second twists.

The self-expanding mesh may comprise one or more filaments woven together to form a first overlapping region and a second overlapping region. In the first overlapping region the filaments may overlap with one another a first number of times, and in the second overlapping region the filaments may overlap with one another a second number of times different than the first number of times. The self-expanding mesh may comprise barbs or hooks adapted to engage tissue at the treatment site and anchor the personalized prosthesis to the treatment site. The self-expanding mesh may comprise a plurality of overlapping filaments forming overlapping regions, wherein the overlapping regions may form raised surfaces adapted to engage tissue at the treatment site and anchor the prosthesis.

The personalized prosthesis may further comprise a membrane coupled to the mesh, wherein the membrane is elastic and conforms to the self-expanding mesh. The membrane may have an outer surface that substantially matches the treatment site shape in the expanded configuration, and the membrane may form the central lumen. The membrane may comprise a resilient polymer impermeable to blood. The membrane may comprise an elongated neck portion, wherein invagination of the elongated neck into the personalized prosthesis forms the central lumen.

The personalized prosthesis may further comprise one or more radiopaque markers coupled to the membrane or the self-expanding mesh for facilitating implantation of the prosthesis at the treatment site.

The personalized prosthesis may further comprise one or more apertures extending through a sidewall of the prosthesis. The one or more apertures may be fluidly coupled with the central lumen to allow blood flow or other fluids to flow between the central lumen and the one or more apertures. The one or more apertures may be configured to accommodate side branch vessels or other body passages such that the prosthesis does not obstruct blood flow or fluid flow therethrough. A location of the one or more apertures may be based on one or more images of the treatment site.

The lumen may not substantially alter blood flow path across the treatment site. The lumen may have a cylindrical shape. The cylindrically shaped lumen may be formed from an invaginated portion of the personalized prosthesis. The outer surface of the self-expanding mesh may be textured and while an inner surface of the self-expanding mesh forming the central lumen may be smooth. The personalized prosthesis may further comprise a smooth lining disposed over an inner surface of the self-expanding mesh.

The self-expanding mesh in the expanded configuration may be oversized relative to a size of the aneurysm. The self-expanding mesh in the expanded configuration may be undersized relative to a size of the aneurysm. The self-expanding mesh in the expanded configuration may be sized to match a size of the aneurysm.

In another aspect, a personalized prosthesis for treating an aneurysm having a lumen extending therethrough comprises a wire mesh having a collapsed configuration and an expanded configuration, wherein the collapsed configuration is adapted to be delivered percutaneously to the aneurysm, and wherein the expanded configuration is configured to conform with the lumen. The wire mesh may be formed from a plurality of twisted wires, the twisted wires having a pattern comprising a first twist with a first number of loops and an adjacent second twist with a second number of loops, the second number of loops different than the first number of loops. The first twist may allow movement of wires in the loop relative to one another and the second twist may constrain movement of wires in the loop relative to one another, thereby allowing the self-adjustment of the oversized wire mesh to conform to the lumen without buckling of the wire mesh.

In another aspect, a method for treating tissue at a treatment site comprises providing an implantable prosthesis having a central lumen, an expanded configuration and a collapsed configuration. The implantable prosthesis may be biased to expand into the expanded configuration, and the implantable prosthesis may be personalized to match a shape of the treatment site. The central lumen may be configured to allow blood flow or other body fluids to pass therethrough. The method further comprises advancing the implantable prosthesis in the collapsed configuration to the treatment site. The method further comprises self-expanding the implantable prosthesis into the expanded configuration, wherein in the expanded configuration the implantable prosthesis has a shape that substantially matches the shape of the treatment site such that the implantable prosthesis expands substantially into engagement with tissue at the treatment site. The method further comprises self-adjusting one or more dimensions of the implantable prosthesis in the expanded configuration such that a size of the expanded implantable prosthesis matches a size of the treatment site. The method further comprises reinforcing the tissue with the implantable prosthesis.

The implantable prosthesis may comprise a wire mesh, and self-adjusting one or more dimensions of the implantable prosthesis may comprise constraining at least some wires in the wire mesh from moving away from one another in a first twisted region and allowing at least some wires in the wire mesh to move away from one another in a second twisted region different than the first twisted region, thereby self-adjusting the wire mesh to the treatment site.

The implantable prosthesis may comprise a self-expanding wire mesh surrounded by a resilient polymer cover. The lumen may have a cylindrical shape. The lumen may be formed from an invaginated portion of the implantable prosthesis. The cylindrically shaped lumen may be disposed inside the implantable prosthesis. The lumen may not substantially alter blood flow path across the treatment site.

Advancing the implantable prosthesis may comprise advancing the implantable prosthesis through a blood vessel. Radially expanding the implantable prosthesis may comprise retracting a sheath away from the implantable prosthesis, thereby allowing the implantable prosthesis to self-expand into the expanded configuration. Reinforcing the tissue may comprise anchoring the implantable prosthesis to the tissue.

The treatment site may comprise an aneurysm, and reinforcing the tissue may comprise preventing the aneurysm from enlarging. The treatment site may comprise an aneurysm and reinforcing the tissue may comprise excluding the aneurysm. Reinforcing the tissue may comprise anchoring the implantable prosthesis with the tissue. The anchoring the implantable prosthesis may comprise engaging barbs on the implantable prosthesis with the tissue. Reinforcing may comprise constraining the tissue from moving radially outward or radially inward.

The implantable prosthesis may comprise one or more radiopaque markers, and the method may further comprise aligning the one or more radiopaque markers with one or more anatomical features at the treatment site.

The implantable prosthesis may comprise one or more apertures in a sidewall thereof, and the method may further comprise aligning the one or more apertures with one or more ostia of side branch vessels or body passages at the treatment site, thereby preventing obstruction of the one or more side branch vessels or the body passages. A location of the one or more apertures may be based on one or more images of the treatment site.

The method may further comprise sealing the implantable prosthesis against the tissue at the treatment site to prevent blood flow therepast. The method may further comprise obstructing fluid flow through a side branch vessel in the treatment site by apposing the implantable prosthesis against an ostium of the side branch vessel.

The implantable prosthesis may be oversized or undersized relative to a size of the treatment site. The implantable prosthesis may be sized to match a size of the treatment site.

In another aspect, disclosed herein is a method for manufacturing a personalized implantable prosthesis in a manufacturing facility. The method comprises providing one or more images of a treatment site in a patient, creating a digital data set characterizing shape and volume of the treatment site based on the one or more images, and transforming the digital data set into machining instructions. The method further comprises forming a mandrel using the machining instructions, wherein the mandrel has a shape that substantially matches the treatment site shape. The method further comprises applying a mesh to the mandrel, the mesh configured to be reduced in size in one or more dimensions in response to being constrained in the one or more dimensions. The method further comprises heat treating the mesh while the mesh is disposed over the mandrel so that the mesh is biased to return to a shape substantially matching the shape of the treatment site. Thereby the personalized implantable prosthesis is formed, the personalized implantable prosthesis having a collapsed configuration and an expanded configuration. The personalized implantable prosthesis may be adapted to be delivered to the treatment site in the collapsed configuration, and the personalized implantable prosthesis may be biased to return to the expanded configuration having the shape substantially matching the treatment site shape.

The mesh may comprise a first twisted region of wires that are adapted to move relative to one another and a second twisted region of wires that are unable to move relative to one another, such that movement of the wires in the first twisted region of wires allow the reduction in size in the one or more dimensions of the mesh. The personalized implantable prosthesis may be oversized or undersized relative to the treatment site. The personalized implantable prosthesis may be exactly sized to match the treatment site. A diameter of the mandrel may be oversized relative to the treatment site by about 2% to about 40% of a corresponding diameter of the treatment site. The diameter of the mandrel is oversized relative to the treatment site by about 5% to about 15% of a corresponding diameter of the treatment site.

Providing the one or more images may comprise providing one or more computerized tomography (CT) images, one or more magnetic resonance images (MRI), one or more x-ray images, one or more ultrasound images, or one or more an angiography images of the treatment site. Transforming the digital data set into machining instructions may comprise transferring the digital data set into a CAD/CAM system. Forming the mandrel may comprise machining a piece of stock or 3-D printing the mandrel.

Applying the mesh to the mandrel may comprise slidably disposing the mesh over the mandrel. Applying the mesh to the mandrel may comprise wrapping a filament around the mesh and the mandrel. Applying the mesh to the mandrel may comprise wrapping a preformed flat mesh therearound.

The method may further comprise forming at least one side aperture in the personalized implantable prosthesis, the at least one side aperture configured to be aligned with a side branch vessel in the treatment site. Forming the at least one side aperture may comprise locating the at least one side aperture based on the digital data set created from the one or more images.

The method may further comprise forming a membrane coupled to the mesh. Forming the membrane may comprise attaching a polymer cover to the mesh. Forming the membrane may comprise dip coating a polymer cover onto the mesh.

The method may further comprise mounting the implantable prosthesis onto a delivery catheter, cleaning the prosthesis and delivery catheter, packaging the implantable prosthesis, and terminally sterilizing the implantable prosthesis.

The method may further comprise requesting verification that the shape of the personalized implantable prosthesis is appropriate for implantation at the treatment site before shipping the personalized implantable prosthesis from the manufacturing facility. The verification may be performed by a physician. The verification may be performed over the Internet or via the cloud. The method may further comprise shipping the personalized implantable prosthesis to a hospital.

The method may further comprise mounting the personalized implantable prosthesis on a delivery catheter, placing the personalized implantable prosthesis and the delivery catheter in packaging, sterilizing the personalized implantable prosthesis and the delivery catheter in the packaging, and requesting verification that the personalized implantable prosthesis is appropriate for implantation at the treatment site before opening the sterile packaging. The verification may be performed by a physician. The verification may be performed over the Internet or via the cloud.

The method may further comprise removing the implantable prosthesis from the mandrel so that a central lumen extends through the implantable prosthesis. The treatment site may be an aneurysm.

In another aspect, disclosed herein is a method for manufacturing a personalized prosthesis for treating an aneurysm. The method comprises forming a mandrel matching a shape of the aneurysm, and disposing a wire mesh over the mandrel. The wire mesh has a first twisted region of wires that are adapted to be movable relative to one another and a second twisted region of wires that are unable to move relative to one another. The method further comprises setting a shape of the wire mesh.

The mandrel may be oversized or undersized relative to the shape of the aneurysm. The mandrel may be sized to match the shape of the aneurysm. The mandrel may be 2%-40% oversized relative to the aneurysm. The mandrel may be 5%-15% oversized relative to the aneurysm. The mandrel may have a size that matches the aneurysm.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5A-5H illustrate exemplary methods of fabricating a personal prosthesis for treatment of an aneurysm.

FIG. 5I illustrates the prosthesis fabricated in FIGS. 3A-3H deployed in an aneurysm.

FIGS. 12A-12H illustrate exemplary mesh patterns.

FIGS. 33A-33F illustrate an exemplary method of delivering a personal prosthesis to a treatment site.

FIGS. 34A-34B illustrate an exemplary use of multiple prostheses.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

The present invention will be described in relation to an abdominal aortic aneurysm. However, one of skill in the art will appreciate that this is not intended to be limiting, and the devices and methods disclosed herein may be used in aneurysms in other parts of the body such as in the brain, as well as used to treat other hollow anatomical structures including ducts, vessels, organs, or any other part of the body where there is a need to reinforce a lumen, channel or other body space. For example, a personalized prosthesis may be fabricated using the techniques described herein for implantation in or around the bladder in order to treat incontinence, or the prosthesis may be personalized to treat a diseased or damaged pyloric valve in the stomach, or other body passages such as a biliary duct.

TERMINOLOGY

In this description the terms 'distal' and 'proximal' are used to denote the location of a certain aspect in the structure of the prosthesis or the delivery catheter system. In the parlance commonly used in catheter art, the term 'proximal' refers to a location closer to the user (e.g. the physician). Conversely, the term 'distal' is used to describe locations which are farther away from the user. For example, the tip of the catheter would be 'distal' to the handle of the catheter. Generally, the parts of the catheter outside the body during use are proximal to the parts which are inside the body. Incidentally, this terminology of 'distal' and 'proximal' is also used in anatomical reference to describe various locations of the body. Here, 'proximal' refers to the locations closer to the heart, and 'distal' refers to the locations farther away from the heart. Thus, for example, the knee is distal to the abdomen of the patient.

These two notions of the same terms can be at conflict at times and prone to creating confusion. For this disclosure, we will use the terms 'distal' and 'proximal' from the point of view of the user and not in the anatomical sense. The anatomical aspects, as they pertain to the treatment of the aortic aneurysms, will use the terms 'superior' and 'inferior' or equivalents which have standard meaning in the art.

Figure 1A:
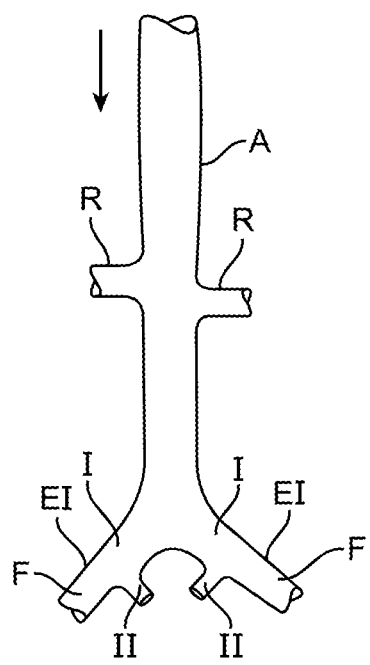
FIG. 1A illustrates a normal abdominal aorta.

In addition, the following abbreviations are used in this specification:

AAA—Abdominal aortic aneurysm
RA—Renal arteries
PSG—Personalized stent graft
DC—Delivery catheter
SB—Side branch blood vessel originating at the site of the AAA
EVAR—Endovascular aneurysm repair FIG. 1A illustrates typical anatomy in a normal section of the abdominal aorta A where blood flows downstream as indicated by the arrow from the heart toward the legs. The aorta is typically a gradually tapering cylinder. A pair of renal arteries R branch off laterally from the aorta A and provide blood to the kidneys (not shown). The aorta bifurcates into two common iliac arteries I which then further bifurcate into the external iliac artery EI and the internal iliac artery II. After the external iliac arteries EI pass the inguinal ligament (not shown) they are then generally referred to as the femoral arteries F. Thus, the aorta provides for smooth blood flow from the heart to the lower extremities of the body.

Figure 1B:
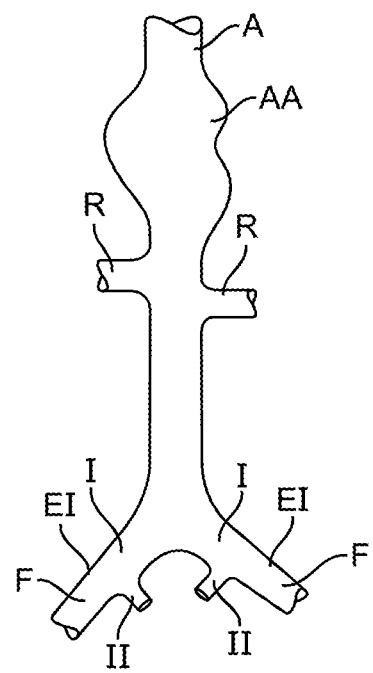
FIGS. 1B-1D illustrate various abdominal aortic aneurysms.
Figure 1C:
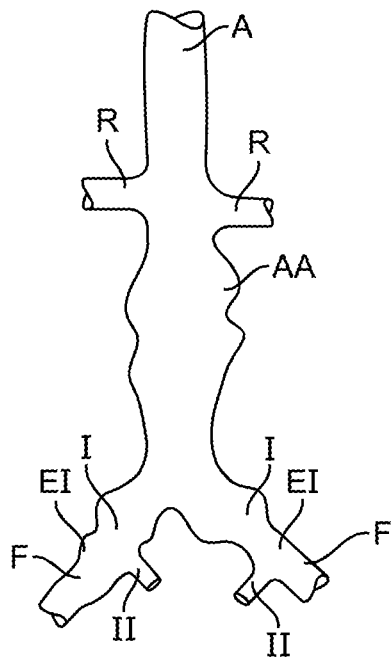
Figure 1D:
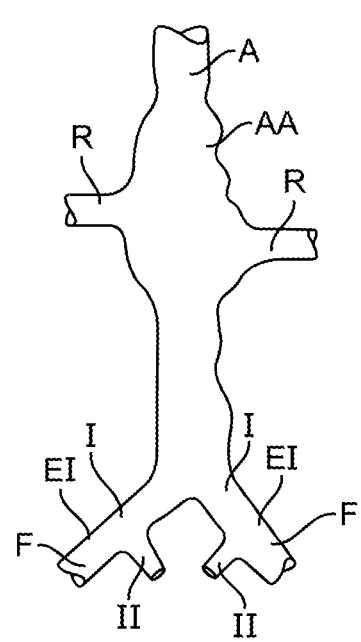
Figure 1E:
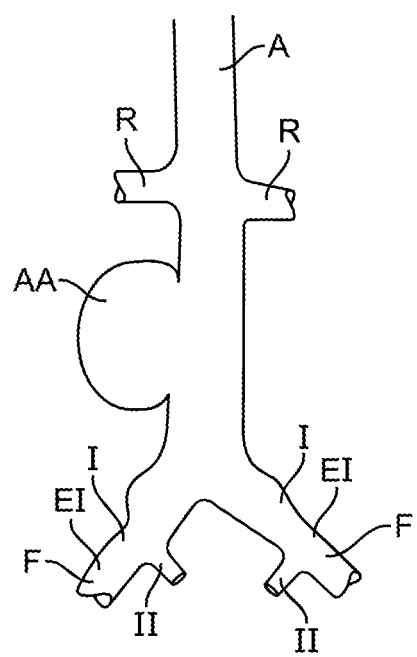
FIG. 1E illustrates a saccular aneurysm.
Figure 1F:
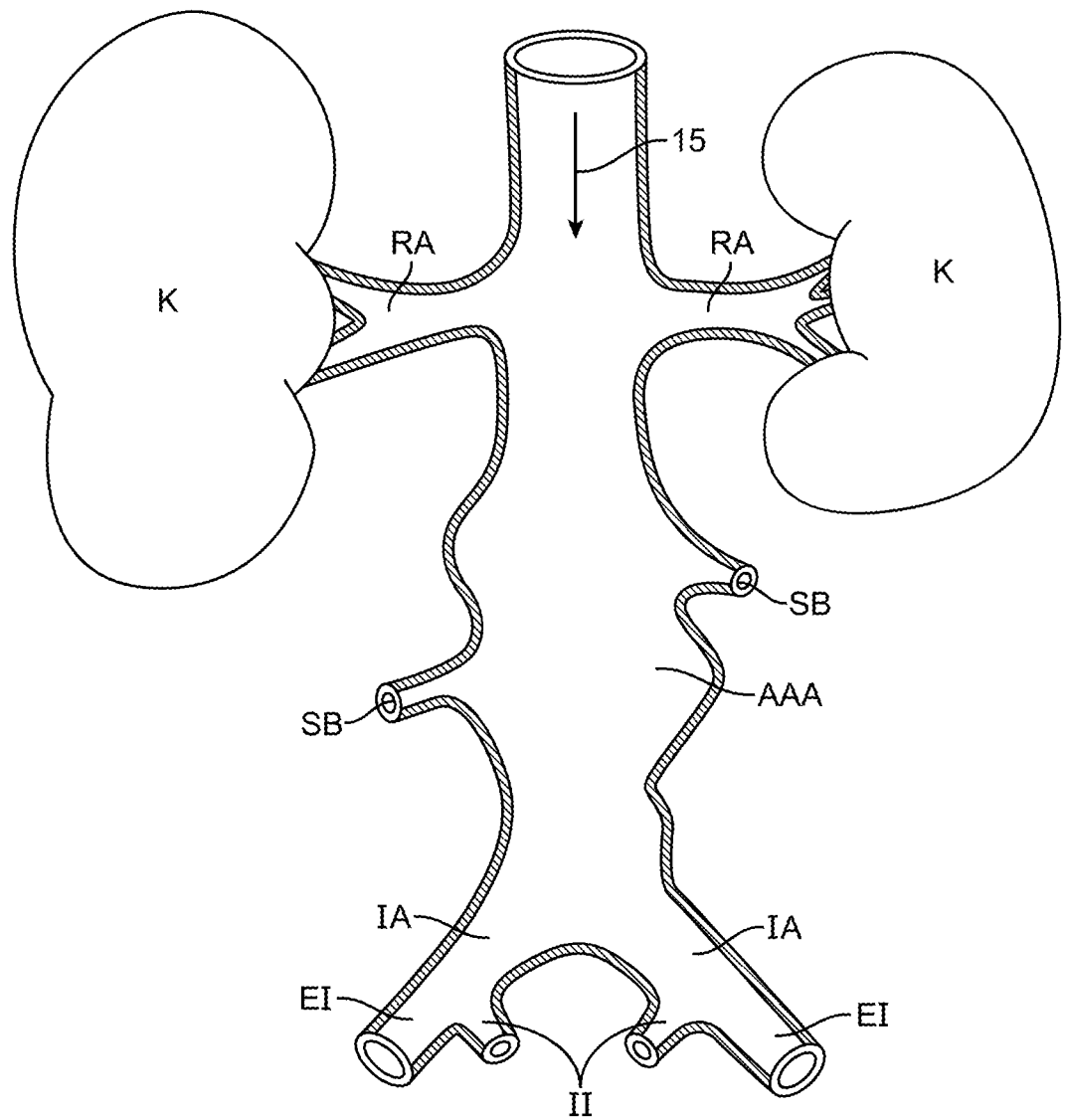
FIG. 1F illustrates an abdominal aortic aneurysm (AAA).

However, in some cases, the tissue in the aorta may become weakened due to disease or damage thereby resulting in a bulged region known as an aneurysm. The aneurysm may be at any point along the abdominal aorta. For example, FIG. 1B illustrates a suprarenal aortic aneurysm where the aneurysm AA is superior to (or upstream or above) the renal arteries R. FIG. 1C illustrates an infrarenal aneurysm AA which is inferior to (or downstream or just below) the renal arteries and this type of aneurysm represents the majority of abdominal aortic aneurysms. FIG. 1C also illustrates that the aneurysm does not always remain strictly in the aorta, and that the aneurysm may extend into the iliac arteries and femoral arteries. FIG. 1D illustrates a juxtarenal aortic aneurysm AA where the aneurysm extends over the portion of the aorta from which the renal arteries branch off. Each of the aneurysms illustrated in FIGS. 1B-1D are referred to as fusiform aneurysms in which the weakened aorta and resulting bulge extend essentially all the way around the vessel. However, aneurysms may also be saccular in which only a portion of the vessel wall bulges outward, such as in FIG. 1E. FIG. 1F illustrates the typical anatomy of the abdominal aortic aneurysm (AAA). The blood flows downstream as indicated by the arrow 15 from the heart toward the legs. A pair of renal arteries RA branch off laterally from the aorta A and provide blood to the kidneys K. The AAA may also have one or more side branches SB which supply blood to the neighboring tissues.

Figure 1G:
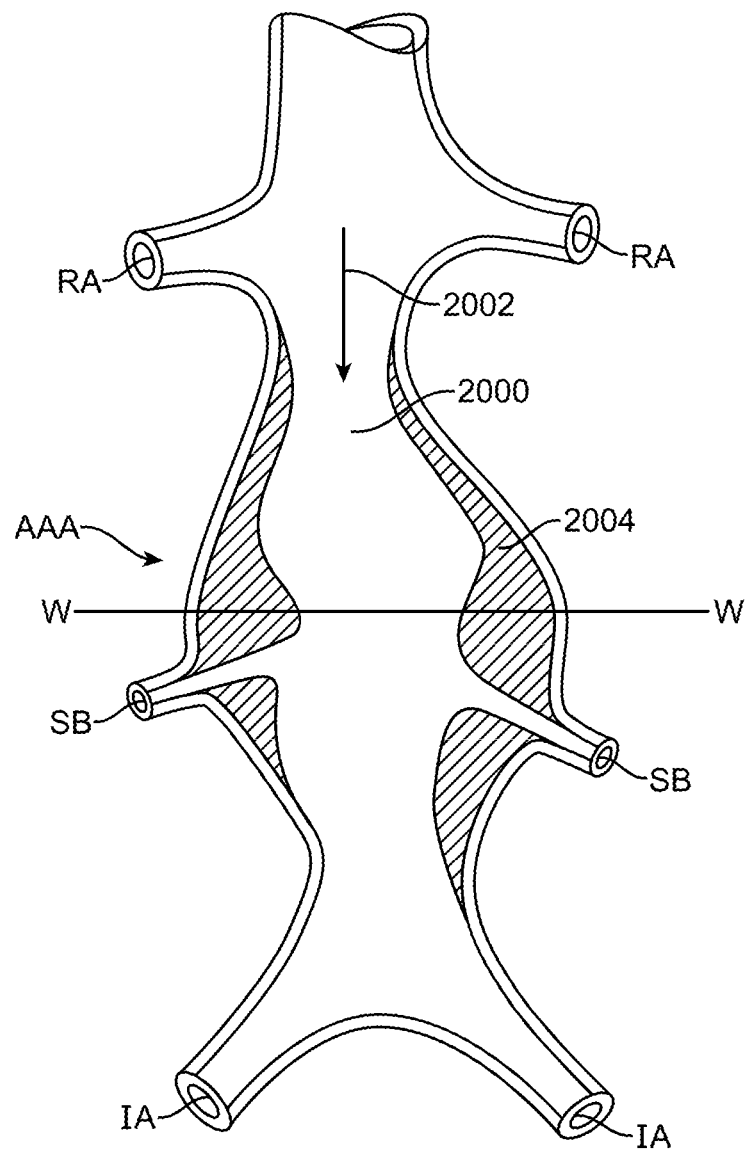
FIG. 1G shows a fusiform aneurysm in the infrarenal abdominal aorta.

FIG. 1G shows an AAA, or a typical fusiform aneurysm of the infrarenal abdominal aorta, with a mural thrombus. The heart supplies blood to the abdomen and lower parts of the body through the lumen 2000. The aortic aneurysm AAA is essentially a bulge in the otherwise cylindrical tubular blood vessel. This bulge is created as the wall of the blood vessel weakens over time and the pressure of the blood pushes the wall outward. The blood flow 2002 typically becomes turbulent giving rise to the formation of mural thrombus 2004.

Figure 1H:
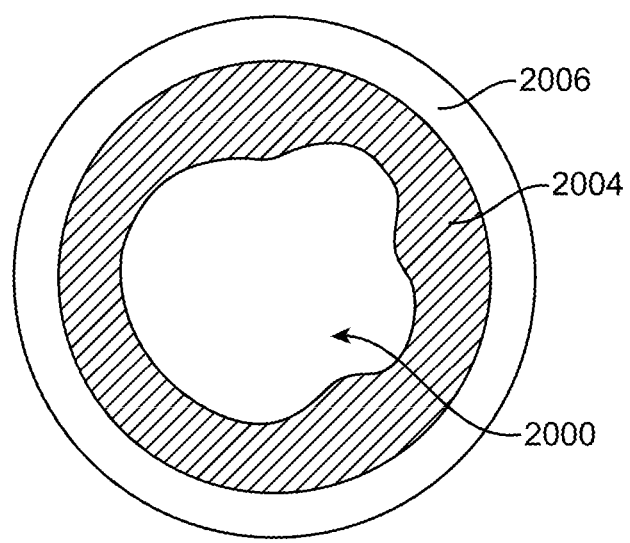
FIG. 1H shows a cross-section along line WW.

FIG. 1H shows the cross section of the aorta through WW of FIG. 1G. Vessel wall 2006 contains the mural thrombus 2004 leaving a narrowed lumen 2000 for the blood to flow therethrough. Typically, a patient goes through a CT scan and the aortic aneurysm AAA is diagnosed. The CT scan shows the blood volume of the lumen, and it does not show the blood vessel wall or the outer surface of the aorta.

Standard surgical procedures for aneurysm repair often use a natural graft or an artificial graft typically made of Dacron™ polyester or expanded polytetrafluorinated ethylene (ePTFE) to replace the damaged or diseased section of the vessel. This procedure is highly invasive, can result in a number of post-operative complications, and requires a lengthy recovery period.

Figure 2:
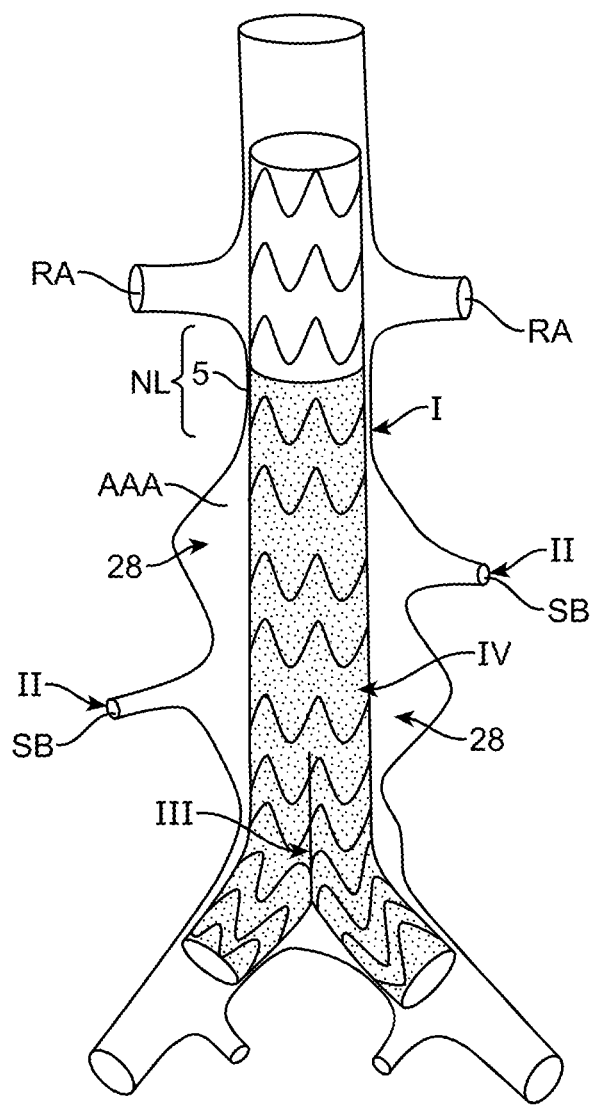
FIG. 2 illustrates the conventional stent graft installed in the AAA and the various types of endoleaks.

More recently, minimally invasive endovascular repair techniques have been developed in which a stent-graft is delivered to the treatment site. FIG. 2 shows a stent graft 5 inserted into the AAA site in a minimally invasive procedure EVAR (endovascular aneurysm repair). The stent-graft, which is substantially cylindrical in shape, is then radially expanded into the aneurysm thereby forming a new lumen for blood flow that excludes the aneurysm. While stent-grafts are promising, the implanted device may obstruct blood flow to side branch vessels SB, or the implant may be pushed downstream away from the treatment site due to the force of the blood and its pulsating nature. This is sometimes referred to as "windsocking."

Additionally, stent-grafts do not always seal perfectly against the vessel wall, thereby allowing blood to continue to pressurize the aneurysm sac 28. Endoleaks are a major cause of failure in the treatment of aneurysms with stent-grafts. Endoleaks have been classified into several categories shown in FIG. 2 as I, II, III, and IV. In Type I endoleaks, blood flows into the aneurysm sac due to incomplete sealing at the proximal end of the stent-graft. The proximal end as used herein with respect to the prosthesis is the end closest to the heart, and the distal end of the prosthesis is the downstream end. When referring to a delivery system used to deliver a prosthesis, the proximal end of the delivery system is the end that is furthest away from the heart and usually closest to the operator, and the distal end is the closest to the heart and typically furthest away from the operator. Type II endoleaks result when blood flows into the aneurysm sac from collateral vessels, such as side branch vessels SB. Type III endoleaks result in blood flow into the aneurysm sac due to poor sealing between stent-graft joints or rupture of the stent-graft. Type IV endoleaks result in blood flow into the aneurysm sac due to excessive or unwanted porosity in the stent-graft that permits blood to flow through the stent-graft into the aneurysm. Endoleaks may result from improper fitting or matching of the stent-graft to the patient's anatomy.

Thus it is clear that there is a need for a prosthesis that can be used to treat aneurysms that has more conformal anchoring to prevent windsocking, and that fits the aneurysm anatomy more accurately in order to minimize the possibility of endoleaks. In some cases, it may be advantageous for the prosthesis to maintain blood flow to side branch vessels. A personalized prosthesis as disclosed herein will address at least some of these issues. Current imaging systems can be linked with computer aided design (CAD) and computer aided manufacturing (CAM) systems to allow a prosthesis to be fabricated that matches the patient's anatomy. Such a personalized prosthesis may also be used to treat normal or presymptomatic tissue of a patient at risk of developing an aneurysm or at early stages of development of an aneurysm.

Figure 3A:
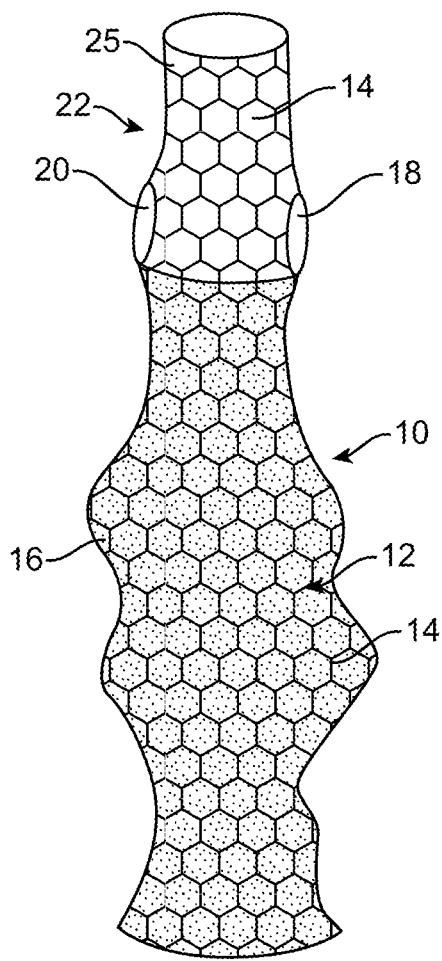
FIG. 3A illustrates an exemplary embodiment of a personalized stent graft.

FIG. 3A illustrates an exemplary embodiment of a personalized stent graft ("PSG") or prosthesis 10. The PSG 10 is shaped to conformally fit inside the AAA of a specific patient. The PSG 10 comprises a plurality of intertwined wire filaments, of material such as nitinol, twisted together in a 'chicken wire' format (also known as gabion basket fence) to form cells 12 which in aggregate form the wire frame structure 14. The wire frame 14 can be made from the filaments of any suitable material known in the art for construction of the stent grafts. The wire frame 14 can be configured to substantially match or conform to the internal geometry of the target vessel of the patient, using methods as described herein. In this disclosure, the terms filament and wire are used interchangeably. A portion of the PSG may be covered with a membrane 16 (shown as a shaded area in FIG. 3A), which may comprise a biocompatible material such as Teflon, Dacron, or silicone.

The PSG 10 may comprise one or more lateral openings or apertures, known as fenestrations in the art, such as openings 18 and 20 at its superior end. These openings can correspond to the ostia of the renal arteries RA of the patient. The location and construction of these fenestrations 18 and 20 may be determined by the anatomical image, such as a CT scan, of the AAA. These fenestrations can allow unimpeded blood flow into the renal arteries RA when the PSG is implanted. Finally, the portion 22 of the PSG 10 superior to the fenestrations 18 and 20 may optionally be uncovered by the membrane material 16. The PSG 10 may further comprise one or more radio-markers 25 which can present as opaque images during x-ray fluoro imaging, marking the superior end of the said PSG 10. This feature may be used in guiding the deployment of the PSG in the AAA.

Figure 3B:
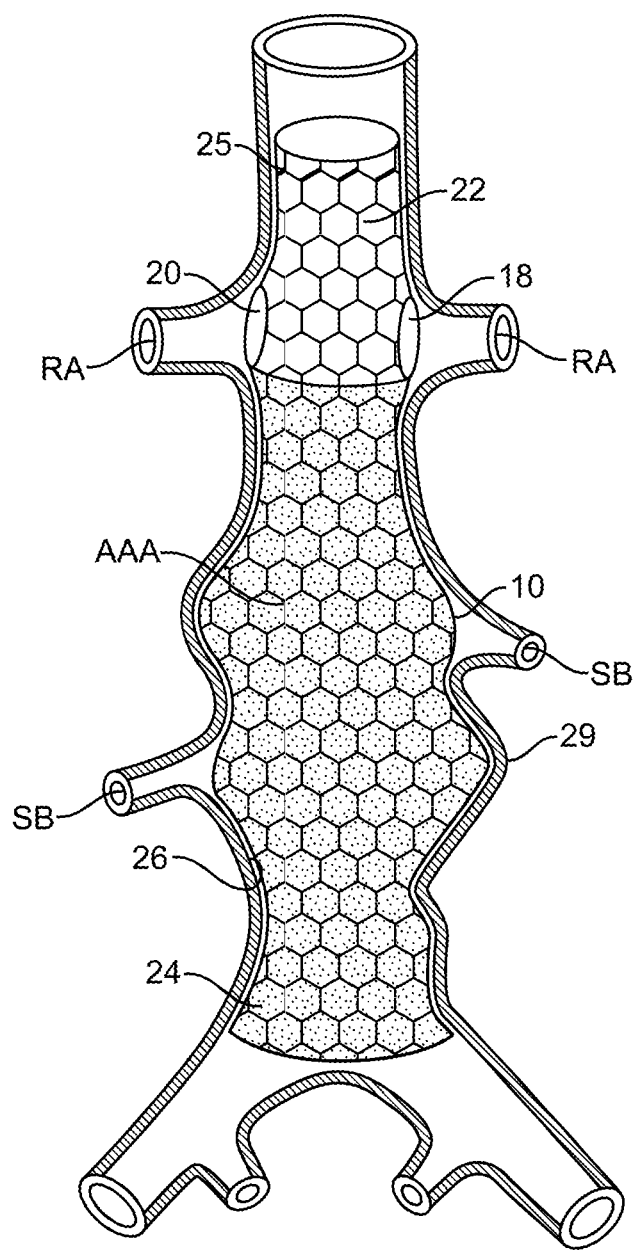
FIG. 3B illustrates the personalized stent graft of FIG. 3A installed in the AAA.

FIG. 3B shows the PSG 10 deployed in the AAA. The PSG can be positioned in the AAA in a conformal manner such that there is minimum or no space between the outer surface 24 of the PSG 10 and the inner surface 26 of the blood vessel wall 29 forming the AAA. The side branches SB can thus be blocked, and the aneurysm sac or pocket 28 as shown in FIG. 2 between the stent graft and the blood vessel wall can be eliminated, thereby preventing endoleaks.

The features and elements of a personalized prosthesis or PSG, and methods of manufacture and use thereof, are described in further detail herein.

Referring again to FIG. 2, conventional stent grafts have a requirement (known as 'indication' in FDA parlance) that there be a neck length NL available in the patient for him/her to be suitable for the EVAR treatment. The neck length NL is a region inferior to the renal arteries RA between the RA and the beginning of the bulge of the AAA. Typically, the neck length needs to be 10 mm or more for the EVAR procedure. Additionally, patients with angulated AAA (where neck length portion NL is curved), juxtarenal AAA (where the AAA involves the renal arteries, as in FIG. 1D) and suprarenal AAA (as in FIG. 1B) are excluded from the EVAR treatment mainly due to the inability to seal around the stent graft to prevent Type I endoleaks.

In the case of the PSG, all the described restrictions of the conventional stent graft can be substantially eliminated as the PSG can be fabricated to match the anatomy of the aneurysms anywhere in the aortic and/or iliac vessels. The resulting PSG can be implanted in the patient at any aneurysm location to provide a more effective treatment. A PSG or personalized prosthesis as disclosed herein can thus allow many more patients to be treated than with a conventional stent graft.

Figure 4:
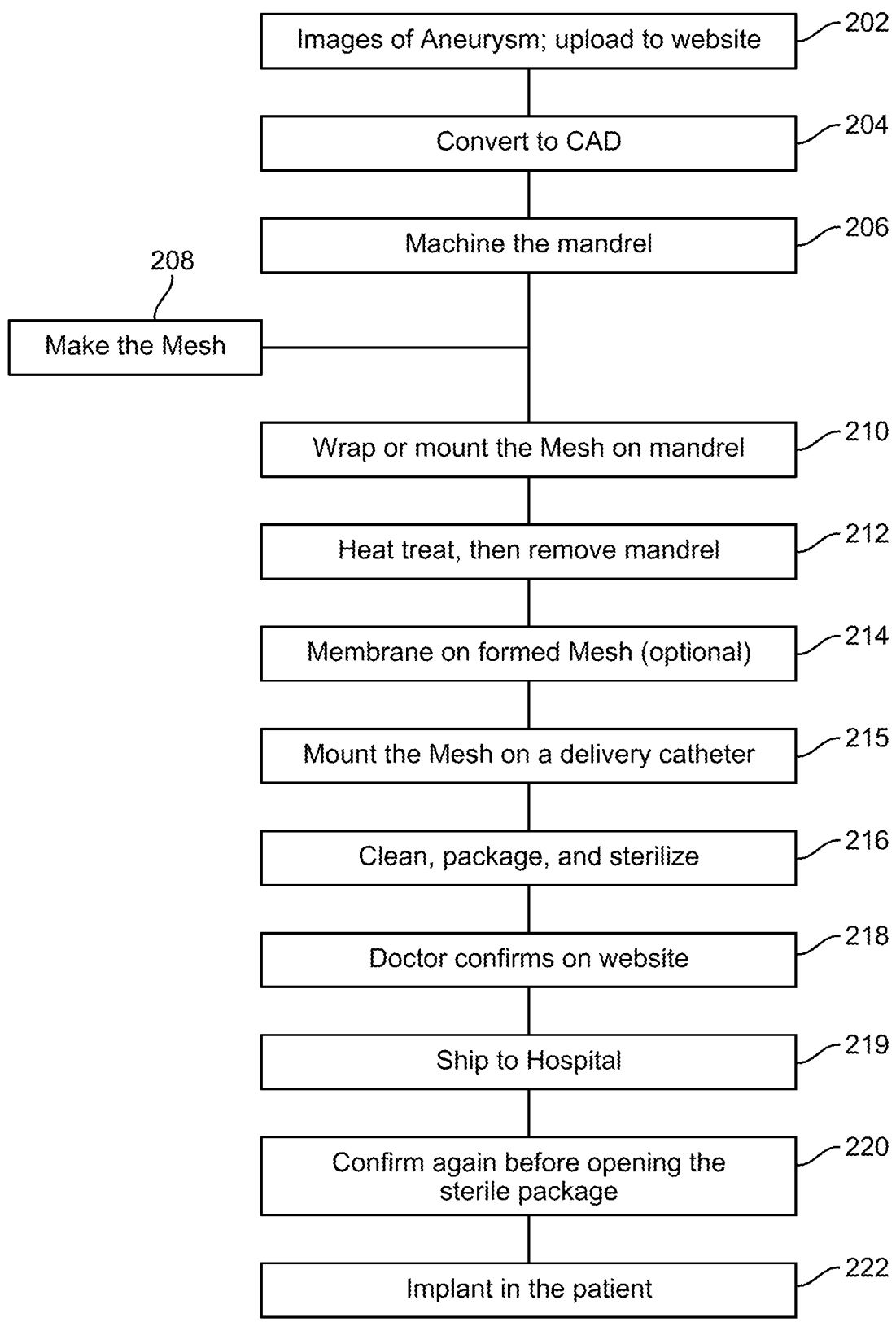
FIG. 4 illustrates a flow chart of an exemplary method of fabricating a personalized prosthesis.

FIG. 4 is a flow chart which illustrates an exemplary method of fabricating a personalized prosthesis that can be used to treat aneurysms or any other treatment region. The method includes obtaining one or more images 202 of the treatment region which in this case is an aneurysm. These images may be obtained using computerized tomography (CT), x-ray, angiography, magnetic resonance imaging (MRI), ultrasound, or other imaging techniques known to those of skill in the art. The images may be stored on any storage media such as a CD-ROM, flash memory stick, etc., or the images may be stored in the cloud, on a remote server, or any other convenient and secure location. The images may be transferred to any of these locations using the Internet. Once the images are stored, the images or the digital data representing the images may be input 204 into a computer aided design/computer aided manufacturing (CAD/CAM) system. The CAD/CAM system then converts the images into a digital data set that can then be translated into machining instructions which are provided to a machining device such as a CNC lathe (e.g., four-axis CNC machine), mill, electrical discharge machine (EDM), etc. and the machining instructions are used by the machining device to machine 206 or otherwise form a mandrel or a mold having a shape that substantially matches the shape and volume of the treatment region. Thus the contours of the mandrel will match the contours of the treatment region, and the mandrel will substantially fill the volume of the treatment region, typically a body cavity, lumen, or other passage. The CAD/CAM system may be programmed to compensate for the thickness of materials that are applied to the mandrel later on, thus the mandrel may be slightly smaller than the actual size of the treatment region. In other embodiments, the mandrel shape will match the contours of the treatment region without compensating for material thickness. In both cases, the resulting mandrel shape substantially matches the treatment region shape and size, and the mandrel will substantially fill the volume of the treatment region. For example, in the case of an abdominal aortic aneurysm, the mandrel will substantially fill the volume of the aneurismal sac as well as a portion of the aneurysm neck and legs. In other embodiments, the mandrel shape may be oversized relative to the actual size of the treatment region in order to allow the prosthesis manufactured from the mandrel to self-adjust in size to match the treatment region, as described in further detail herein.

Once the mandrel is formed, it can be used as a master mold from which a personal prosthesis is fabricated. The personal prosthesis will then have a size and shape that substantially matches the treatment region which allows the personal prosthesis to anchor itself at the treatment region and prevent endoleaks and windsocking. A wire mesh is either pre-made 208 or otherwise provided. The mesh is preferably tubular and cylindrically shaped with both ends open so that the mesh may be slidably disposed over the mandrel like a sock, or in other embodiments the wire mesh may be wound 210 on the mandrel. The mesh and mandrel are then placed in a furnace, oven, salt bath, etc. to an elevated temperature for a desired time. The mesh and mandrel are then removed and cooled using a prescribed cooling procedure such as air cooling, quenching in oil or water, etc. This heat treats 212 the wire mesh and the wire mesh takes a set to the shape of the mandrel. Heat treating of metals, in particular self-expanding metals is known in the art. The formed mesh is then removed from the mandrel. In this embodiment, or any of the embodiments disclosed herein the wire mesh is preferably self-expanding, and may be made from metals such as superelastic nitinol, and thus the mesh will have an expanded configuration which matches the mandrel and hence also substantially matches the shape of the treatment region. When tension is applied to the ends of the mesh, the mesh will collapse into a collapsed configuration which has a lower profile and is suitable for loading onto a delivery catheter for endovascular delivery to the treatment region. The wire mesh in this or any of the embodiments described herein may also be a shape memory alloy such as nitinol such that placement of the mesh in a patient's body heats the mesh above a transition temperature and causes the mesh to radially expand outward. In still other embodiments, the mesh may be balloon expandable, so it may be delivered over an expandable member such as a balloon. When the balloon is expanded, the mesh similarly expands with the balloon.

Once the wire mesh has been heat treated, a fabric or polymer coating may be applied 214 to the wire mesh to form a membrane over the wire mesh. The coating may be Dacron® polyester, expanded polytetrafluorinated ethylene (ePTFE), silicone, polyurethane, or other materials known in the art. The coating may be a sheet or tube of the material coupled to the mesh with adhesives, sutures, encapsulation, etc., or the mesh may be dip coated in order to apply the polymer to the mesh. The coating is preferably biocompatible and impermeable to blood or other body fluids. It may also be biodegradable and be made of materials such as polylactic acid (PLA) or polyglycolic acid (PGA). The resulting wire mesh with polymer coating or membrane forms a personalized implantable prosthesis having a shape that matches the treatment region and substantially fills the volume of the treatment region, in this case, the aneurismal sac. In other embodiments, the wire mesh remains uncoated and uncovered and forms the personalized prosthesis. The personalized implantable prosthesis is then coupled to a delivery system 215 such as a delivery catheter, and the system is then cleaned, packaged, and terminally sterilized 216 using manufacturing processes known to those of skill in the art. For example, packaging may comprise placing the prosthesis in a procedure tray and sealing the tray with a Tyvek® lid, and terminally sterilizing the prosthesis may comprise gassing the prosthesis with ethylene oxide, autoclaving it with steam, or irradiating it with gamma or electron beam irradiation. In alternative embodiments, the coating may be applied directly to the mandrel without the mesh, thereby forming the prosthesis.

In some embodiments, the physician optionally may then confirm 218 that the resulting personal prosthesis is indeed the correct one for a particular patient prior to shipping the prosthesis from the factory. The verification may be conducted visually over the Internet or via the cloud by verifying size, shape, or dimensions of the prosthesis. Once the verification is complete, the personal prosthesis may be shipped 219 from the manufacturing facility to the doctor at a hospital, surgicenter, clinic or other place of business. Once received, the doctor may then optionally re-verify 220 that the prosthesis is the correct size and shape for the patient prior to opening up the sterile package. If the prosthesis is incorrect, it may be returned to the manufacturing facility. Verification may be accomplished by scanning a bar code and/or using the Internet or via connection to cloud servers. Once verification is complete, the personal prosthesis may be implanted 222 in the appropriate patient. One of skill in the art will also appreciate that appropriate patient privacy must be maintained during the entire personalized manufacturing process as required by the Health Insurance Portability and Accountability Act (HIPAA). In an alternative embodiment, the mesh alone may be formed over the mandrel and then delivered as described herein to treat the diseased or damaged tissue. Similarly, in another alternative embodiment, a resilient polymer may be formed directly over the personalized mandrel without the mesh. This may then be used to treat the diseased or damaged tissue as described herein.

Figure 5B:
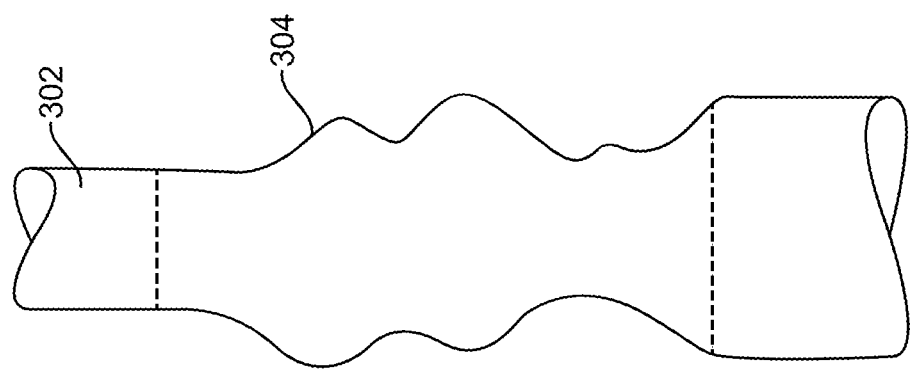
Figure 5A:
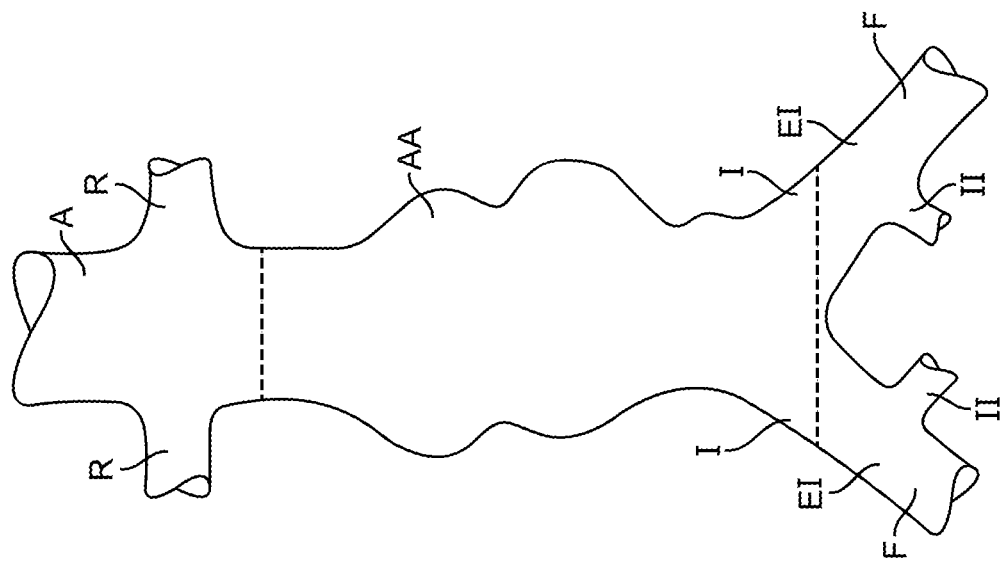
Figure 5C:
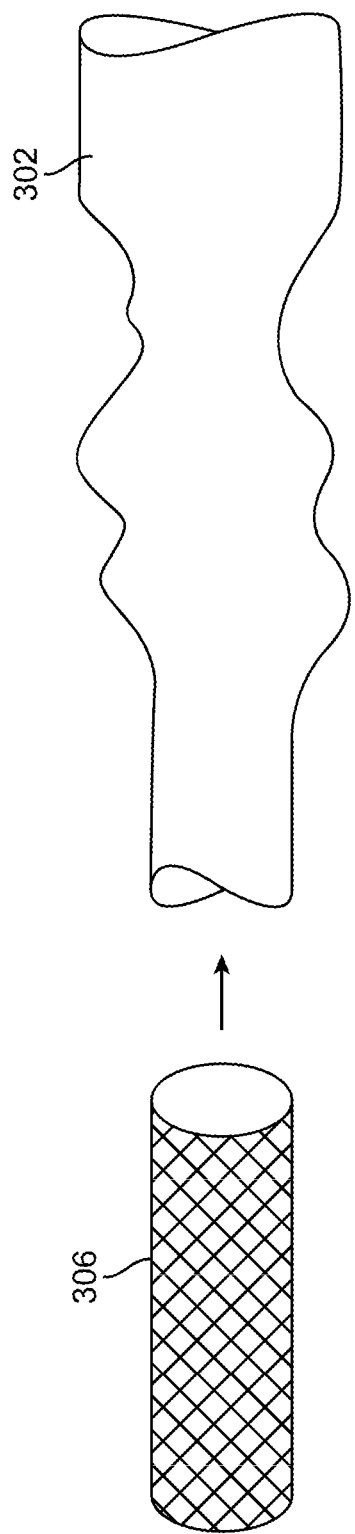

FIGS. 5A-5I illustrate exemplary methods of fabricating a personalized prosthesis or PSG for treatment of an aneurysm. FIG. 5A illustrates an infrarenal aneurysm AA similar to that illustrated in FIG. 1C above. Using the fabrication technique described above, images of the aneurysm may be obtained using CT scans, or any of the other techniques described herein or known in the art. The image is then used to create a mandrel 302 having a surface 304 which substantially matches the contours of the inner wall of the aneurysm, as shown in FIG. 5B. For example, the mandrel may be machined from a piece of stock, or it may be 3-D printed or molded. The mandrel may be made slightly undersized in order to accommodate for material thicknesses that are disposed on top of the mandrel, or the mandrel may be made oversized to provide a slightly oversized prosthesis. Alternatively, as described in further detail herein, the mandrel may be made oversized to produce a slightly oversized prosthesis that can self-adjust its shape and dimensions when deployed within an aneurysm. The mandrel may be made from a metal such as stainless steel or aluminum, or any other material that resists the heat experienced during heat treatment, such as a suitable ceramic material or polymeric material. Once the mandrel is made, a wire mesh 306 may be disposed over the mandrel 302 such that the mesh takes the shape of the mandrel and hence the mesh then also has a shape which substantially matches the shape of the aneurysm. In some embodiments, the wire mesh 306 may be pre-fabricated into a tubular sock-like shape that can be easily placed over the mandrel as seen in FIG. 5C. Alternatively, the wire mesh may be wound and formed over the mandrel. In some embodiments, as seen in FIGS. 5D-5F, a flat preformed mesh 306a (best seen in FIG. 5D) may be wrapped around the mandrel 302 as seen in FIG. 5E. Once wrapped, the ends of the flat mesh may be affixed to one another using methods known in the art such as welding, suturing, tying, bonding, soldering, etc. The mesh is then circumferentially disposed around the mandrel as seen in FIG. 5F. A ribbon, wire, or other filament may be wrapped over the mesh to ensure that it contacts the mandrel.

FIG. 5G illustrates the wire mesh disposed over the mandrel. The mandrel and mesh are then heat treated as described herein so that the wire mesh is set to take the shape of the mandrel. The mesh preferably comprises a nitinol material and is self-expanding, such that the mesh may be collapsed into a collapsed configuration for delivery, and the wire mesh may self-expand into an expanded shape which matches the mandrel and the aneurysm shape. After heat treatment is completed, the mesh and mandrel may be dip coated with a polymer, or the polymer or fabric cover 310 may be applied to the mesh using methods described herein or known to those of skill in the art. The polymer or fabric cover or membrane 310 may be resilient or flexible to withstand deformation as the mesh is collapsed and expanded, and is preferably impermeable to blood to prevent blood from flowing across the wall of the prosthesis. Radiopaque markers 308 or other indicator markers are optionally attached to the polymer or fabric cover or membrane and/or to the wire mesh. The personalized prosthesis or PSG is now complete and can substantially match the anatomy of the aneurysm. The personalized prosthesis, when deployed within the aneurysm after which it was modeled, can seat itself in the aneurysm, thereby anchoring the prosthesis in proper position and further excluding the aneurysm from blood flow, thus preventing endoleaks. FIG. 5H illustrates the personalized prosthesis with markers 308 once the mandrel has been removed. The prosthesis can be loaded onto a delivery catheter or other delivery device and implanted at the site of the aneurysm as seen in FIG. 5G. Prosthesis delivery and implantation methods are described in further detail herein.

Figure 6A:
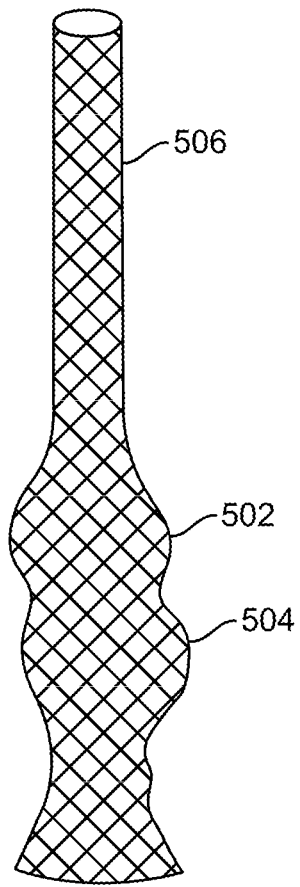
FIGS. 6A-6C illustrate another exemplary embodiment of a personalized prosthesis.
Figure 6B:
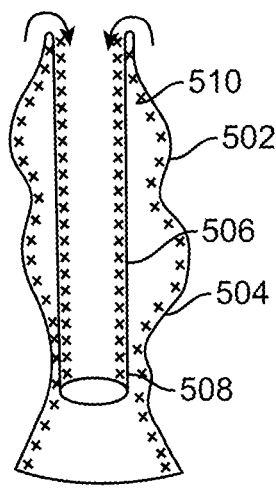
Figure 6C:
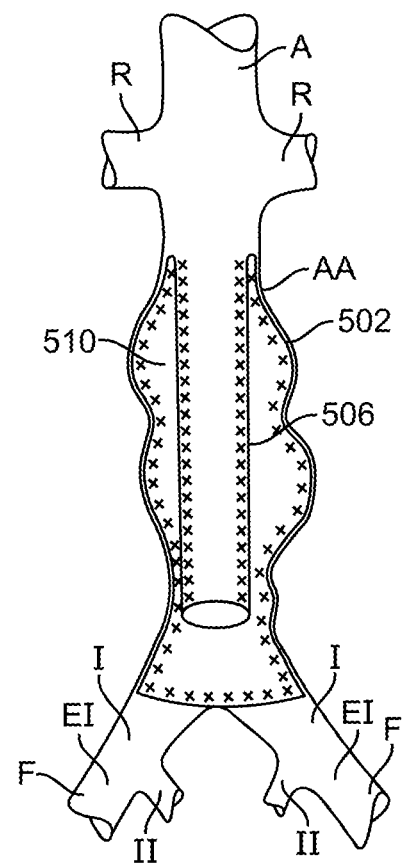

FIGS. 6A-6C illustrate an exemplary embodiment of a personalized prosthesis that forms a new lumen for blood flow. The aneurysm may be imaged and the corresponding mandrel manufactured to substantially match the aneurysm shape, as described herein. Once the mandrel is fabricated, the mesh and/or polymer may be applied to the mandrel as described herein. In the embodiment shown in FIGS. 6A-6C, the resulting prosthesis 502 includes a main body section 504 that matches the size and shape of the aneurysm, and also includes an elongated neck portion 506. As shown in n FIG. 6B, the elongated neck 506 may be invaginated as indicated by the arrows such that the elongated neck portion 506 becomes disposed inside the main body portion 504. The space 510 between the neck portion 506 and the inside wall of the prosthesis 502 may be left as is, or it may be filled with a fluid, solid, or other material. The elongated neck portion 506, which is preferably a cylindrically shaped tube, can now act as a lumen for blood flow therethrough. The free end 508 of the elongated neck 506 may be left as is, or it may be anchored to prevent flapping. Anchoring may be accomplished with a stent, sutures, or staples, or the elongated neck may be sized such that the blood pressure opens the free end up fully and lodges it against a downstream and inner portion of the prosthesis. The free end 508 may also be sealed with the prosthesis in case the space 510 is filled with a material. FIG. 6C illustrates the personalized prosthesis of FIG. 6B delivered into an infrarenal aortic aneurysm AA. This embodiment allows creation of a lumen which more accurately matches the natural blood flow path before the aneurysm enlarged the blood flow path. Delivery of the personalized prosthesis may be by any of the methods described herein.

Figure 7:
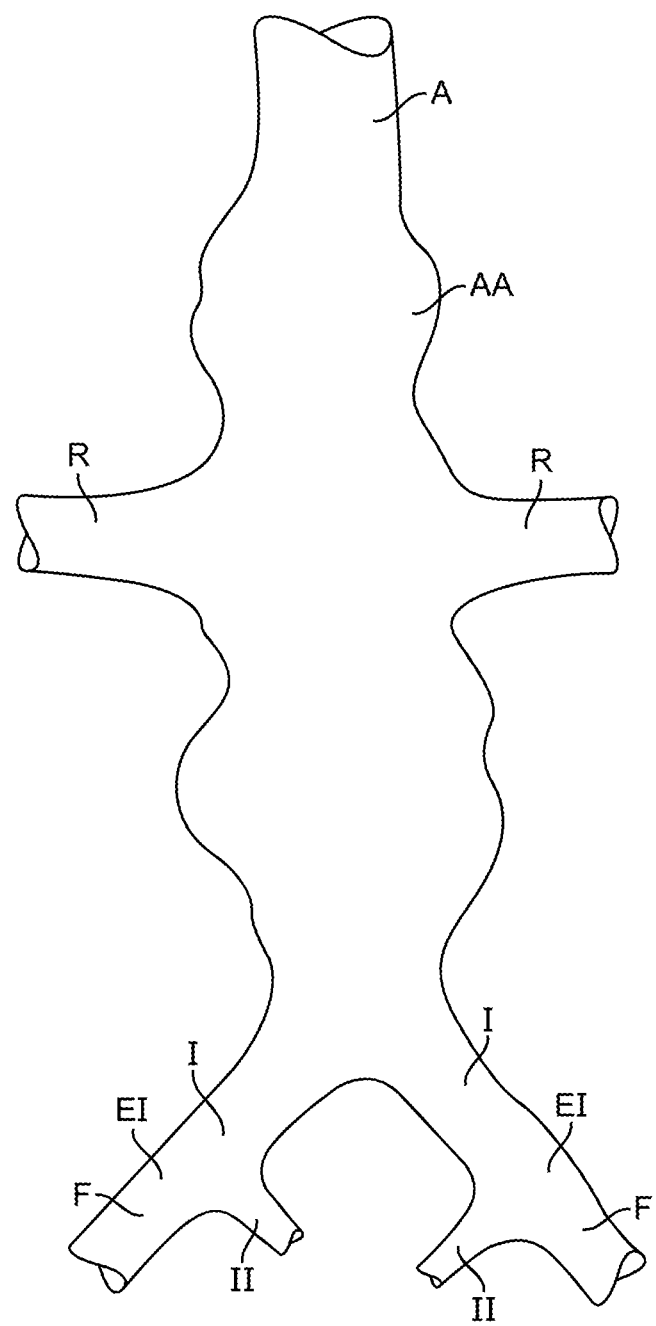
FIG. 7 illustrates a juxtarenal aneurysm.

In aneurysms extending over one or more side branch vessels, a mesh-only personalized prosthesis may be disposed over the ostium of the side branch without substantially blocking blood flow to the side branch. A personalized prosthesis with a polymer or fabric coating over a wire mesh may be used, but such a prosthesis may obstruct blood flow into the side branch vessels. For example, a juxtarenal aneurysm AA as seen in FIG. 7 extends across part of the aorta A, and involves the renal arteries R. In this exemplary aneurysm, the iliac arteries I, external iliacs EI, internal iliacs II, and femoral arteries F remain unaffected by the aneurysm. In this case, implanting a conventional graft or a prosthesis comprising a polymer or fabric coating to exclude the aneurysm can obstruct blood from flowing into the renal arteries, resulting in damage to the kidneys. Thus, an improved and personalized prosthesis not only has a size and shape to match the anatomy of the treatment site, but also can accommodate for side branch vessels, or other side branch lumens and passageways.

Figure 8:
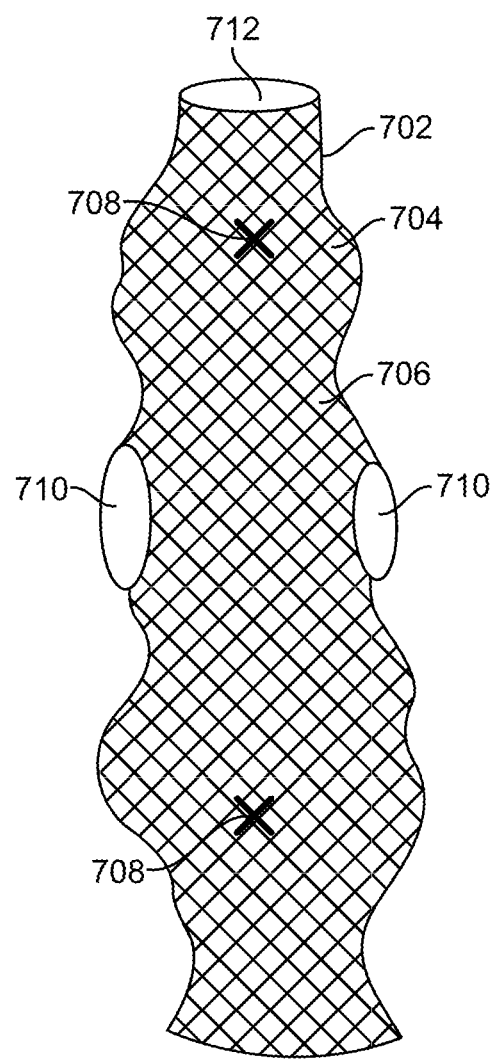
FIG. 8 illustrates a personalized prosthesis that accommodates side branch vessels.
Figure 9:
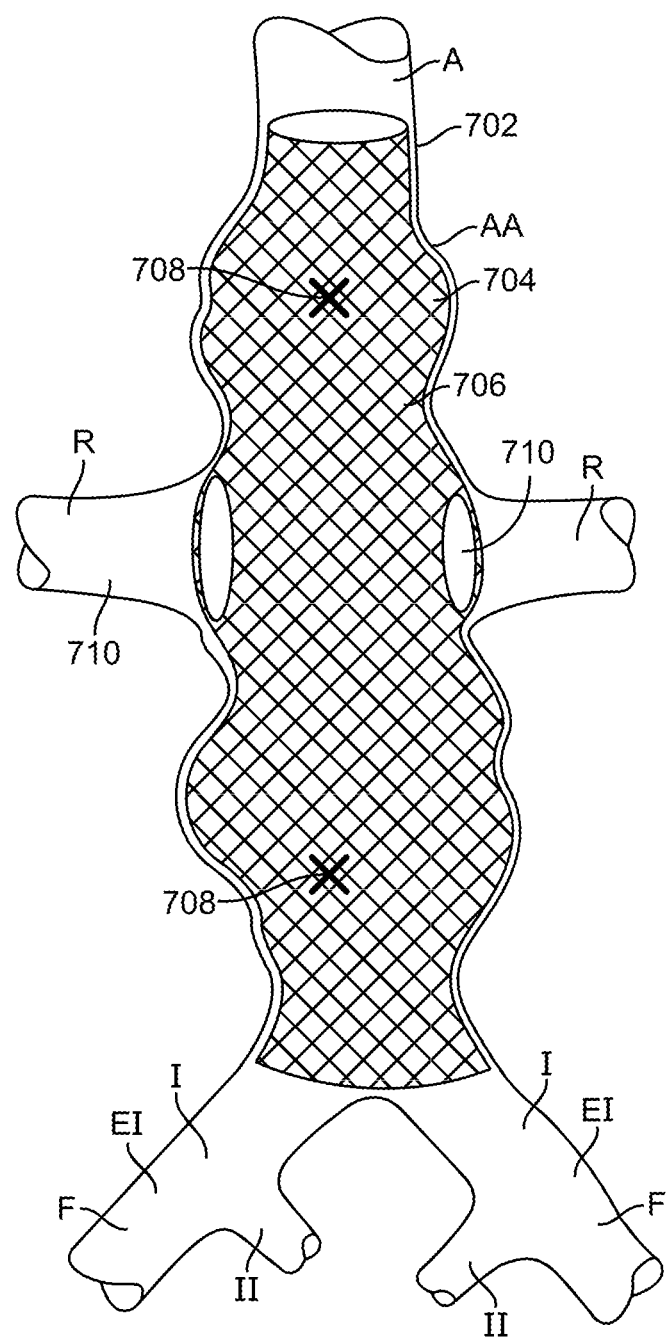
FIG. 9 illustrates implantation of the prosthesis of FIG. 8 in a juxtarenal aneurysm.

FIG. 8 illustrates an exemplary embodiment of a personalized prosthesis that can accommodate side branches such as the renal arteries. The personalized prosthesis 702 includes a wire mesh 704 and an optional polymer or fabric cover 706 as described herein. The prosthesis 702 may also optionally include radiopaque markers 708 to facilitate visualization and placement. The personalized prosthesis may be fabricated in a similar manner as described herein, and also include apertures or fenestrations 710 in a sidewall of the prosthesis that are in fluid communication with the central channel 712 of the prosthesis. The side apertures are positioned along the prosthesis so that they match the location of the side branch vessels or body passages such as renal arteries. The location of the apertures may be accurately determined based on the image obtained, such as a CT scan and the like. During manufacturing of the prosthesis, one or more additional mandrels that extend laterally away from the main forming mandrel may be coupled with the main forming mandrel at locations corresponding to the locations of the side branch vessels. The laterally-extending mandrels can maintain the apertures in the wire mesh, and also maintain the apertures once the mesh and mandrel are dip coated into a polymer, or when a polymer or fabric cover are otherwise applied to the mesh. The prosthesis 702 can then be loaded into a delivery catheter as described herein. The prosthesis can then be deployed using the radiopaque markers to guide the axial placement of the prosthesis along the aorta, such that the side apertures 710 align with the ostia of the side branch vessels. FIG. 9 shows the prosthesis 702 deployed in the juxtarenal aneurysm of FIG. 7, with the apertures 710 aligned with the ostia of the renal arteries R. Thus blood flow is not only maintained through the prosthesis across the aneurysm, but also to the renal arteries. While the filaments may partially cover the ostia, such a partial covering of the ostia with wire filaments generally would not significantly obstruct blood flow to the side branches.

Figures 10A, 10B:
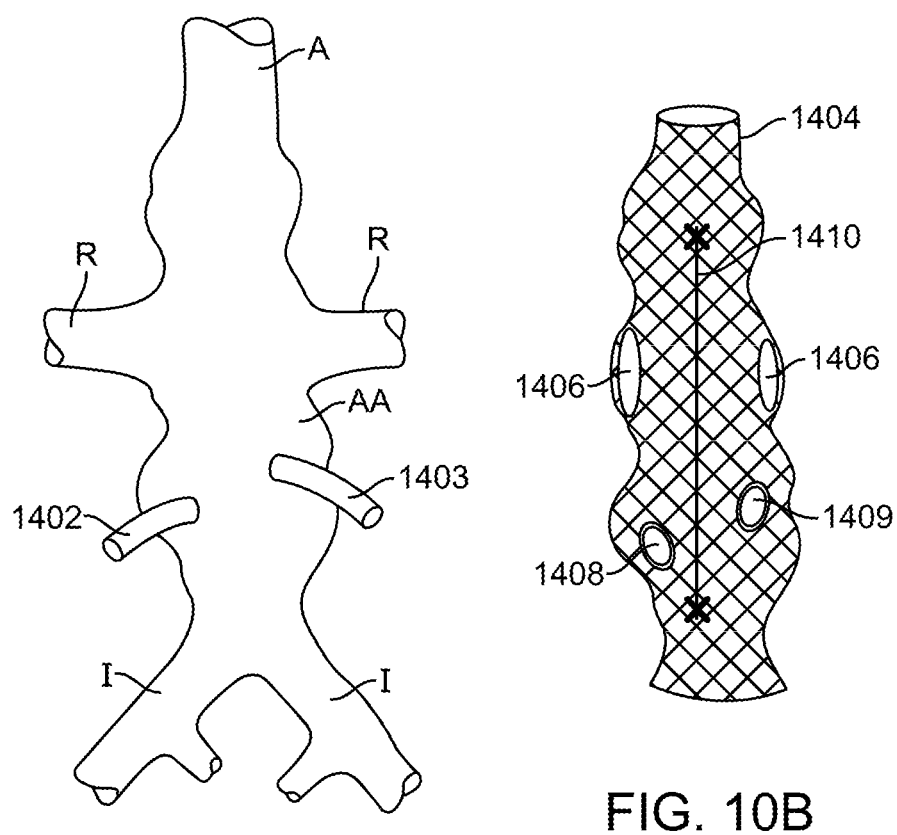
FIGS. 10A-10B illustrate an exemplary embodiment of a prosthesis accommodating side branches.

FIGS. 10A-10B illustrate another embodiment of a personalized prosthesis that accommodates for the renal arteries as well as other side branch vessels. In FIG. 10A the aneurysm AA is disposed in the aorta A and extends across the renal arteries R and also across other side branch vessels 1402 and 1403 that are between the iliac arteries I and the renal arteries R. The aneurysm is imaged as described herein, and a central mandrel matching the aneurysm is then fabricated. The location of the renal arteries and/or one or more side branch vessels may be determined based on one or more images of the aneurysm (e.g., CT scan images), or a digital data set created from the one or more images. Additional mandrels are laterally positioned where the renal arteries and the side branches are located. The mesh is then woven over the mandrel and around the side branch mandrels so that an aperture is maintained at their location. In alternative embodiments, the mesh is pre-woven and the loaded over the mandrel. The side branch mandrels are placed into the mandrel to push the filaments of the mesh away thereby creating and preserving openings for the renal or other side branches. After heat treating and other processing including putting an optional polymer or fabric coating over the mesh, a personalized prosthesis 1404 is produced as seen in FIG. 10B. Any of the mesh patterns disclosed herein may be used. The prosthesis includes apertures 1406 configured to match with the ostia to the renal arteries, and apertures 1408 and 1409 configured to match with the ostia to the other two side branches shown in FIG. 10A. The apertures 1406, 1408 and 1409 are in fluid communication with the central channel of the prosthesis so that blood flow will remain unobstructed to the renal arteries or the side branch vessels. An optional radiopaque marker 1410 may also be included on the prosthesis in order to help align the prosthesis with the renal arteries and side branches during delivery. The radiopaque marker may include a long linear portion that indicates the longitudinal axis of the prosthesis. The radiopaque marker may be formed from a dense metal such as gold or platinum, or rhodium alloy that is coupled to the mesh. The renal arteries or other side branches themselves may be used during alignment by injecting contrast media through the vessels while visualizing the prosthesis and surrounding vessels under fluoroscopy or using other visualization techniques known in the art.

Figure 11:
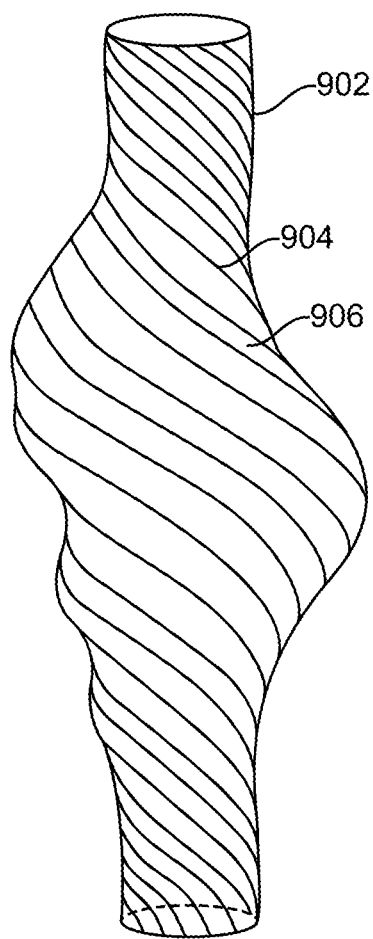
FIG. 11 illustrates an exemplary mesh.
Figure 12A:
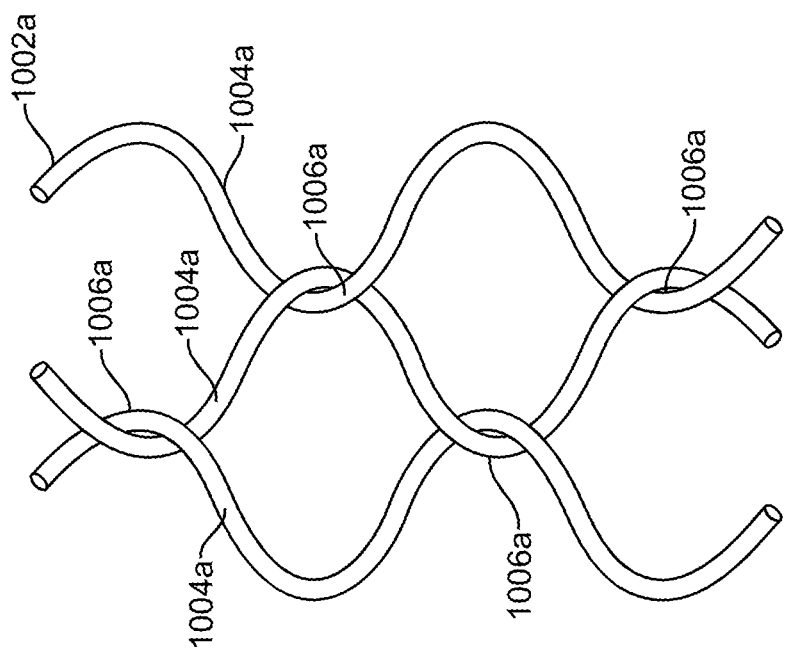

The personalized prostheses described herein preferably include a wire mesh that self-expands to the personalized shape. Various wire patterns may be used to create the mesh. For example, FIG. 11 illustrates a mesh 902 having one or more filaments 904 which are spirally wound and an optional polymer or fabric cover 906 is applied to the mesh. This pattern of forming the mesh is advantageous because there is no overlap of the filaments, and the spiral pattern helps the mesh to be collapsed into a low profile for delivery. FIGS. 12A-12F illustrate other exemplary mesh patterns. FIG. 12A illustrates a mesh 1002*a* having one or more filaments 1004*a* that interweave with one another similar to traditional fencing wire or chicken wire, to form a single overlapping or twisted region 1006*a*. The overlap region is preferably in every row and every column of the mesh where the filaments meet. The overlapping region forms a protuberance which may be advantageous since the protuberance may help embed the prosthesis into the tissue at the treatment site thereby helping to anchor the prosthesis. Having a single overlap of the filaments helps the filaments move relative to one another thereby allowing the prosthesis to be easily collapsed which is desirable during loading onto a delivery system and also helps to keep the profile of the prosthesis minimal. This is also advantageous since it allows the prostheses to expand and collapse in concert with the pulsatile nature of the blood as it flows through the aorta or other vessel. However, in some circumstances, the single overlapping or twisted region may not be secure enough to keep the mesh in its formed pattern or to provide adequate support to the aneurysm, especially when the prosthesis is under tension or compression because the wires in the mesh may slip or slide relative to one another. The prosthesis undergoes tension and compression during loading on a delivery system, during deployment, and after implantation due to the pulsatile nature of blood flow.

Figure 12B:
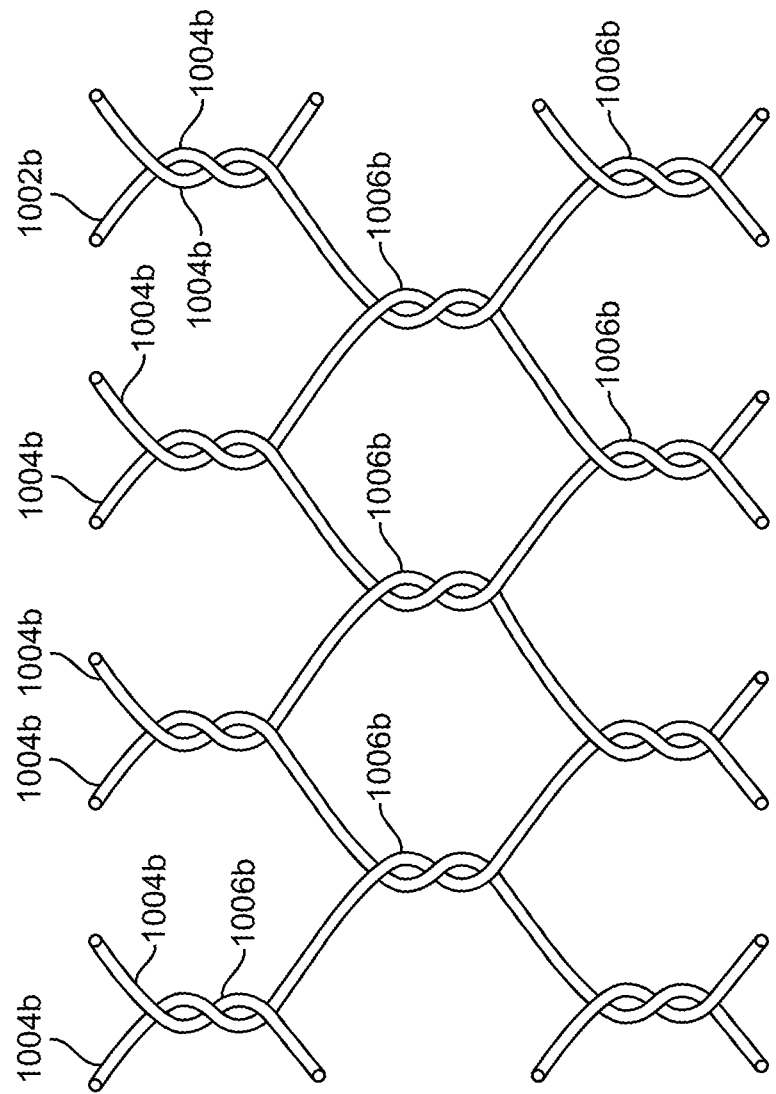

FIG. 12B illustrates an alternative embodiment of a mesh pattern that is more secure than the embodiment of FIG. 12A. Mesh 1002*b* has one or more filaments 1004*b* that interweave with one another to form a double overlapping or twisted region 1006*b*. The overlap region is preferably in every row and every column of the mesh where the filaments meet. The overlap region forms a protuberance similar to that in FIG. 12A and thus may also be useful in anchoring the prosthesis. Having the double overlapped or twisted region secures the filaments together more tightly and thus helps prevents the filaments from slipping or sliding relative to one another when the prosthesis is under tension or compression. Thus the prosthesis retains its shape and provides more support than the embodiment in FIG. 12A. However, in some circumstances, the wires may still slip or slide relative to one another, thus further securing of the filaments may be needed.

Figure 12C:
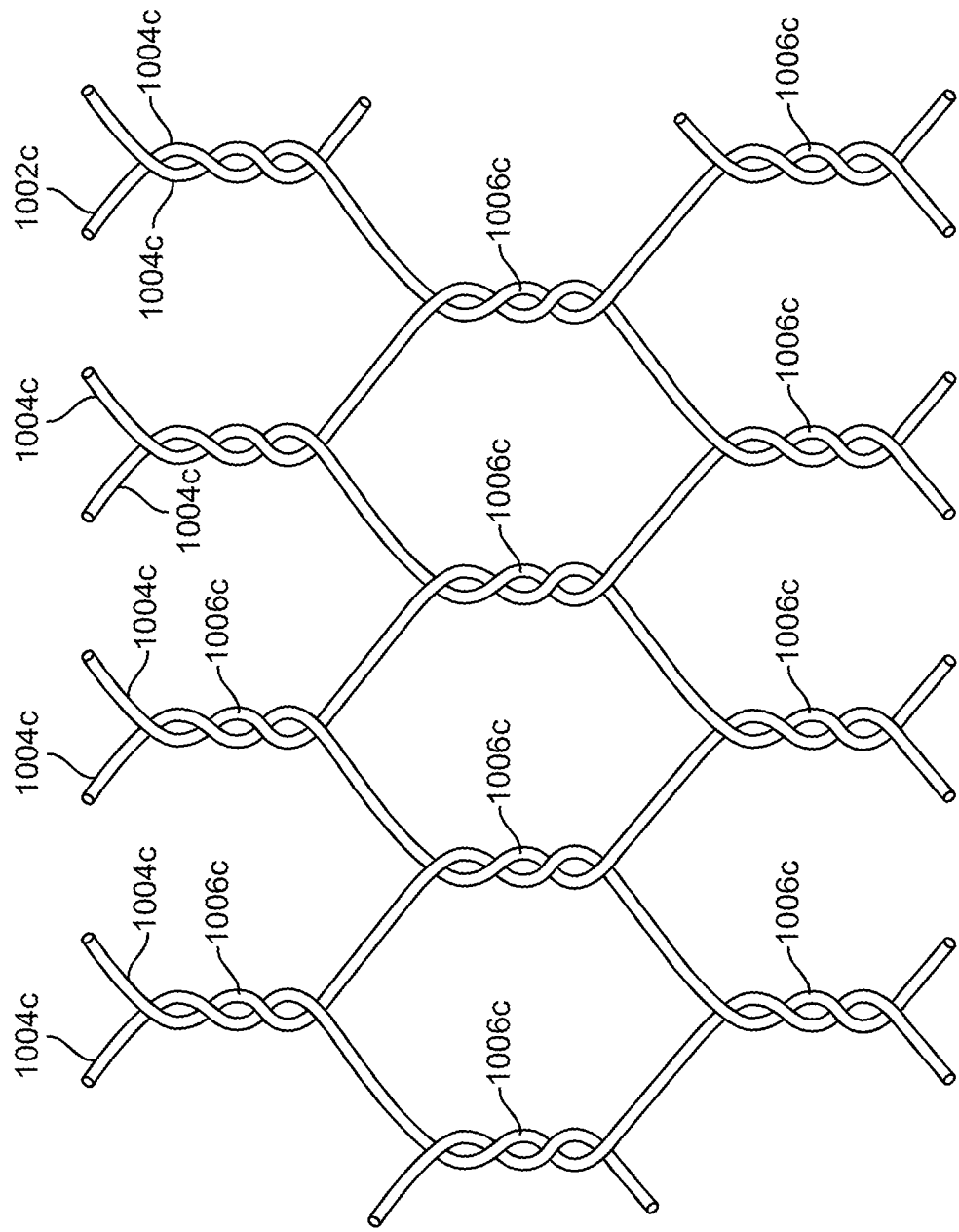

FIG. 12C illustrates still another embodiment of a mesh pattern which helps provide a stable mesh. The mesh 1002*c* has one or more filaments 1004*c* that interweave with one another to form a triple overlapping or twisted region 1006*c*. The overlap region is preferably in every row and every column of the mesh where the filaments meet. The overlap forms a protuberance similar to those previously discussed and therefore may aid in anchoring of the prosthesis. Having the triple overlap or twisted region secures the filaments together even more tightly than in the previous embodiments and thus the filaments are further constrained from slipping or sliding relative to one another when the prosthesis is under tension or compression. In some circumstances, having the triple overlap region secures the filaments together tightly enough that they cannot move at all relative to one another when the prosthesis is under tension or compression. If the filaments cannot move at all relative to one another, this prevents the prosthesis from axially or radially expanding or contracting which interferes with its ability to be loaded in a collapsed configuration onto a delivery system, from expanding radially outward upon deployment, or from expanding an contracting in concert with the vessel wall due to pulsatile blood flow.

Figure 12D:
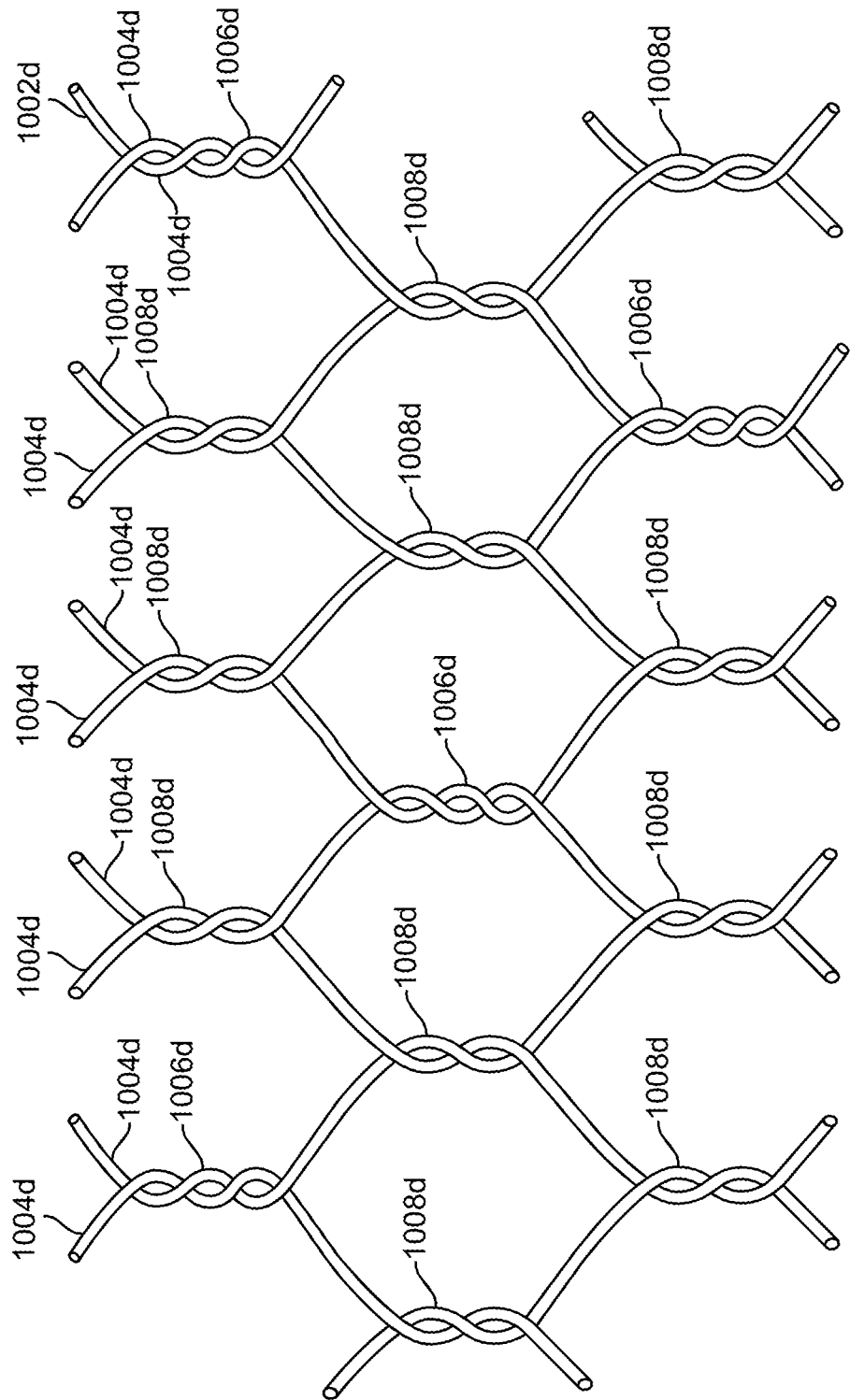

FIG. 12D illustrates a preferred embodiment of a hybrid mesh pattern that secures the filaments together securely so that the prosthesis holds its shape and provides good support during tension and compression, and yet at the same time still allows some movement between the filaments so that the prosthesis can expand and contract. Mesh 1002d has one or more filaments 1004d that interweave with one another to form an alternating pattern of a triple overlap or twisted region 1006d followed by three double overlap or twisted regions 1008d. The pattern then repeats itself horizontally, and the next row shifts by one twist to the right. Thus the triple twist in one row is offset from the triple twist in the next row, and is followed by another set of double twisted or overlapped regions 1008d, and then the pattern repeats. The pattern repeats so that everywhere the filaments overlap with one another, there is either a double or triple overlap or twisted region. The overlap region forms a similar protuberance as previously described which may be useful for anchoring the prosthesis. This hybrid weave has the advantages of both the double and triple overlap weaves previously described. Thus, the triple overlap regions secure the filaments together to minimize their movement relative to one another during compression or tension and thus the prosthesis holds its shape and provides good support, while at the same time the double overlap regions allow some movement of the filaments relative to one another thereby allowing the prosthesis to axially and radially expand and contract during delivery, deployment, and after implantation. The weave preferably minimizes or substantially eliminates axial expansion and contraction while allowing radial expansion and contraction.

FIGS. 12E-12F illustrates expansion and contraction of a personalized prosthesis such as those described above using the weave of FIG. 12D. Without being bound by any particular theory, it is believed that the filaments will remain tightly engaged with one another when the prosthesis 1002d is under tension such as while the heart is in systole as seen in FIG. 12E and represented by arrows 1018d. Here, the filaments 1004d remain tightly wound together in both the double overlap region 1008d as well as the triple overlap region 1006d. The gap 1012d between adjacent filaments wound together in a region 1008d may be represented by distance Si and the pitch 1010d or spacing between adjacent columns of wound filaments may be represented by distance P1 during systole. When the prosthesis is compressed such as when the heart is in diastole, as indicated by arrows 1020d in FIG. 12F, the pitch or spacing 1014d, represented by distance P2, between adjacent columns of wound filaments generally decreases relative to the expanded configuration as shown in FIG. 12E. Moreover, the gap 1016d between adjacent filaments wound together in a double overlap region 1008d increases relative to when the prosthesis is in the expanded configuration thereby allowing the filaments to slide relative to one another. Adjacent filaments wound together in a triple overlap region 1006d remain twisted together and there is substantially no relaxation, such that the gap between the adjacent filaments does not change substantially. Thus, when viewing the prosthesis laying on its side with its longitudinal axis horizontal, the triple-double-double-double horizontal weave pattern accommodates the motion of the aorta vessel wall caused by the pulsatile motion of the blood flowing through it. Of course, one of skill in the art will appreciate that this particular pattern is not intended to be limiting. Other patterns may be used including any combination or permutation of the single, double, triple, or more than three overlapping regions.

Figure 12G:
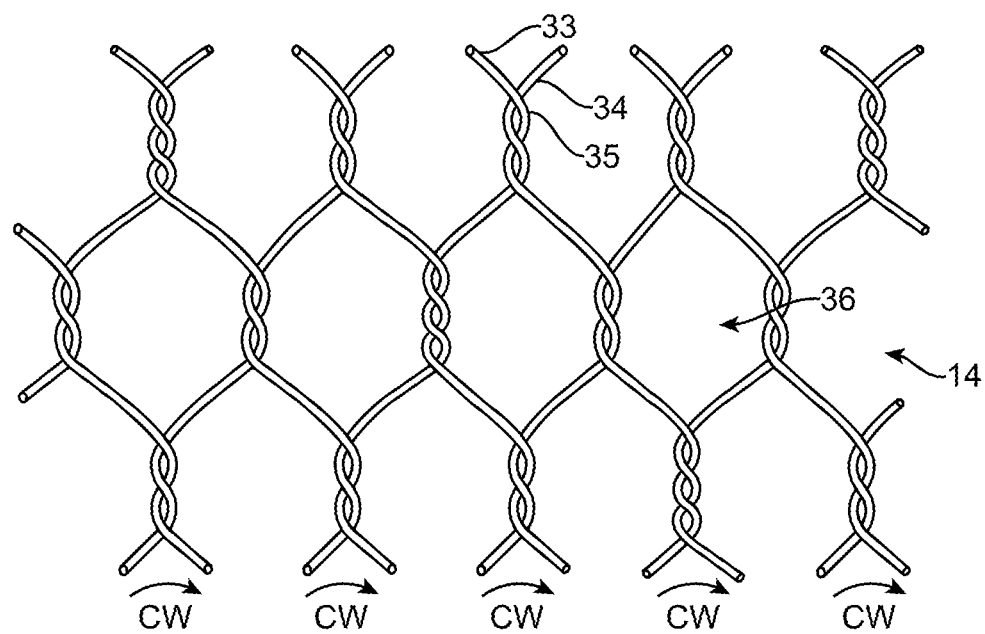
Figure 12H:
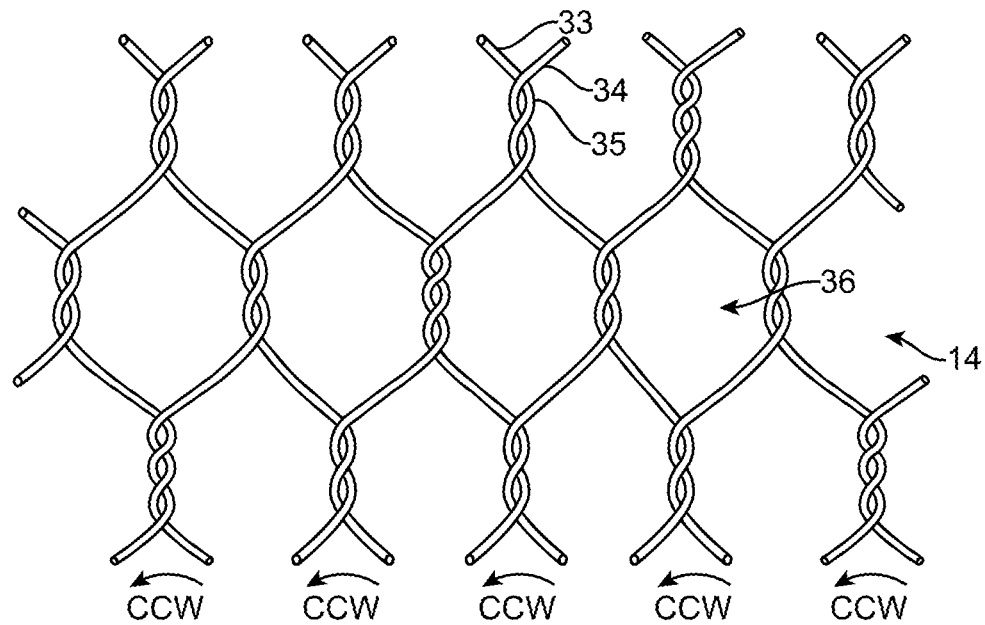

FIGS. 12G and 12H show additional details of the intertwining of the wire filaments that make up the wire mesh of the personalized prosthesis. Typically, two neighboring filaments 33 and 34 are twisted together against each other in a manner 35. A plurality of twisted portions collectively defines a cell 36, and the plurality of the cells 36 in turn form the frame 14. The cells may have a substantially hexagonal shape comprising six sides. The twist 35 can be formed by twisting the neighboring filaments 33 and 34 either in a clockwise (cw) direction as shown in FIG. 12G, or a counterclockwise (ccw) direction as shown in FIG. 12H. The direction of the twists can be clockwise for all the twists comprising the wire frame 14. Conversely, all the twists forming the wire frame 14 can be of counterclockwise direction. Alternatively, the wire frame 14 can be constructed with wire twists of any other orderly or random mix of cw and ccw twist directions. The direction of the twists may influence delivery and implantation of the device, particularly the rotational orientation of the prosthesis with respect to the lumen when implanted. Thus, the direction of the twists of the prosthesis may be specifically configured to enable self-alignment or self-orientation of the prosthesis in the proper rotational orientation when implanted in the lumen, as described in further detail herein.

Figure 13:
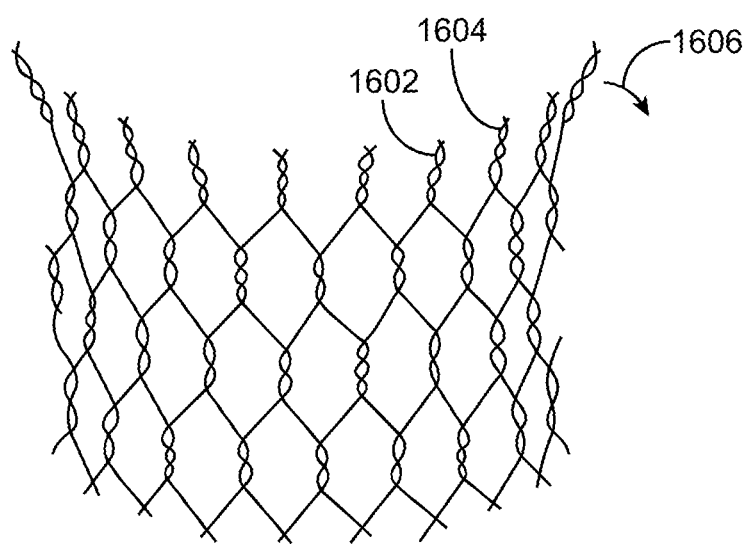
FIG. 13 illustrates an exemplary embodiment of an end of a prosthesis.

The filaments on the proximal and distal ends of the prosthesis may be terminated in any number of ways. FIG. 13 illustrates one exemplary embodiment. The prosthesis 1602 has the triple-double-double-double weave pattern of FIGS. 12A-12F described above. The filaments may terminate in an end region 1604 by twisting the filaments such that they overlap one another four times. One of skill in the art will appreciate that this is not intended to be limiting and the number of overlapping regions may be one, two, three, four, five, six, or more. Additionally, the ends may remain extending axially outward to help anchor the prosthesis in tissue by partially piercing the tissue, or the ends may be formed into curves, loops, or other shapes to prevent sharp ends from protruding and causing tissue trauma. This prevents the filaments from moving relative to one another. Additionally, the end region 1604 may then be bent slightly radially outward 1606 to form a skirt or flanged region which flares outward and thus can embed into the vessel wall to help anchor the prosthesis.

Figure 14:
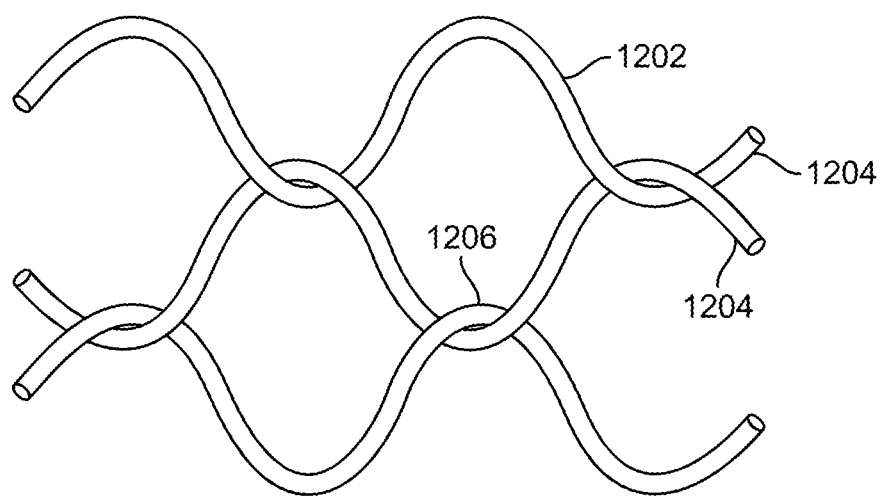
FIG. 14 illustrates an exemplary mesh.

In the embodiments of FIGS. 12A-12F, the weave pattern has been described when the prosthesis is sitting on its side such that the longitudinal axis of the prosthesis is generally horizontal. Thus, the weave pattern is generally parallel to the longitudinal axis, and the filaments are weaved together in a horizontal pattern across the prosthesis and with a vertical orientation. In still other embodiments, the weave pattern of FIGS. 12A-12F may be rotated ninety degrees so that the filaments are weaved an orthogonal direction. FIG. 14 illustrates an exemplary embodiment of the weave pattern in FIG. 12A rotated ninety degrees. The weave is illustrated with the prosthesis laying flat on its side with its longitudinal axis generally horizontal. Thus, mesh 1202 includes a plurality of filaments 1204 that are weaved together to form a single overlap or twisted region 1206. Other aspects of this embodiment generally take the same form as in FIG. 12A. The other embodiments described previously may also be weaved in a pattern that has been rotated ninety degrees. Any of the mesh patterns described herein may be formed into a round tubular member or the mesh may be woven into a flat sheet and the ends may be joined together to form a round tubular member. Additionally wires or filaments of different diameters may be combined with one other, or a single diameter may be used throughout a single mesh prosthesis in order to obtain desired mechanical properties.

Figure 15:
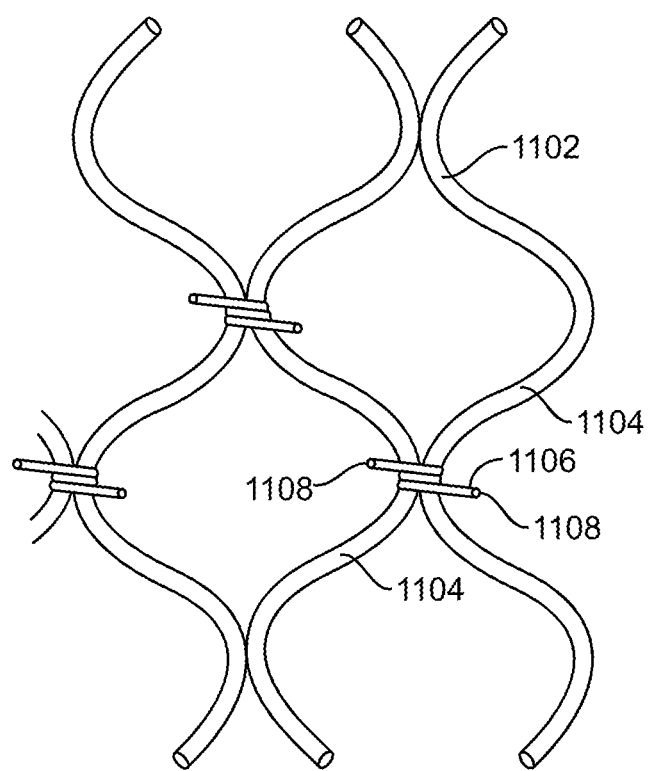
FIG. 15 illustrates another exemplary embodiment of a mesh pattern.

FIG. 15 illustrates still another pattern for the mesh 1102. This pattern has one or more filaments 1104 woven into an undulating pattern. Adjacent rows of the undulating filaments are tied together with a wire, suture, or other tie 1106. Optionally, one or both ends of the tie 1106 may be left uncut to form a barb 1108 that can also be used to help anchor the prosthesis to tissue at the treatment site. Any of these wire mesh patterns with anchoring or without anchoring may be used in any of the embodiments described herein.

Figure 16:
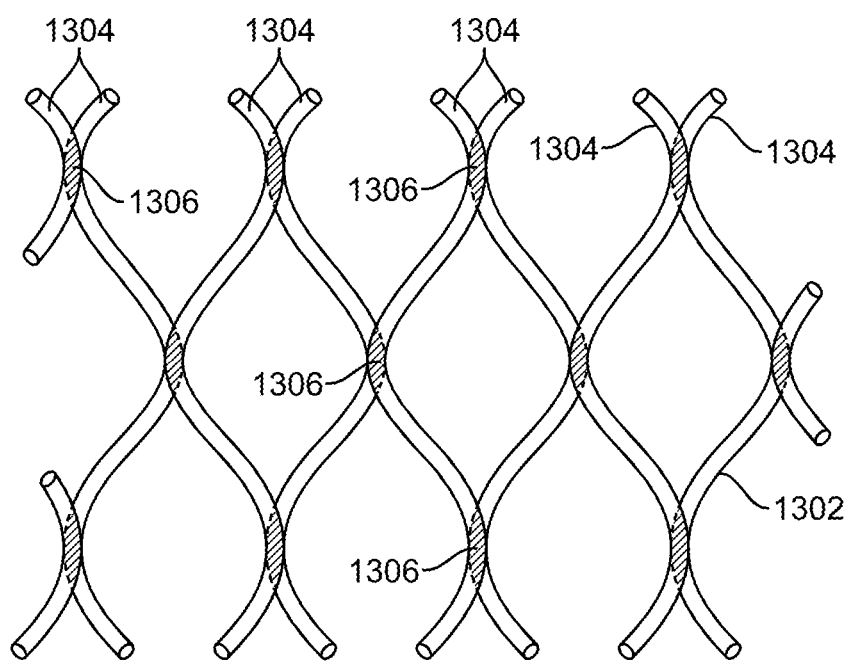
FIG. 16 illustrates yet another exemplary embodiment of a mesh.

FIG. 16 illustrates yet another exemplary embodiment of a mesh. The mesh 1302 includes one or more filaments 1304 which are formed into an undulating pattern having peaks and valleys. The peaks and valleys in one row of the mesh may overlap with the valleys and peaks of an adjacent row of the mesh. The overlapping portions may then be welded 1306 together to keep the filaments coupled together. In alternative embodiments, welds may be any combination of the previous mesh embodiments.

Figure 17A:
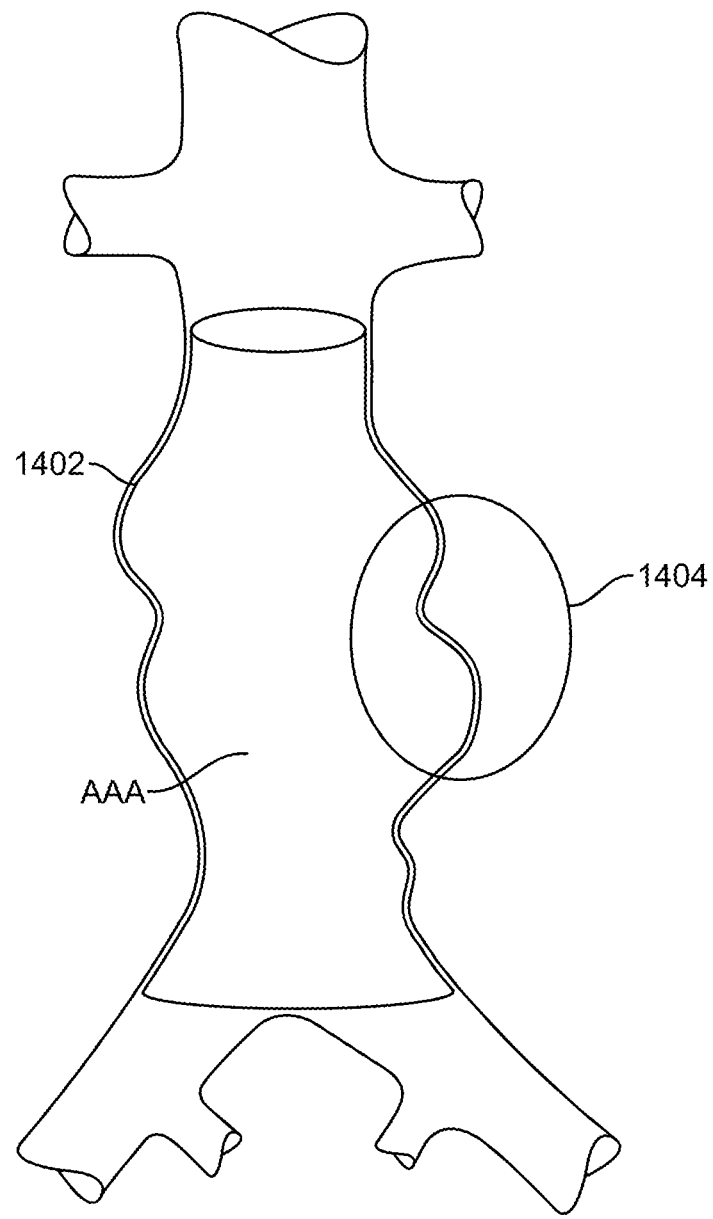
FIGS. 17A and 17B show a prosthesis in accordance with embodiments positioned in the aneurysm.

The structure of the prosthesis is further illustrated by FIGS. 17A through 21B. As shown in FIGS. 17A and 17B, a prosthesis 1402, which may be any of the prostheses disclosed herein, is deployed at its intended location in the aneurysm AAA. The area of the AAA designated as 1404, which may be an area in the vicinity of an SB of the AAA as shown in FIG. 17B, is further described below.

Figure 17B:
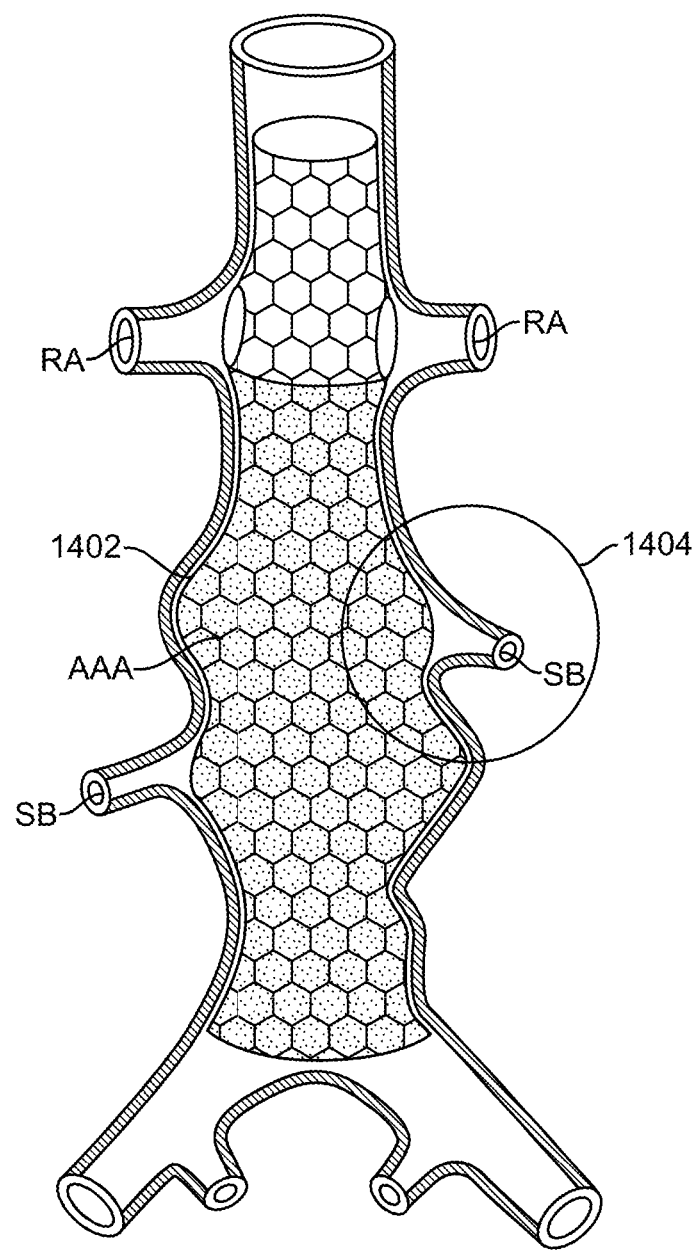
Figure 18:
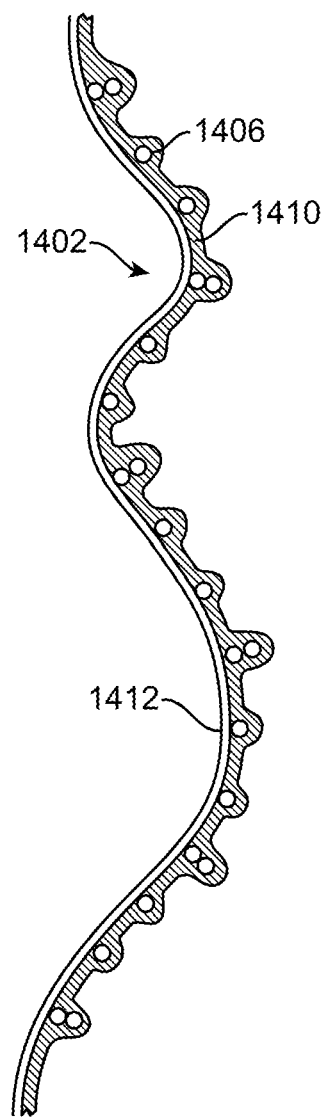
FIG. 18 illustrated an enlarged view of the structure of the prosthesis.

Portion 1404 of prosthesis 1402 of FIG. 17A or 17B is shown in an enlarged view in FIG. 18. Prosthesis 1402 consists of a grid structure made of wires 1406 as described herein. The wire grid is covered by a membrane 1410. The inner (lumen) side of the prosthesis 1402 is covered with a lining 1412. The smooth surface lining 1412 may be made of a low friction bio-compatible material such as teflon, silicone, or a metal film, which allows for smooth flow of blood therepast.

Figure 19:
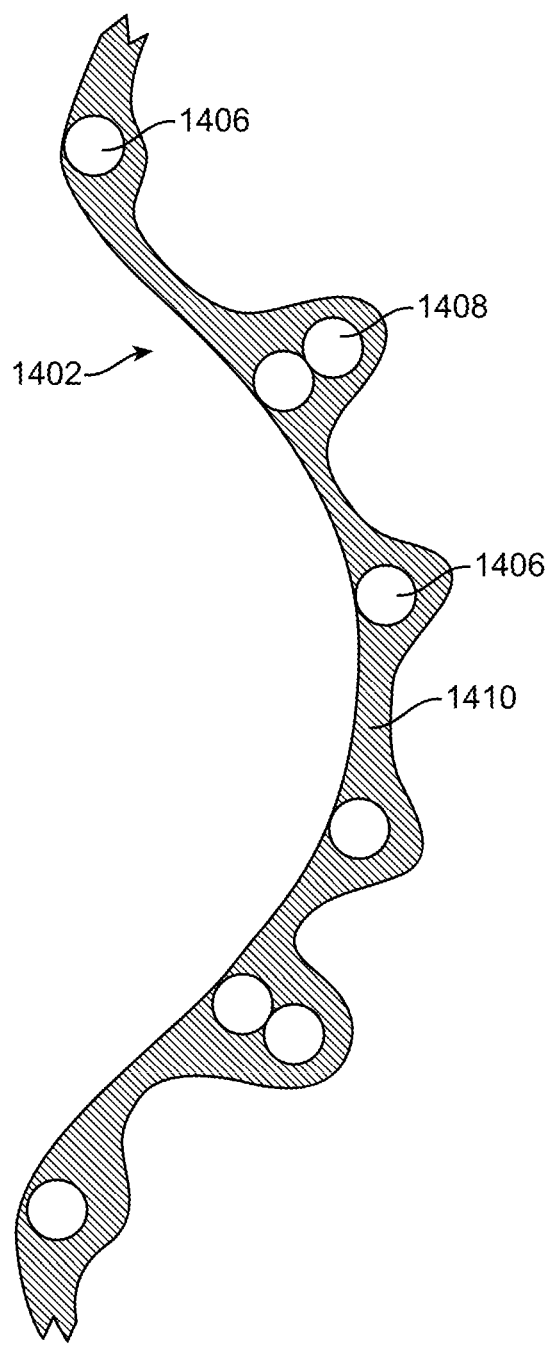
FIG. 19 shows yet further enhanced view of the structure of the prosthesis.

FIG. 19 shows a further enlarged view of a longitudinal section of the structure of the prosthesis 1402. The wires 1406 of the grid are interwoven, such as in a 'chicken wire fence' manner (as described herein), and appear as single wire 1406 or in an overlapping configuration 1408. A membrane 1410 covers the wire grid conformally. As shown in detail in FIG. 19, the inner (lumen) side of the prosthesis 1402 is smooth whereas the outer side of the said prosthesis is textured having a series of peaks and valleys.

Figure 20:
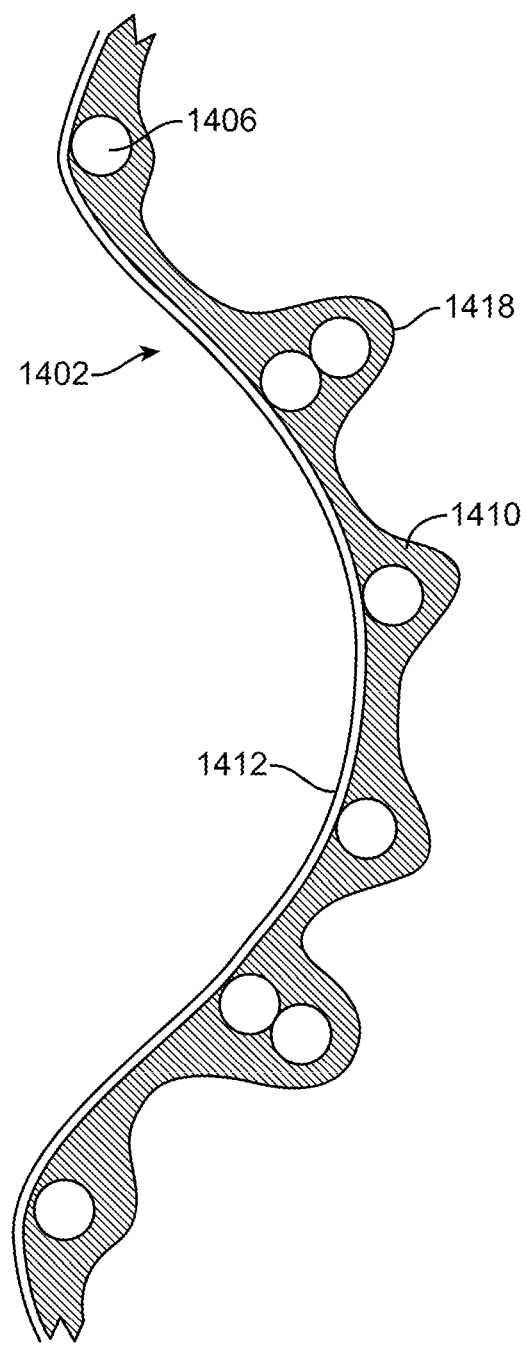
FIG. 20 shows the prosthesis with an inner lining.

Shown further in FIG. 20 in an enlarged view, the inner surface of the membrane covering prosthesis 1402 has been disposed with a lining 1412. The lining constitutes a low friction surface such as Teflon, silicone, metal film or any other suitable bio-compatible material. The lining can be deposited by liquid dipping or spray deposition techniques known in the art. Inner lining 1412 can also be made of a biocompatible, vapor-deposited metal film such as gold or stainless steel. The lining can also be disposed on the outer surface 1418 of the prosthesis 1402. The outer surface 1418 of the prosthesis 1402 is textured on the outside while the prosthesis 1402 has a smooth lining 1412 on the inside. The smooth lining 1412 presents a smooth surface for blood flow. The textured outer surface 1418 helps in the rotational motion as described herein.

Figure 21A:
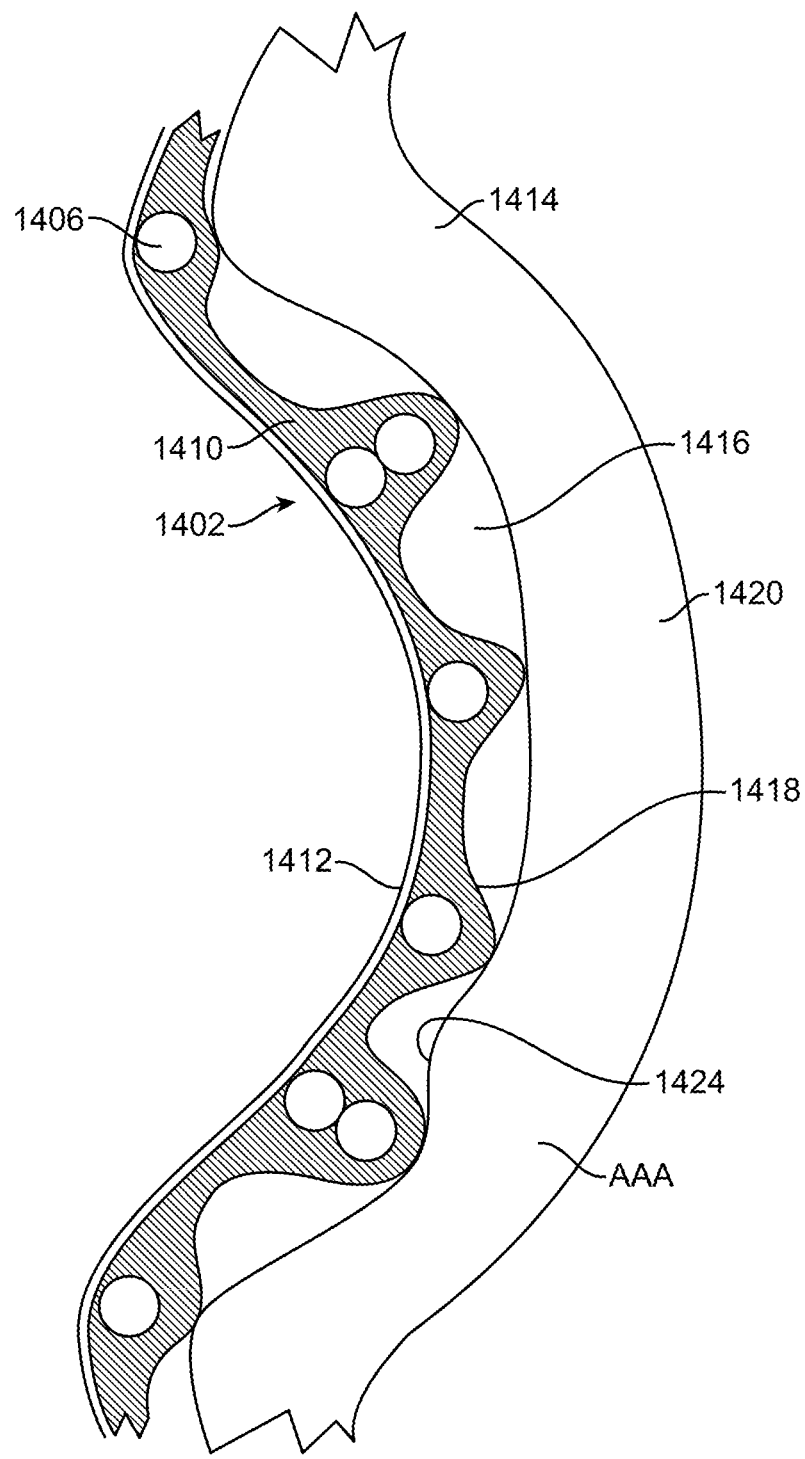
FIG. 21A illustrates, in an enlarged view, the prosthesis appositioned against the inner wall of the aneurysm shown in FIG. 17A.

FIG. 21A shows an enlarged view of the prosthesis 1402 appositioned against the wall 1414 of the blood vessel shown in FIG. 17A. The textured outer surface 1418 of the prosthesis 1402 comes against the inner surface 1424 of the tissue 1420 of the AAA. This action aids in a firmer apposition of the prosthesis 1402 against the tissue 1420 which is a desirable outcome of the deployment of the prosthesis 1402 in the aneurysm AAA. Further, the textured surface creates the interstices 1416 which serve as pockets for the blood to reside in. The trapped blood eventually forms a thrombus thus aiding in the embedding of the prosthesis 1402 against the AAA.

Figure 21B:
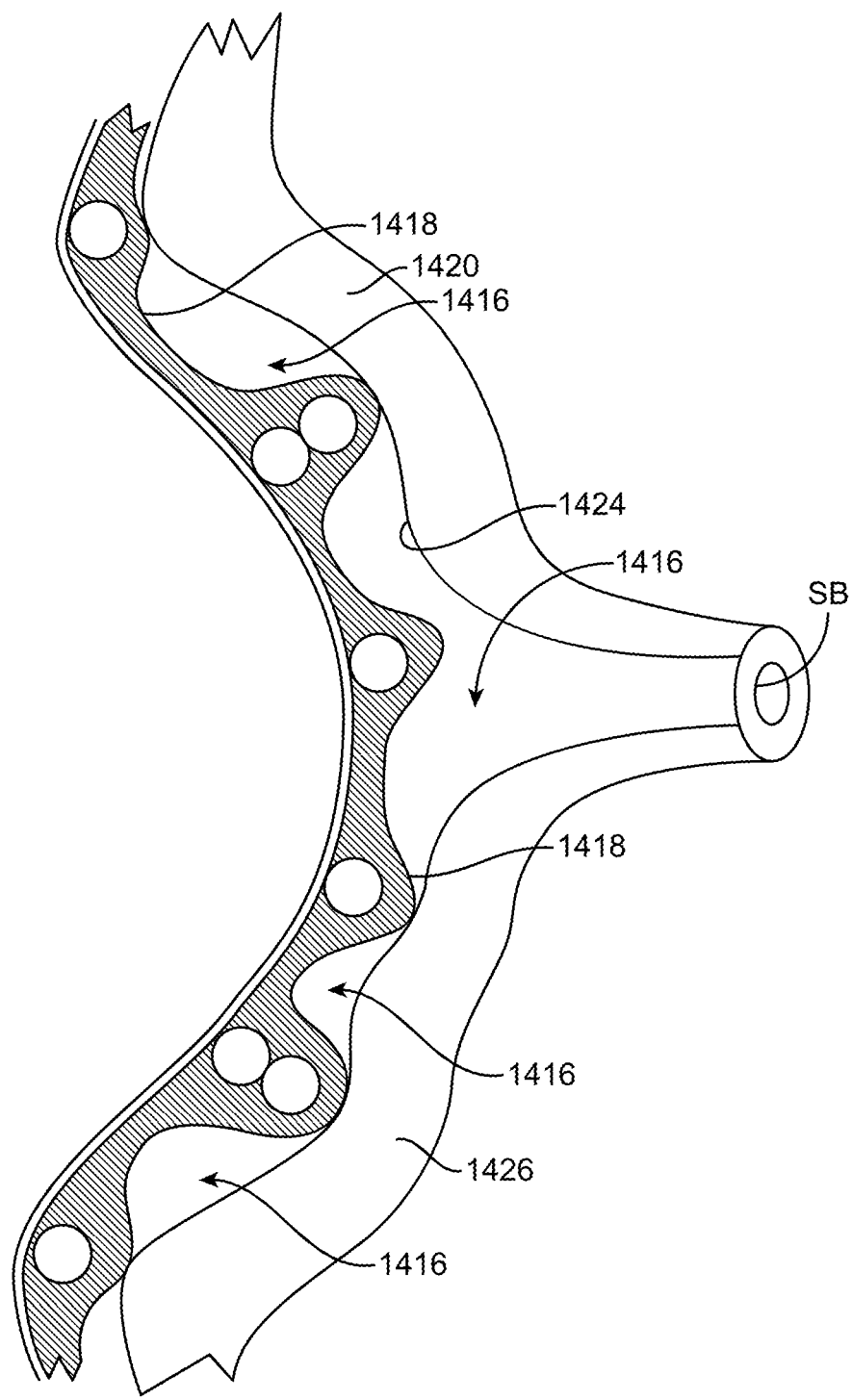
FIG. 21B illustrates, in an enlarged view, the prosthesis appositioned against the inner wall of the aneurysm shown in FIG. 17B.

FIG. 21B shows an enlarged view of the prosthesis 1402 appositioned against the wall 1426 of the blood vessel 1420 shown in FIG. 17B. The textured features of the outer surface 1418 of the prosthesis 1402 are maintained in a firm apposition against the inner surface 1424 of the tissue 1420 of the AAA. In particular, in some cases, the outer surface of the prosthesis can be placed in firm apposition against the ostium of a side branch vessel SB. The firm apposition of the prosthesis 1402 against the inner surface 1424, together with the thrombus formation in the interstices 1416, assures that the blood flow to the side branch SB is blocked. By virtue of this configuration, the condition of type II endoleaks is eliminated.

When the prosthesis 1402 is in conformal contact with the AAA, the aneurysmal pocket 28 as shown in FIG. 2 is eliminated, and blood flow is directed through the lumen of the prosthesis 1402. The membrane 1410 of the prosthesis 1402 is of sufficient strength to withstand the pressure of the flowing blood. The pressure is entirely contained within the prosthesis 1402, and the wall 1426 of the AAA is relieved of the pressure. The AAA is thus stabilized against the force of blood pressure, and the risk of AAA enlargement and eventual vessel rupture is significantly reduced or eliminated.

As described herein, the process of manufacturing the prosthesis involves a sequence of steps which comprise individual tolerances for sizes. For example, the machining and 3D printing processes used in forming the mandrel typically have plus-minus tolerances. As a result of the stack up of various tolerances, the shape of the resulting prosthesis may not completely conform to the shape of the aneurysm. Complete conformity can be important as it may reduce the risk of forming 'pockets' of mismatch between the outer surface of the prosthesis and the inner wall surface of the aneurysm. The pockets can provide the spaces for endoleaks, which are persistent problems with current cylindrical stent grafts is use today. Therefore, it would be desirable to provide a personalized prosthesis which is designed and built to self-adjust in shape to completely and faithfully conform to the inner wall of the aneurysm. Preferably, the personalized prosthesis provides protection of the aneurysm against rupture while eliminating the endoleaks that can result with prior cylindrical stent grafts (e.g., of FIG. 2).

Exemplary embodiments described herein illustrate structures and methods of making the structures wherein the personalized prosthesis is self-adjusting to the shape of the blood flow lumen. This is preferably accomplished by making the prosthesis appropriately oversized with respect to the lumen, and providing a wire twist pattern for the frame of the prosthesis which can self-adjust to the shape of the lumen. The wire frame of the prosthesis can be fabricated from a twist pattern made from the twisting of neighboring wire filaments. As described herein, some ordered, unique patterns can provide the desired properties of self-adjustment when the prosthesis is specifically manufactured for a given aneurysm pocket. The wire frame constituting the personalized prosthesis can be configured to have sufficient hoop strength to maintain firm apposition against the lumen wall. In addition, the wire frame can be configured to have a sufficiently small collapsed profile to make it suitable for containment in a delivery catheter for delivery and deployment in a percutaneous technique.

Figure 22:
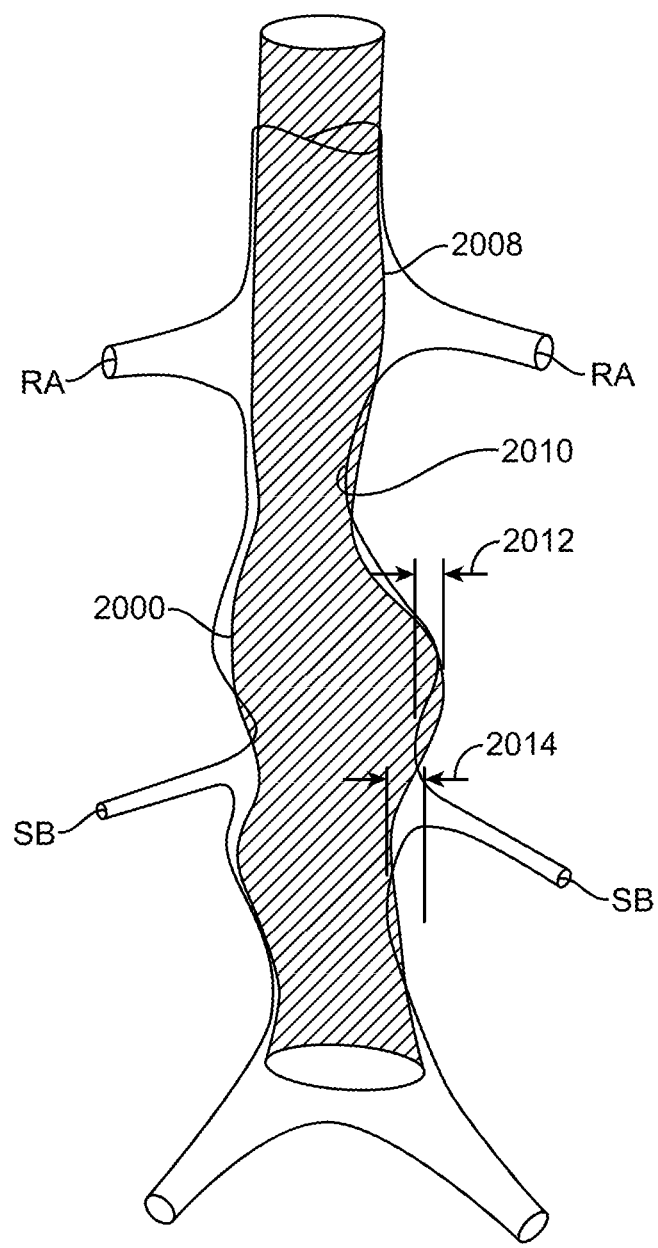
FIG. 22 shows the profile of a mandrel sized and shaped to match the internal geometry of an aneurysm.

FIG. 22 shows the overlay of a mandrel 2008 in a lumen 2000 in an abdominal aortic aneurysm AAA. As described herein, as the CT data are used through the various steps towards the creation of the personalized prosthesis, there is a stack up of tolerances of sequential process steps which results in slight 'mismatches' 2012 and 2014 of the mandrel shape compared to the shape of the lumen of the aneurysm. As a result, the mandrel 2008 has a slightly different shape than the lumen 2000 where the surface of the mandrel 2008 does not perfectly match the lumen shape 2010. The resulting mismatch 2014 in the vicinity of the side branch SB, for example, provides for a potential pocket for the eventual creation of an endoleak.

A solution for overcoming the mismatch due to tolerance stack up is to fabricate a mandrel which is slightly oversized to overcome the mismatch 2014, and to provide a wire frame structure which has the ability to change shape and self-adjust for the mismatches like 2012 and 2014. The resultant prosthesis can have the ability to reduce in size in response to being constrained within a lumen having a smaller size, and thereby self-adjust to the contour of the inner wall of the aneurysm.

Figure 23:
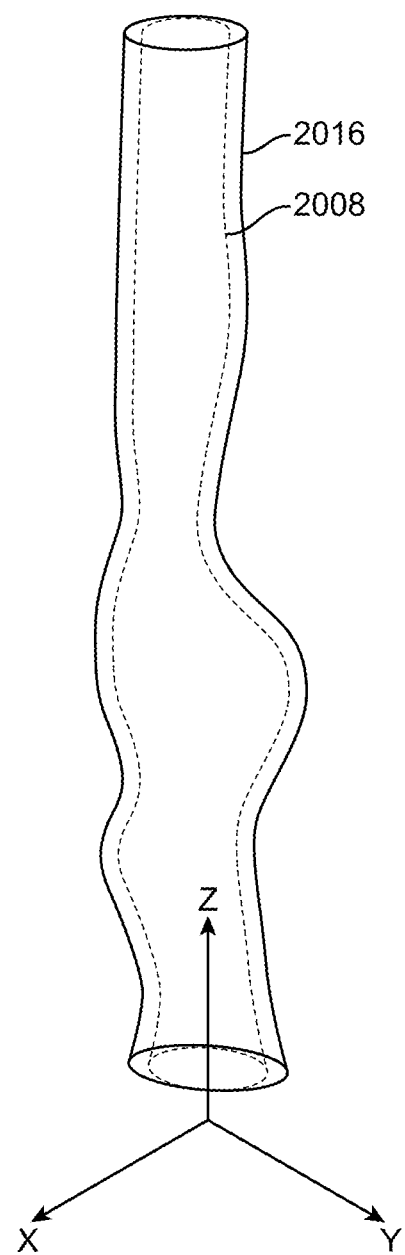
FIG. 23 shows a mandrel oversized relative to the internal geometry of an aneurysm in XY dimensions.

FIG. 23 shows a mandrel 2016 which is slightly larger than the mandrel shape 2008 based on the internal geometry of the aneurysm as determined by the CT scan and the attendant translational tolerance stack up. The mandrel 2016 can be larger only in the x-y direction, and not in the z direction. The mandrel 2016 may have a diameter that is oversized relative to the shape 2008 based on the internal geometry of the treatment site by about 2% to about 40%, about 2% to about 15%, about 5% to about 15%, or about 5% to about 10%. For example, for an aneurysm lumen diameter of 50 mm at a given cross-section, the mandrel may be 55 mm (10% larger) in diameter at that location. The extra 5 mm can be used in adjusting for the mismatches like 2012 and 2014. The oversizing of the mandrel (and therefore the prosthesis) can position the prosthesis firmly against the ostium of the side branch SB thereby eliminating the pocket formed by mismatch 2014 which could give rise to an undesirable endoleak.

Figure 24:
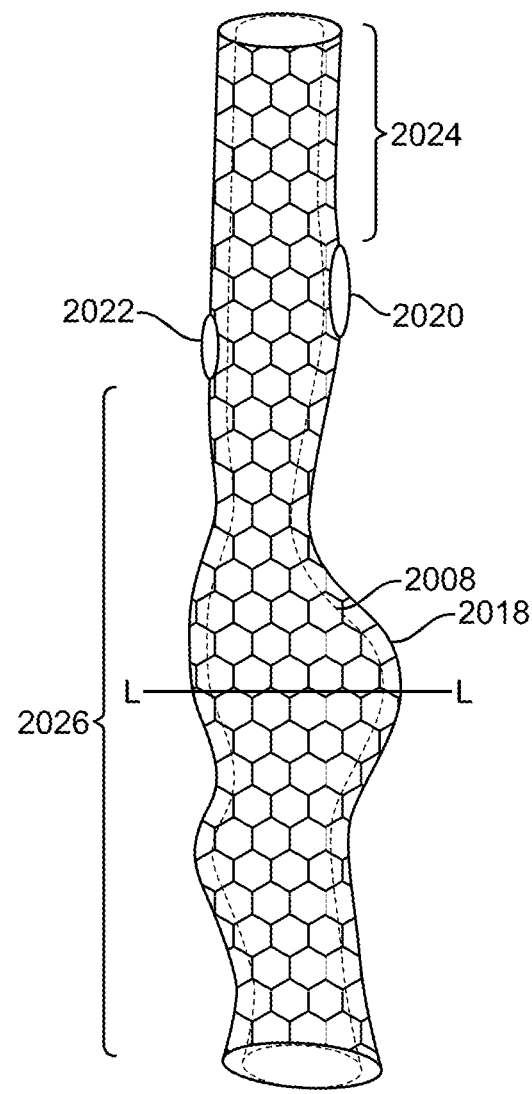
FIG. 24 shows the prosthesis fabricated in accordance with the oversized mandrel of FIG. 23.

FIG. 24 shows an oversized, personalized wireframe prosthesis 2018 conformal to the oversized mandrel 2016. The prosthesis is thus made oversized with respect to the lumen representation 2008. The personalized prosthesis may provide for the apertures or fenestrations 2020 and 2022 corresponding to the renal artery RA ostia, using the data provided by the CT scan as described herein. The inferior portion 2026 of the prosthesis 2018, which is inferior to the renal arteries RA, can be covered with a membrane of a thin plastic material such as teflon, silicone, and the like. The cover or membrane may be only on the inner surface or outer surface of the prosthesis, or it may be on both surfaces. The superior portion 2024 of the prosthesis 2018, which is superior to the renal arteries RA, is preferably not covered with a membrane. The wire frame in the superior portion may be left uncovered. The purpose for this is so that, over time, the wire frame gets embedded in the endothelial lining of the aortic lumen. This action can further secure the prosthesis in the aneurysm.

FIGS. 25A to 25G show various wire twist patterns which can be used for fabricating the wire frame of the prosthesis. By way of terminology, a 'twist' is a pattern where two neighboring wire filaments are wound against each other. A 'loop' is defined as one wind of the neighboring wires.

Figure 25A:
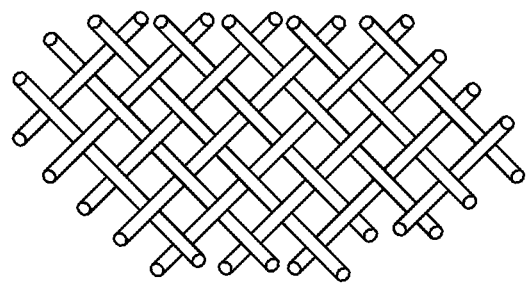
FIGS. 25A to 25F show various wire twist patterns.

FIG. 25A shows a pattern where the neighboring wires cross over each other. In this case the wires do not form a loop. The result is a braided structure which is of a cylindrical shape. This structure may not be suitable for percutaneous deployment in the aneurysm because that the structure can elongate substantially when confined inside a slider tube of the delivery catheter. In addition, its hoop strength may not sufficient to be effective in maintaining a firm apposition of the prosthesis against the aneurysm lumen.

Figure 25B:
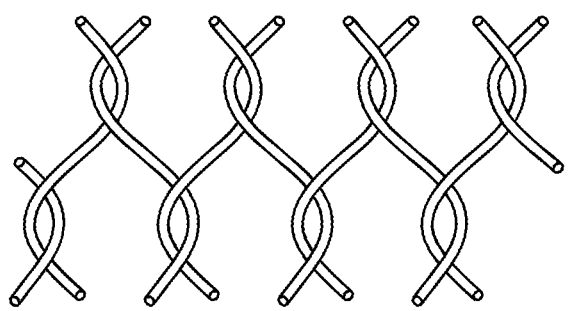

FIG. 25B shows a twist pattern in which two neighboring wires are wound against each other once to form one loop. The entire prosthesis is made from these single loops. This pattern also has relatively poor hoop strength and may not be suitable for making an effective functional prosthesis.

Figure 25C:
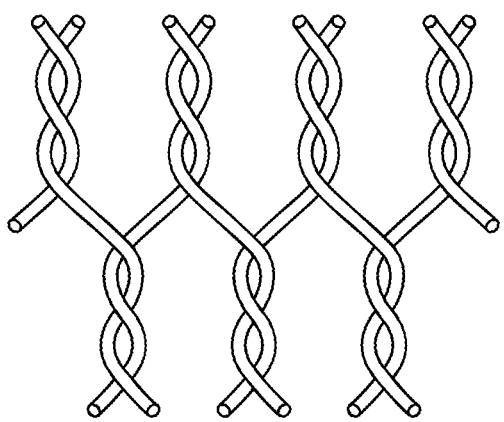

FIG. 25C shows a twist structure involving two loops formed by winding of the two neighboring wires. The prosthesis made from this pattern of two loops also has relatively poor hoop strength, and therefore may not be suitable for a functioning prosthesis.

Figure 25D:
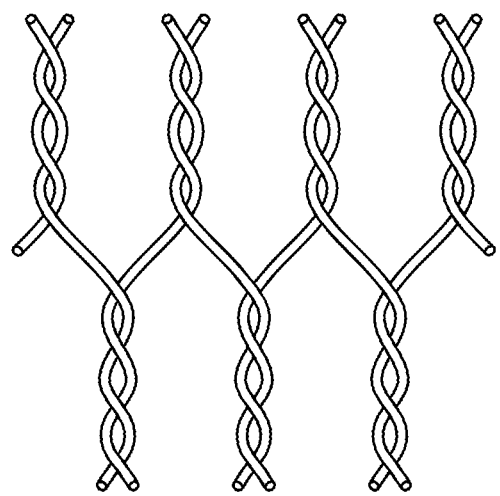

FIG. 25D shows a twist pattern which employs three loops of neighboring wires. This structure has better hoop strength, but when collapsed, it forms a relatively larger profile, for example compared to the structures of FIGS. 25A-25C. Also, it does not have the ability to self-adjust for any shape mismatch, as described further herein.

Figure 25E:
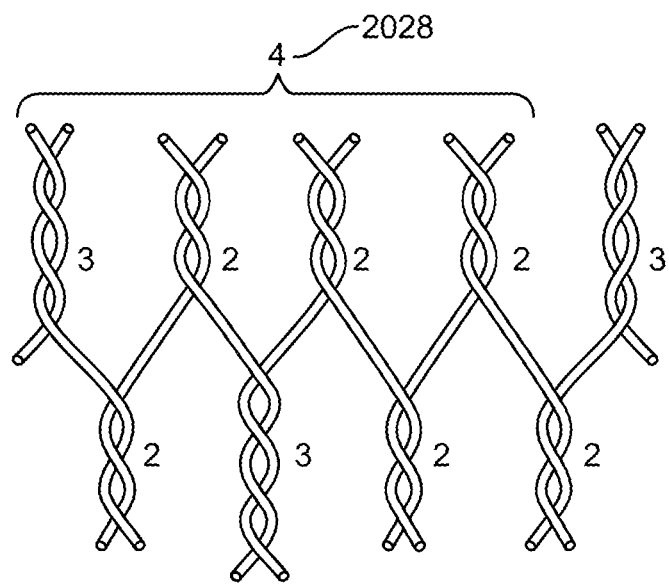

FIG. 25E shows a preferred embodiment of the present wire pattern. The twist pattern consists of a combination of two and three loops of neighboring wire filaments. More specifically, the pattern has a combination of one twist of three loops, followed by three two-loop twists, forming a group of four twisted wire pairs in a 3-2-2-2 loop configuration. Then the group of the four twist pattern repeats along a cylindrical locus. This pattern is termed as "41". The first digit, namely, "4" refers to the pitch count of the twists, and the second digit, namely, "1" refers to the twists which have three loops. Thus a 41 pattern has a pitch 2028 of four (4) twists where one (1) twist has three loops and the remaining three twists have two loops, also described as a "3222" pattern. In this nomenclature, pattern shown in FIG. 25D would be termed as "44", where the pitch consists of four (4) twists, and all four (4) twists have three loops each.

It is important that, in order to obtain the best functional prosthesis, the pitch 2028 of four (4) twists be offset by at least one twist in the next cylindrical locus as shown in FIG. 26E. Similarly, the next circumferential twist pattern will be shifted to the right by one twist.

Figure 25F:
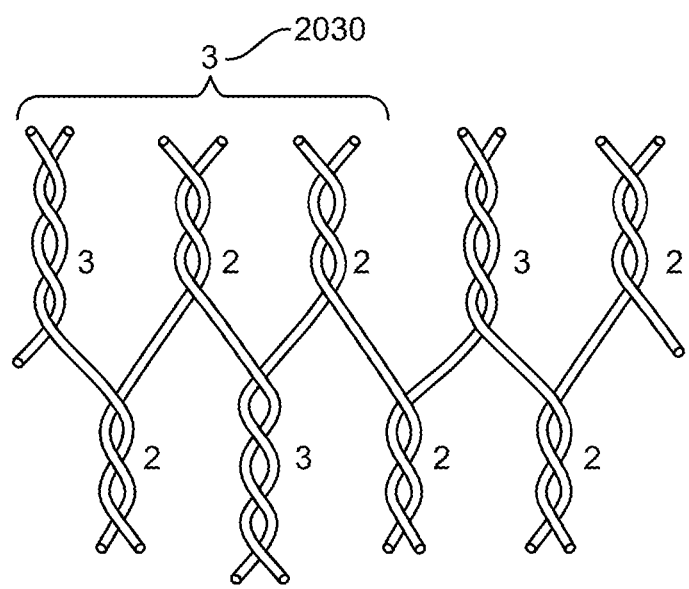

FIG. 25F shows a twist combination which, in the above nomenclature, is termed a "31". It has a pitch 2030 of three (3) twists. Of this, one (1) twist consists of three loops and the following two twists consist of two loops each, forming repeating groups of three twisted wire pairs in a 3-2-2 loop configuration.

We have fabricated more than 100 patterns of various combinations and tested the resulting hoop strength as well as the ability of the wire frames to self-adjust. The "41" pattern was found to be optimal in terms of hoop strength, ability to self-adjust in shape, and ability to be confined into a sufficiently small delivery system suitable for percutaneous delivery and deployment of the prosthesis in the aneurysm space. Optionally, the prosthesis may comprise two or more regions having different wire frame patterns, such that the two or more regions have different hoop strengths and/or ability to self-adjust to different extents. For example, a prosthesis may be formed to have variable hoop strength along a longitudinal axis of the prosthesis, by having wire frame patterns of various hoop strengths arranged along the longitudinal axis.

Figure 26:
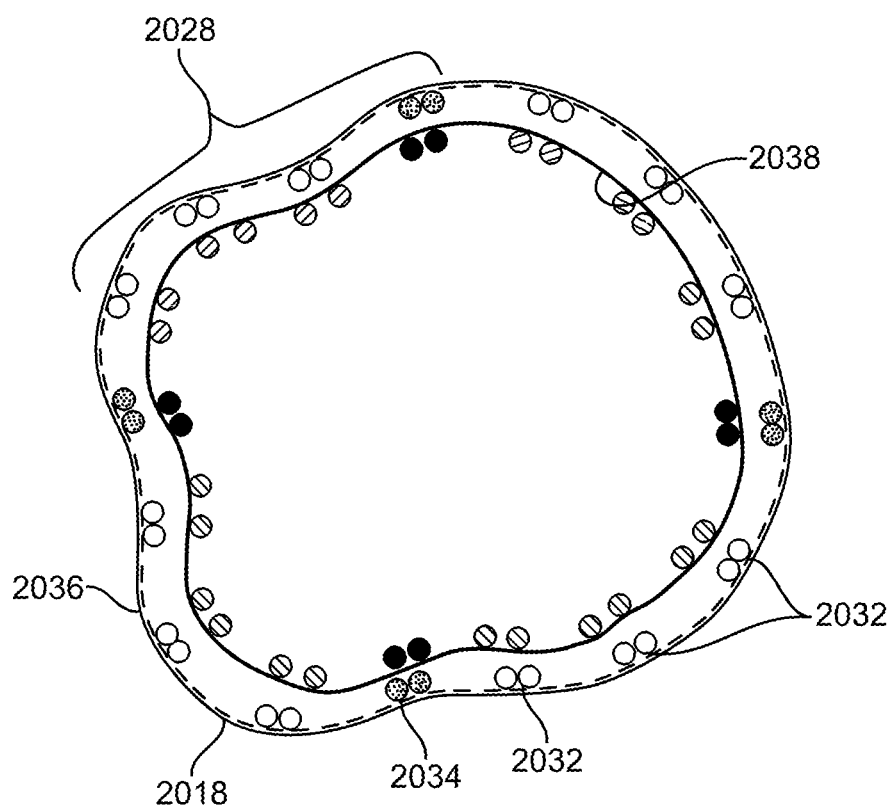
FIG. 26 shows the preferred 41 twist pattern of a prosthesis in a cross section of the lumen.

FIG. 26 shows a cross-sectional view of prosthesis 2018 along the line LL of FIG. 24. By way of example, the prosthesis 2018 consists of 32 filament wires forming 16 nodes. The prosthesis also consists of a membrane 2036. In free space, the loops are tightly wound against each other. Nodes 2032 consists of a two-loop twist, and nodes 2034 consists of a three-loop twist. The 16 nodes are divided into four pitches 2028 of four twists each. The lumen of the aneurysm is depicted as 2038. As seen in this figure, the prosthesis 2018 in its free space configuration is larger in size than the lumen 2038. As described herein, the prosthesis 2018 can be fabricated to be larger than the lumen 2038 into which the prosthesis is to be delivered. When the prosthesis is deployed in the lumen, the loops of the twists can automatically adjust in response to confinement within the lumen 2038 having a circumference smaller than that of the prosthesis 2018.

Figure 27A:
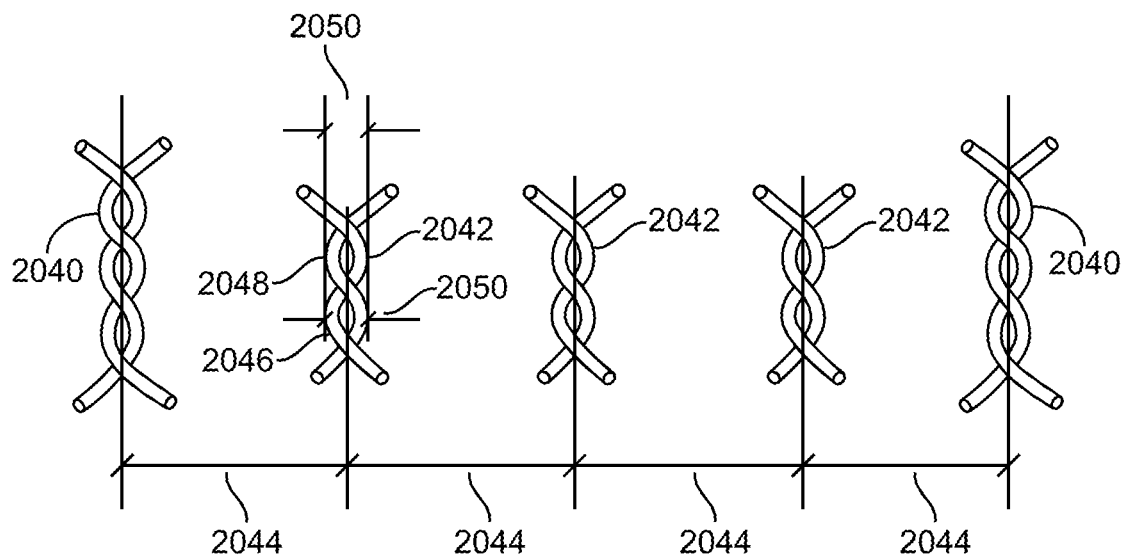
FIGS. 27A and 27B show the adjustment made by the loops of the twists in response to being confined to a smaller space within a lumen.
Figure 27B:
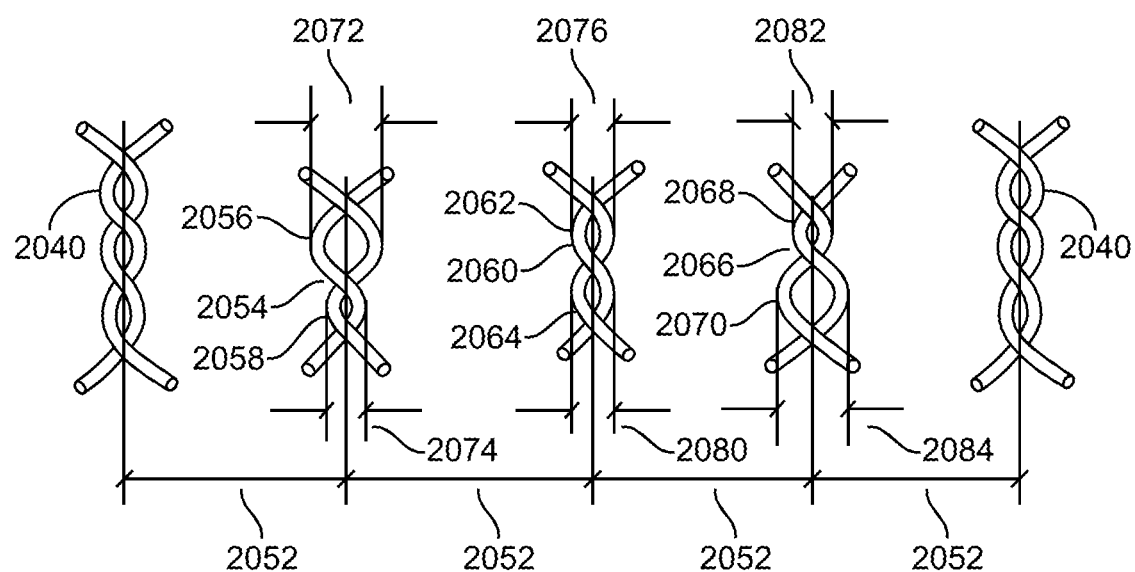

FIGS. 27A and 27B show the details of the adjustment of the loops of a given twist in response to being confined to a smaller circumference. FIG. 27A shows the 41 pattern of the prosthesis in free air. The three-loop twists 2040 are locked against each other by virtue of its construction, but the two-loop twists 2042 are free to move the loops relative to each other. As the prosthesis is deployed in the smaller space of the lumen, the two-loop twists 2042 adjust by opening up against each other. In free space, the distance 2044 between the adjacent twists is shown in FIG. 27A. The two-loop twists have loops 2046 and 2048. Even though the wire filaments are tightly wound around each other, the outer edges of the wire filaments are distance 2050 apart from each other. FIG. 27B shows the configurations of the loops of the twists as the prosthesis 2018 is deployed in the smaller confines of the lumen. The distance 2052 between the adjacent twists is now correspondingly smaller than the free-air distance 2044. The first two-loop twist 2054, adjacent to the three-loop twist 2040, consists of an upper loop 2056 and a lower loop 2058. The second two-loop twist 2060, disposed in the middle between two adjacent two-loop twists, similarly consists of the upper loop 2062 and a lower loop 2064. The third twist 2066 consists of an upper loop 2068 and a lower loop 2070. When the prosthesis 2018 having the free-air distance 2044 between adjacent twists, as shown in FIG. 27A, is deployed in the smaller confines of the lumen 2038, loops of the twists make the appropriate adjustments, resulting in the smaller distance 2052 between adjacent twists as shown in FIG. 27B.

The adjustments of the loops of the twists may be symmetrical. For example, as shown in first two-loop twist 2054 of FIG. 27A, the upper loop 2056 may open up to an inter-wire spacing of 2072, while the lower loop 2058 stays at an inter-wire spacing 2074 of a tight twist (same as the inter-wire spacing 2050 of the loops in the free space configuration, shown in FIG. 27A). As shown in the second or middle twist 2060, both the upper loop 2062 and the lower loop 2064 may open up to substantially equal inter-wire distance of 2076 and 2080, which may be greater than the inter-wire distance 2050 of the loops in the free space configuration. Finally, as shown in the third twist 2066, the upper loop 2068 may remain closed to an inter-wire distance of 2082 (same as the tight wound twist 2050 of free space configuration), while the lower loop 2070 may open up to a spacing 2084 greater than the inter-wire distance 2050 of the loops in the free space configuration. The loops of three-loop twists 2040 adjacent the two-loop twists 2074, 2080, and 2084 may not open up, remaining tightly wound.

The difference between the inter-twist distance 2044 in the free space configuration and the inter-twist distance 2052 in the lumen-confined configuration may be accounted for by the increase in the inter-wire spacings 2072, 2076, and 2084 when the loops of the two-loop twists open up. The extent to which a loop of a two-loop twist opens may be limited by the locking of one of the two loops while the other loop opens up to a finite distance. This limit in the extent to which the loops can open in turn places a lower limit on the diameter of the prosthesis to which the wire mesh can self-adjust. Such a limit in the extent to which the prosthesis can self-adjust to a smaller diameter can be advantageous, as the prosthesis needs to maintain an appropriate hoop strength to provide firm apposition of the prosthesis against the aneurysm wall. The cross-over pattern of FIG. 25A or the single-loop twist frame of FIG. 25B provide no definite limit or insufficient limit to the decrease in prosthesis diameter, as these two patterns do not have a 'locking' loop. Conversely, the three-loop twist of the 44 configuration, as shown in FIG. 25D, does not allow for the opening of the loops as all three loops are tightly wound against each other. Thus a hybrid configuration such as the 41 configuration shown in FIG. 25E (3-2-2-2 loop twists) can provide for the optimal configuration for the fabrication of a preferred structure of a self-adjusting effective prosthesis. This prosthesis can self-adjust against tolerance variations in spacing while providing the necessary hoop strength to maintain firm apposition against the aneurysm lumen wall to prevent endoleaks and reduce or eliminate the risk of vessel rupture.

The two-loop twists open up along the circumferential plane for necessary self-adjustment needed to accommodate the size differential between open air and confined configurations of the prosthesis. Therefore, the mandrel need be made larger only in the circumferential plane (x-y plane of the FIG. 23). The mandrel may be oversized by a fixed percentage in all dimensions, or by varied percentages in different dimensions. A prosthesis made from a mandrel which is oversized in all dimensions will not have complete conformity as it does not have any mechanism to accommodate for the size differential in the z direction.

Figure 28:
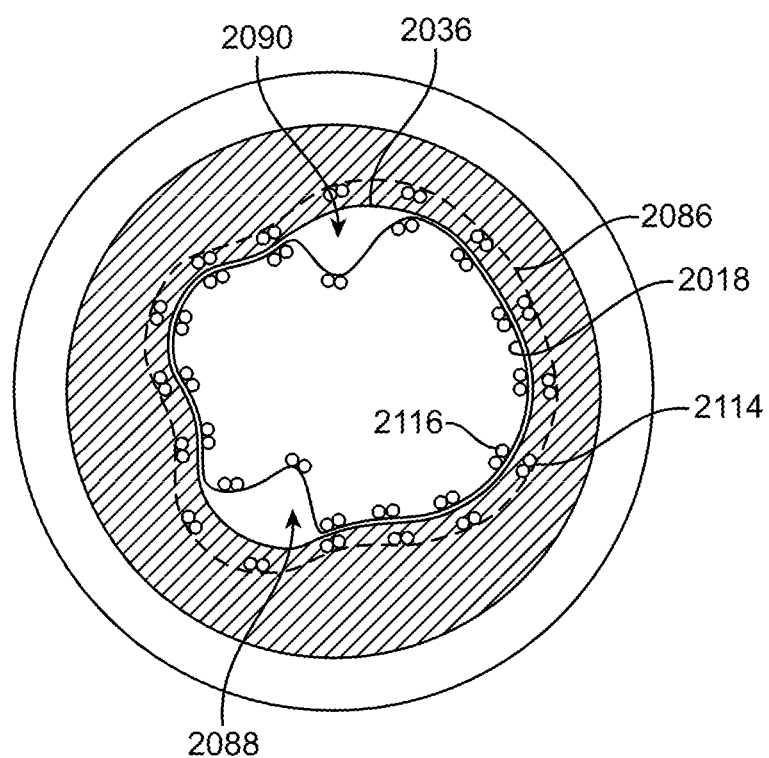
FIG. 28 shows an oversized 44 pattern deployed in the lumen is a cross-section view.

FIG. 28 shows the deployment of a 44 (3-3-3-3 loop twists) structure prosthesis 2018 in the lumen 2036. The dotted line configuration 2086 represents the prosthesis 2018 in free space. Since the three-loop twists 2114 do not do not allow for the opening of the loops, they remain tightly wound in a manner 2116. As a result, the prosthesis is forced to buckle up at one or more locations, forming bucked spacings 2088 and 2090 to accommodate the smaller confines of the lumen 2036. This is an undesirable configuration of the deployed prosthesis as the buckled spacings 2088 and 2090 allow for blood flow channels giving rise to potential endoleaks. In addition, the conformity of the prosthesis 2018 against the lumen 2036 is compromised.

Figure 29:
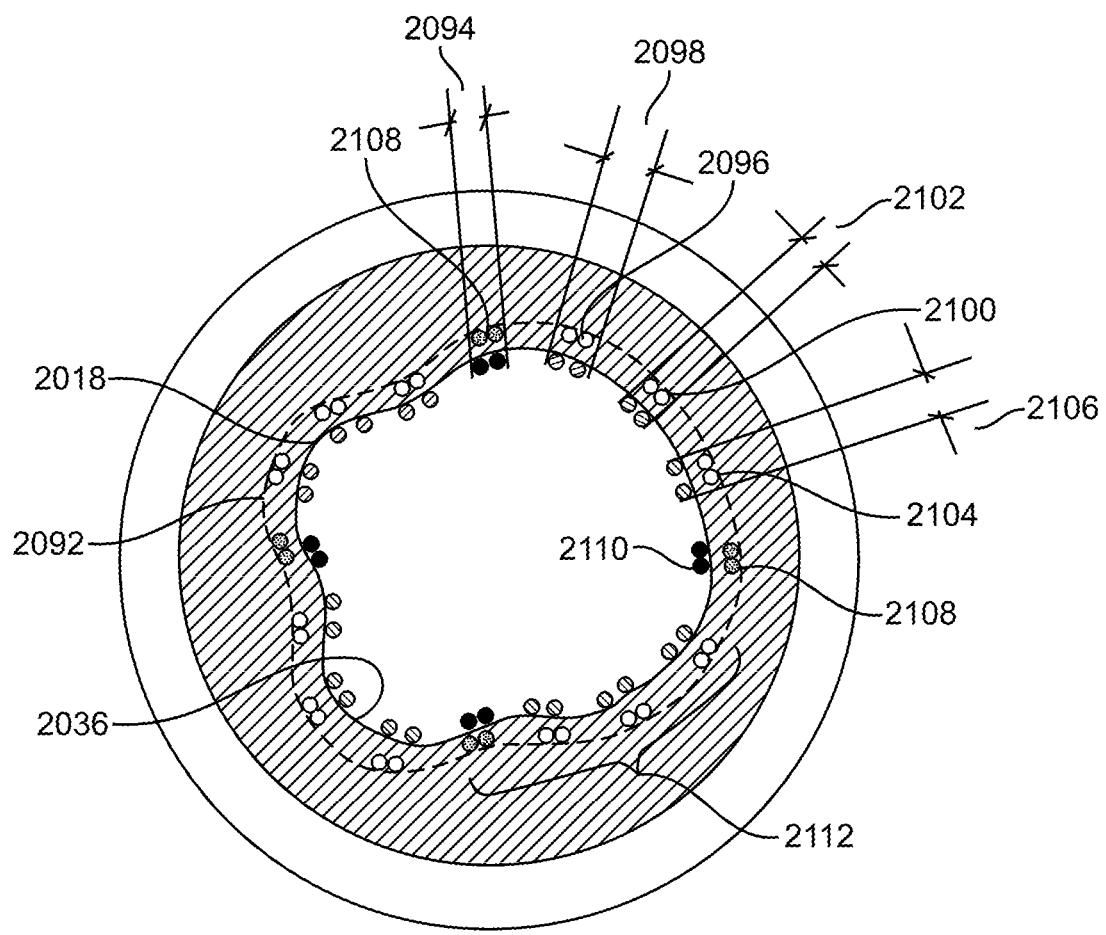
FIG. 29 shows the oversized 41 pattern deployed in the lumen in a cross-section view.

FIG. 29 shows the prosthesis 2018 of 41 (3-2-2-2 loop twists) pattern deployed in the lumen 2036. The free space shape 2092 of the prosthesis is shown in a dotted line configuration. Prosthesis 2018 self-adjust to a smaller space 2036 of the lumen by allowing the individual twists of two loops to open up to accommodate the corresponding reduction in the circumferential dimension. In the free space configuration 2092, all the wire twists are tightly wound and are in close proximity to each other as depicted by twist 2108 having an inter-wire distance 2094. In the lumen-confined configuration of prosthesis 2018, the three two-loop twists 2096, 2100, and 2104 open up in an asymmetrical fashion or in a symmetrical fashion as described in detail with reference to FIG. 27B. First, the upper loop of the first two-loop twist 2096 opens up to an inter-wire spacing of 2098. Next, both loops of the second two-loop twist 2100 open up to an inter-wire spacing of 2102. Last, the lower loop of the third two-loop twist 2104 also opens up to an inter-wire spacing of 2106. The next twist 2108 consists of three loops, and as explained herein, it remains tightly wound in a manner 2110. This symmetrical pattern may repeat for the next set 2112 of four 3-2-2-2 loop twists.

The prosthesis 2018 of a 41 configuration can thus maintain its conformal apposition against the lumen 2036, by self-adjusting to closely match the shape and circumferential dimensions of the lumen when deployed. The self-adjusting nature of the prosthesis can provide improved protection against endoleaks and hence risk of vessel rupture, compared to configurations that do not allow substantial self-adjustment of the prosthesis shape and dimensions (e.g., the prosthesis of a 44 configuration as shown in FIG. 28).

Figure 30:
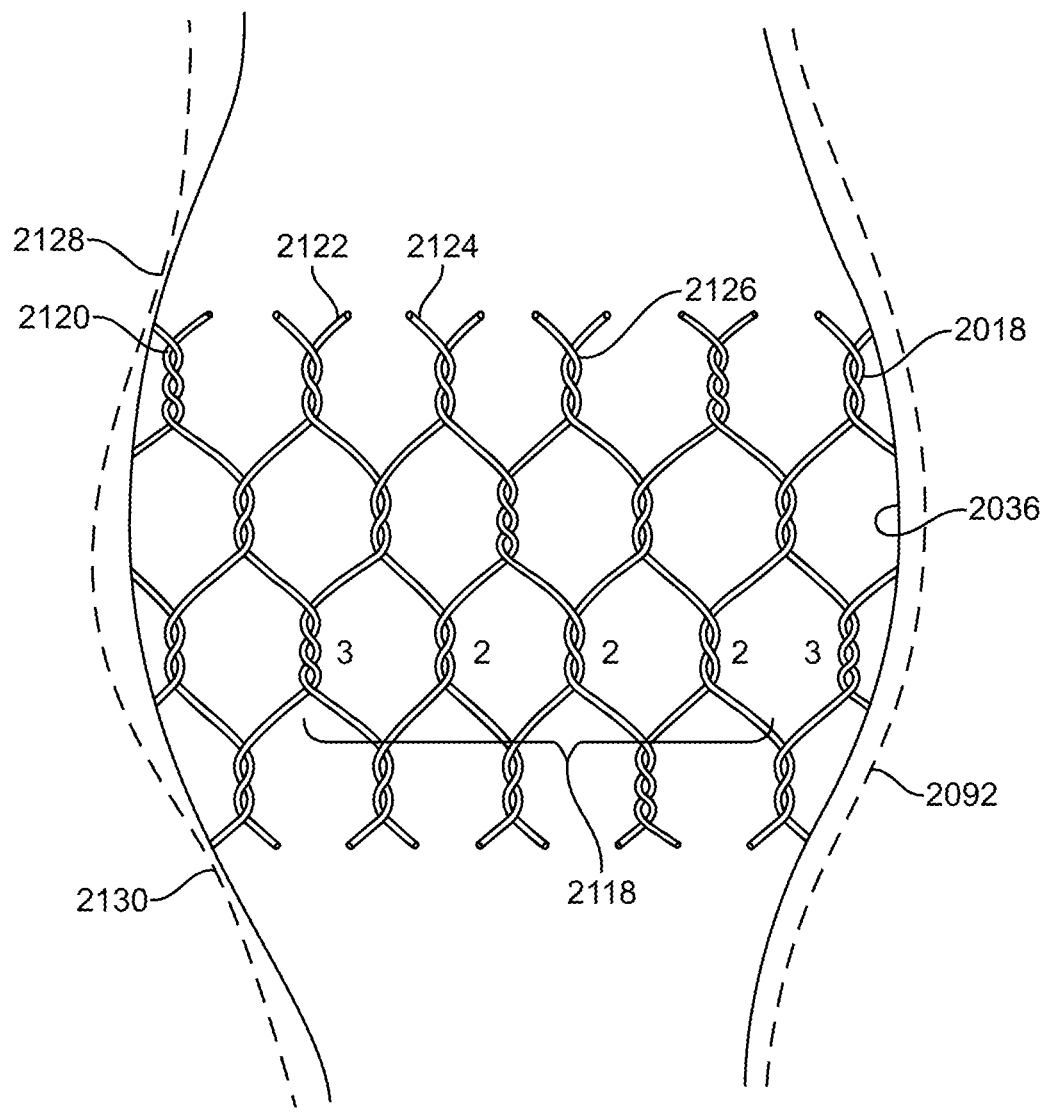
FIG. 30 shows the 41 twist pattern adjusting to a smaller confinement of a lumen.

FIG. 30 shows the prosthesis 2018 of a 41 configuration (3-2-2-2 loop twists) deployed in the lumen 2036. The free space configuration of the said prosthesis is shown as 2092. The individual adjustments of the twists are shown. The repeat pattern 2118 is made of a set of 3-2-2-2 loop twists. The first twist 2120 consists of three loops and does not open up substantially in response to the prosthesis being confined to a smaller space of the lumen. Next, the first two-loop twist 2122 adjusts such that the upper loop of the said twist opens up while the lower loop remains tightly wound. The second two-loop twist 2124 has both loops opened, and the third two-loop twist 2126 has the lower loop opened up while the upper loop of this twist remains tightly wound. This pattern repeats for the next set of four twists. The opening of the two-loop twists accommodates automatically as needed to the confines of the lumen.

The opening of the loops may not be symmetrical in all cases. For example, in a situation where there may not be a large mismatch, as shown at locations 2128 and 2130, the opening of the two-loop twists may be somewhat random, but sufficient to account for the self-adjustment.

Figure 31:
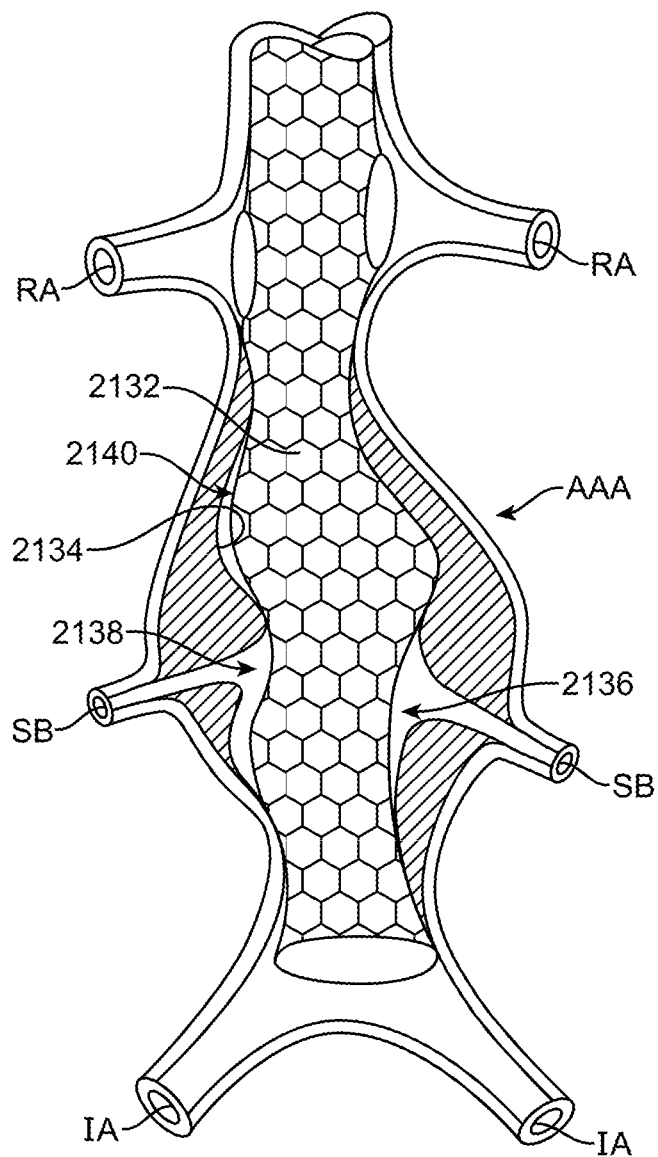
FIG. 31 shows a deployment of a regular (non-oversized) prosthesis in the aneurysm.

FIG. 31 shows the placement of a personalized or custom-shaped prosthesis 2132 in an AAA, the prosthesis made to specifications provided by the corresponding CT scan without any oversizing. Such a prosthesis may be fabricated from the non-oversized mandrel 2008 of FIG. 22. As the prosthesis 2132 is deployed in the AAA, the apposition of the prosthesis 2132 against the lumen wall 2134 may not be optimal, forming pockets of mismatch 2136, 2138, and 2140 at which locations the circumferential dimension of the non-oversized prosthesis 2132 is smaller than the circumferential dimension of the lumen wall 2134. Because the prosthesis as described herein is manufactured in its maximally expanded configuration, the non-oversized prosthesis is unable to expand any further when deployed to accommodate the spacings between the fully-expanded prosthesis and the lumen. These pockets are undesirable in the sense that they can provide for the leak of blood into the pockets. For example, the pocket 2136 in the vicinity of the ostium of the side branch SB can be a location for an endoleak to develop. The result of the endoleak is that the aneurysmal pocket keeps on enlarging, thereby increasing the risk of an aneurysm rupture.

Figure 32:
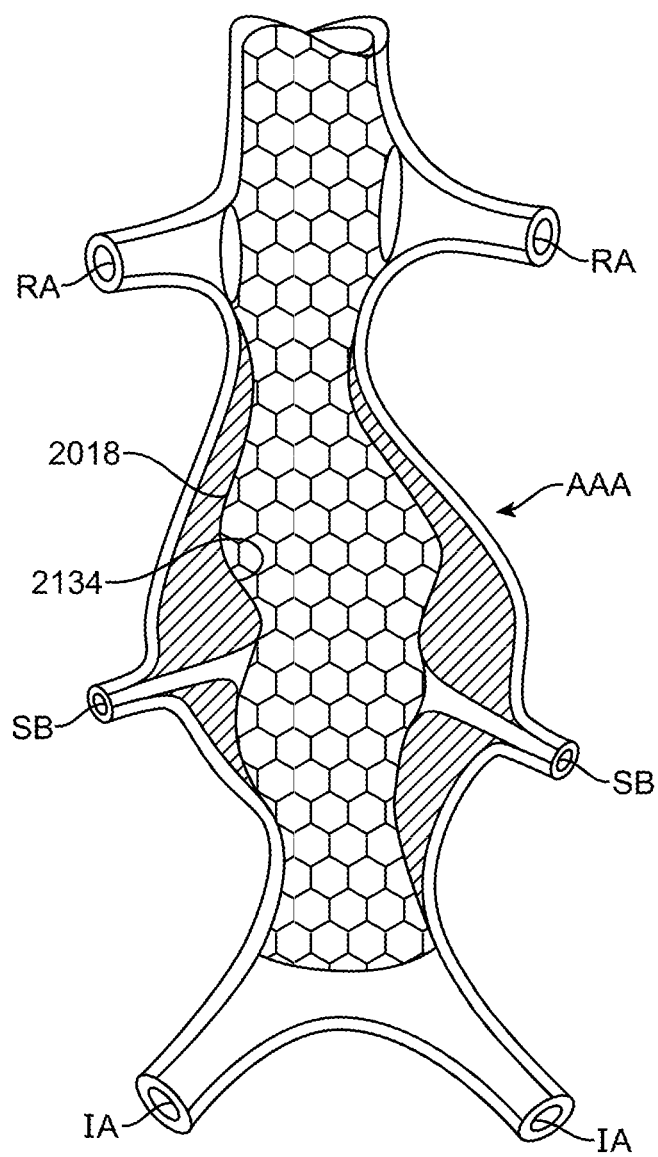
FIG. 32 shows the oversized prosthesis conformally appositioned in the aneurysm showing the details of the self-adjustment of the twist loops.

FIG. 32 shows the deployment of the oversized, self-adjusting personalized prosthesis 2018 in the AAA. As described herein, this design and construction of the prosthesis can provide complete conformal apposition of the prosthesis against the wall of the lumen 2134, by enabling self-adjustment of the shape and dimensions of the prosthesis to match the shape and dimensions of the lumen. The oversizing of the circumferential dimensions of the prosthesis eliminates pockets of mismatch wherein the prosthesis is smaller than the lumen. Instead, in locations of mismatch between the prosthesis and the lumen, the dimensions of the prosthesis in its free-space configuration are now greater than the dimensions of the lumen, and the prosthesis is able to self-adjust at these locations by virtue of the opening of twist loops as described herein. The pockets of mismatch shown in FIG. 31, which can potentially lead to the development of endoleaks, are now eliminated or minimized, by the adjustment of the wire frame structure of the prosthesis to accommodate the exact geometry of the lumen. Thus, a more definitive treatment for the containment of the aneurysm is delivered.

While the functionality and use advantages of the oversized, self-adjusting personalized prosthesis are described herein primarily in reference to a 41 (3-2-2-2 loop) twist configuration, the oversized personalized prosthesis may comprise any appropriate wire frame construction that allows for the self-adjustment of prosthesis shape and dimensions. For example, an oversized prosthesis comprising a 31 (3-2-2 loop) twist configuration, as shown in FIG. 26F, can also serve as an effective, self-adjusting implant. In addition, any other combination of three-loop twists together with zero (i.e. braid), one, or two loop twists can also work for the intended oversized prosthesis. A twist network solely comprising three or more loops may have no or limited ability to adjust in size, and a prosthesis made of such a twist network would therefore have no or limited ability to self-adjust to the more confined space of a lumen. Numerous prostheses having various wire frame constructions have been fabricated and analyzed, and of the constructions studied, an oversized prosthesis made in a 41 configuration as described herein was shown to have the best attributes of self-adjustment, hoop strength, and apposition conformity, while having an acceptably small collapsed profile suitable for percutaneous delivery and deployment in the aneurysm.

The self-adjusting attribute of an oversized personalized prosthesis as described herein is also advantageous in maintaining complete apposition of the prosthesis against the tissue in a dynamic situation, such as during systolic and diastolic conditions of pulsatile blood flow. During the systolic part of the pulsatile cycle, the blood pressure in the aneurysm lumen is higher and the resulting diameter of the aneurysm lumen is larger. Conversely, during the diastole, the pressure of blood is lower resulting in a smaller lumen size. These dynamic variations can be automatically accommodated for by the built-in attribute of self-adjustment of the prosthesis.

FIGS. 33A-33F illustrate an exemplary method of delivering a personalized prosthesis that is fabricated to match the patient's anatomy at the treatment site, as described herein. The personalized prosthesis is preferably fabricated using the methods described herein. This exemplary method is directed at treatment of an aortic aneurysm, but could also be used to treat aneurysms in other parts of the body such as a cerebral aneurysm, or other body cavities such as a stomach, bladder, etc. The method could also be used to treat normal or presymptomatic tissue of a patient at risk of developing an aneurysm or at early stages of development of an aneurysm.

FIG. 33A illustrates an infrarenal aortic aneurysm AA in a portion of the aorta inferior to the renal arteries R. In this embodiment, the aneurysm does not extend into the iliac arteries I, external iliac arteries EI, internal iliac arteries II, or femoral arteries F. Thus, in this case the repair of the prosthesis does not need to extend past the aortic bifurcation into the iliac arteries I. However, in a situation where the diseased or damaged tissue extends past the aortic bifurcation, a similarly personalized prosthesis may be fabricated using similar methods described above. The prosthesis may be a single piece or it may be modular and assembled in situ. In FIG. 33B a standard guidewire GW is inserted by surgical cutdown or percutaneously (e.g. using the Seldinger technique) into a femoral artery and then advanced so that the distal tip of the guidewire is positioned beyond the location of the aneurysm.

Figure 33F:
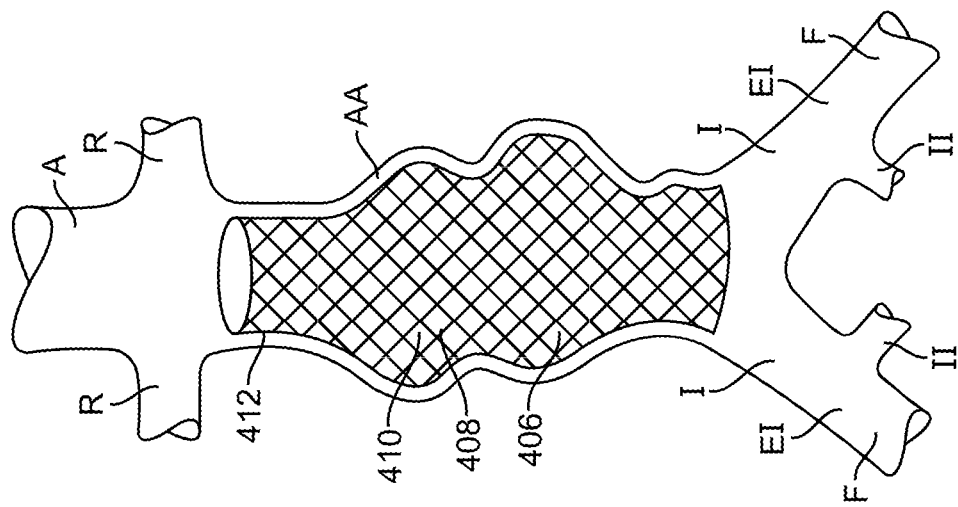
Figure 33E:
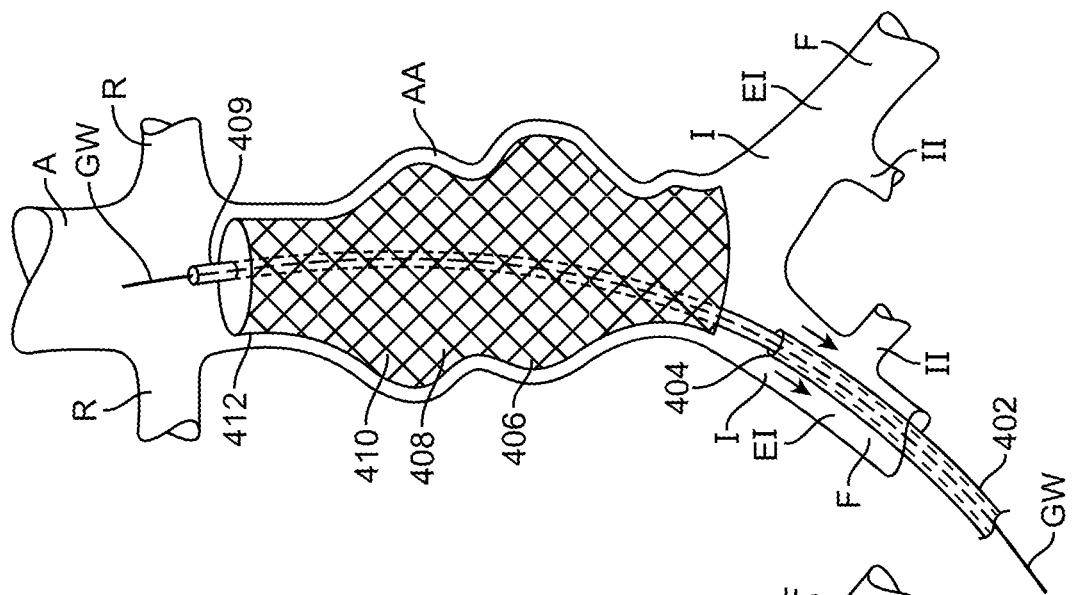
Figure 33D:
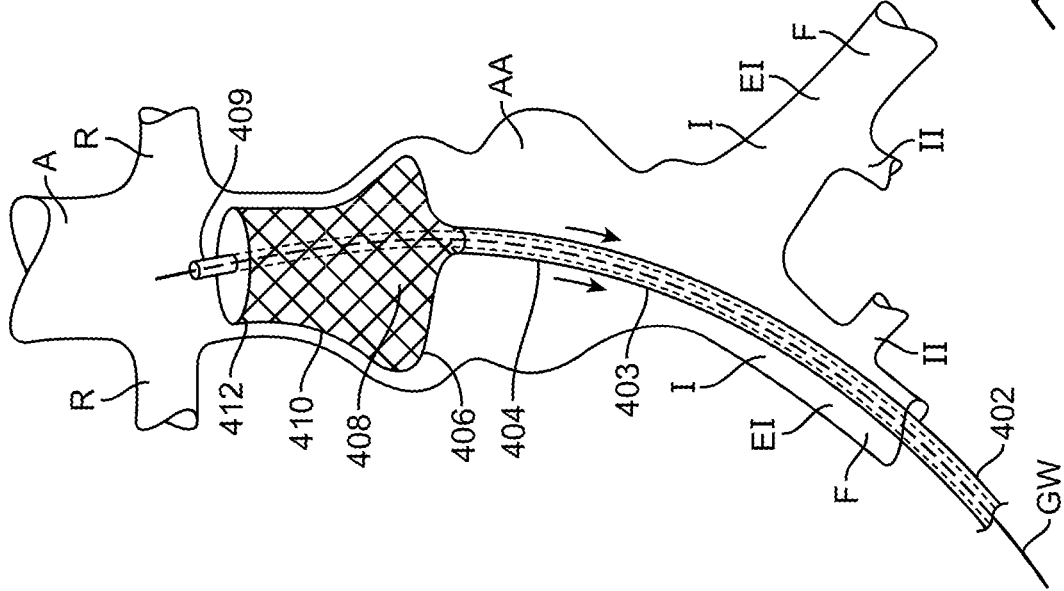

A delivery device such as a catheter 402 carrying the prosthesis can then be advanced over the guidewire GW so that the distal portion 404 of the delivery catheter 402 is positioned beyond the location of the aneurysm and preferably is upstream or superior to the proximal end (closest to the heart) of the aneurysm, as illustrated in FIG. 33C. Now referring to FIG. 33D, the delivery device may include an inner shaft 409 which carries the prosthesis 406, and an outer sheath 403 disposed over the prosthesis to constrain the prosthesis from expansion during delivery. The delivery device may have one or more radiopaque markers (not shown) or other indicators to facilitate visualization, alignment, and delivery of the prosthesis, or optional radiopaque markers or other indicators on the prosthesis itself may be used to help position the device. Once the delivery catheter is appropriately positioned relative to the aneurysm, the outer sheath 403 may be retracted proximally (toward the physician operator), or from a far end of the prosthesis to a near end of the prosthesis (with respect to the operator), to expose the personalized prosthesis 406 having a mesh 408 and polymer cover 410. When referring to the catheter, the term proximally refers to a position closest to the physician operating the catheter, and distal refers to a position furthest away from the physician operating the catheter. When referring to the aneurysm or the prosthesis, a proximal portion of the aneurysm or prosthesis is the portion closest to the heart (also referred to as upstream), and the distal portion of the aneurysm or prosthesis is furthest away from the heart (also referred to as downstream). The prosthesis 406 is a personalized prosthesis or PSG that has been manufactured to match the anatomy of the treatment site using the methods described herein. The prosthesis 406 may be any of the embodiments of personalized prostheses described herein. Retraction of the outer sheath 403 as indicated by the arrows in FIG. 33D removes the constraint from the prosthesis 406 thereby allowing the prosthesis to progressively self-expand into engagement with the walls of the aorta upstream of the aneurysm. As the outer sheath is retracted, an upstream or far end portion 412 of the prosthesis 406 radially expands outward into engagement with the aneurysm. The outer sheath 403 is further retracted as indicated by the arrows in FIG. 33E, until the entire prosthesis 406 is free of a constraint and thus the prosthesis 406 radially expands into engagement with the walls of the aneurysm and preferably above and below the aneurismal sac as well. Once the prosthesis has been delivered, the delivery catheter and guidewire may be removed from the patient leaving only the prosthesis 406 behind, as seen in FIG. 33F. Because the prosthesis 406 has been personalized to match the contours of the aneurysm, the prosthesis can self-expand to substantially fill the entire aneurismal sac and the prosthesis can engage the walls of the aneurysm over the entire treatment region. Further, as described herein, the prosthesis can be configured to self-adjust in response to any mismatches between its shape in the expanded configuration and the actual shape of the inner wall of the aneurysm, as well as self-orient to rotationally align its shape with the shape of the aneurysm.

Filling the entire aneurysm sac and having engagement of the prosthesis with the walls of substantially all of the aneurysm securely anchors the prosthesis in position, thereby preventing migration of the prosthesis and also ensuring good sealing between the prosthesis and the vessel. High conformity between the prosthesis and the walls of the aneurysm can prevent endoleaks and thus effectively exclude the aneurysm from blood flow, thereby alleviating pressure on the weakened walls of the aneurysm and preventing further dilation of the aneurysm. The personalized prosthesis can thus reinforce the aneurysm. Additionally, as shown in FIGS. 1G and 1H, some aneurysms may comprise mural thrombus formed on the walls of the aneurysm. Implanting a personalized prosthesis that matches the contours of the aneurysm helps to trap any mural thrombus between the prosthesis and the aneurismal wall, thereby preventing the mural thrombus from embolizing. Additionally, endothelial cells can cover the prosthesis and further facilitate anchoring of the device in position. Endothelialization generally begins about two weeks after implantation, and is substantially complete after approximately two months.

No new lumen is created in the embodiment of the prosthesis illustrated in FIGS. 33A-33F, and the blood can flow through a path that is substantially similar to its original path through the aneurysm, but while contacting the walls of the personalized prosthesis rather than the walls of the aneurysm. However, in some circumstances, it may be beneficial to create a new lumen for blood flow, as shown and described with reference to FIGS. 6A-6C. The new lumen may further prevent exertion of blood pressure against the walls of the aneurysm, or may restore natural blood flow or hemodynamics back to, or close to pre-aneurismal conditions.

In the embodiment of FIGS. 33A-33F a single prosthesis is delivered to the aneurysm.

However, in other embodiments, more than one prosthesis may be delivered. Delivering multiple prostheses can facilitate the delivery process since a single, low profile device may first be delivered, and additional prostheses may then delivered on top of one another, or axially spaced apart from one another in order to provide the desired coverage and support.

FIGS. 34A-34B illustrate the delivery of two personalized prostheses 1504 and 1506. The prostheses may be delivered in substantially the same manner as previously described above, one after the other. A first personalized prosthesis 1504 may be delivered to the aneurysm AA and allowed to expand into engagement with the wall 1502 of the lumen. A second personalized prosthesis 1506 may then be serially delivered after delivery of the first prosthesis, such that the second prosthesis sits inside the first prosthesis 1504. FIG. 34B illustrates a cross-section taken along the line B-B in FIG. 34A, and shows the two prostheses adjacent one another within the aneurysm. Such a configuration can provide greater support to the aneurysm and allows two lower profile prostheses to be delivered instead of a single higher profile device. Endothelialization of the prostheses can help to further anchor the prostheses into position. Multiple prostheses may be stacked inside one another as shown in FIGS. 34A-34B, and/or they be placed end to end to cover a longer treatment region.

Figure 35A:
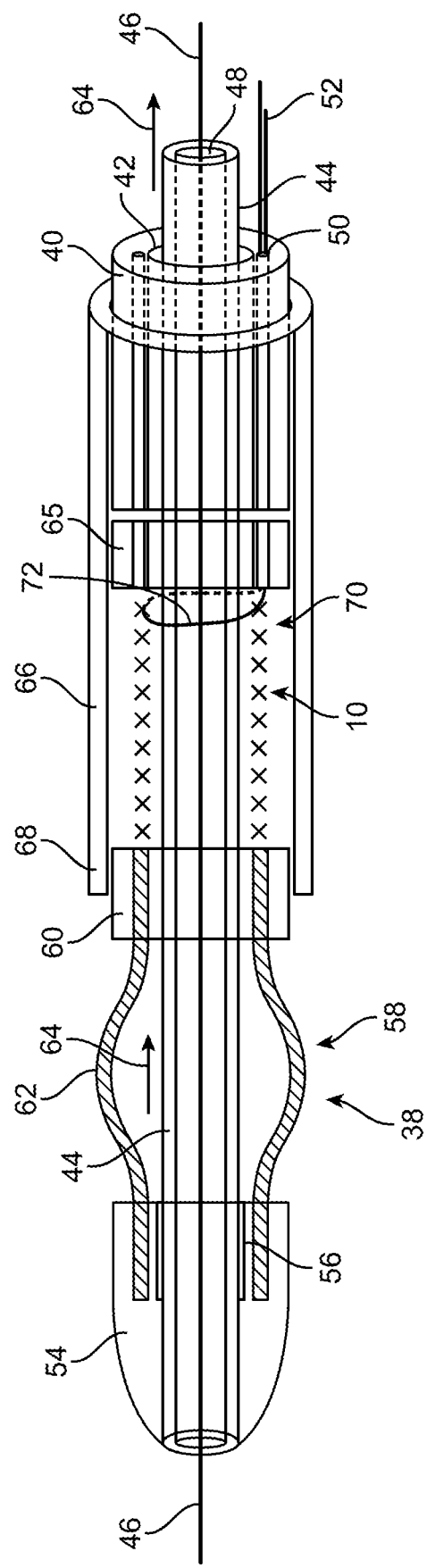
FIG. 35A illustrates the distal end of the delivery catheter system of this invention.

FIG. 35A shows the distal portion 38 of a delivery catheter system (DC) suitable for incorporation with embodiments. The system comprises a multilumen tube 40. The central lumen 42 provides for a passageway for the guidewire tube 44. A guidewire 46 traverses through the lumen 48 of the guidewire tube 44. Other lumens 50 of the multilumen tube 40 provide for passageway for the purse string pull wires 52. At the distal end of the DC, a nosecone 54 is attached to the guidewire tube 44 by means of the adhesive 56. The nosecone 54 allows an atraumatic movement of the DC in the blood vessel.

The distal portion 38 of the DC contains an expandable wire basket assembly 58. The wire basket assembly comprises two collars with a plurality of holes. Nosecone 54 serves as the distal collar, and collar 60 forms its counterpart at the proximal end. The guidewire tube 44 traverses freely through the central lumen of the collar 60. A plurality of wires 62, of material such as nitinol, is positioned between the two collars 54 and 60. The ends of the wires are disposed in the plurality of holes and secured by bonding or other methods known in the art. The nosecone 54 can be moved closer to the collar 60 by moving the guidewire tube 44 in a manner 64 in the proximal direction. The wires 62 can deform to create a basket-like structure, generally in a cross-section of a circle. The outside diameter of the wire basket (also referred to herein as a spline) can be varied by changing the distance between the two collars 54 and 60. The hoop strength of the spline structure is determined by the diameter and number of the wires 62. The maximum diameter of the deployed wire basket spline is determined by the length of the wires 62. The variable diameter spline 58 is used in the final apposition of the PSG in the AAA. It is also used to hold the PSG in position while removing the purse string filament from the PSG 10.

The spline structure may be a braided section of wires of appropriate diameter, length, and number so as to function as a deployable basket. Another way to achieve a basket like structure and function may be to have it constructed from a laser cut tube. The length, width, and thickness of the splines in the laser-cut structure can be optimized to the desired function.

Figure 36:
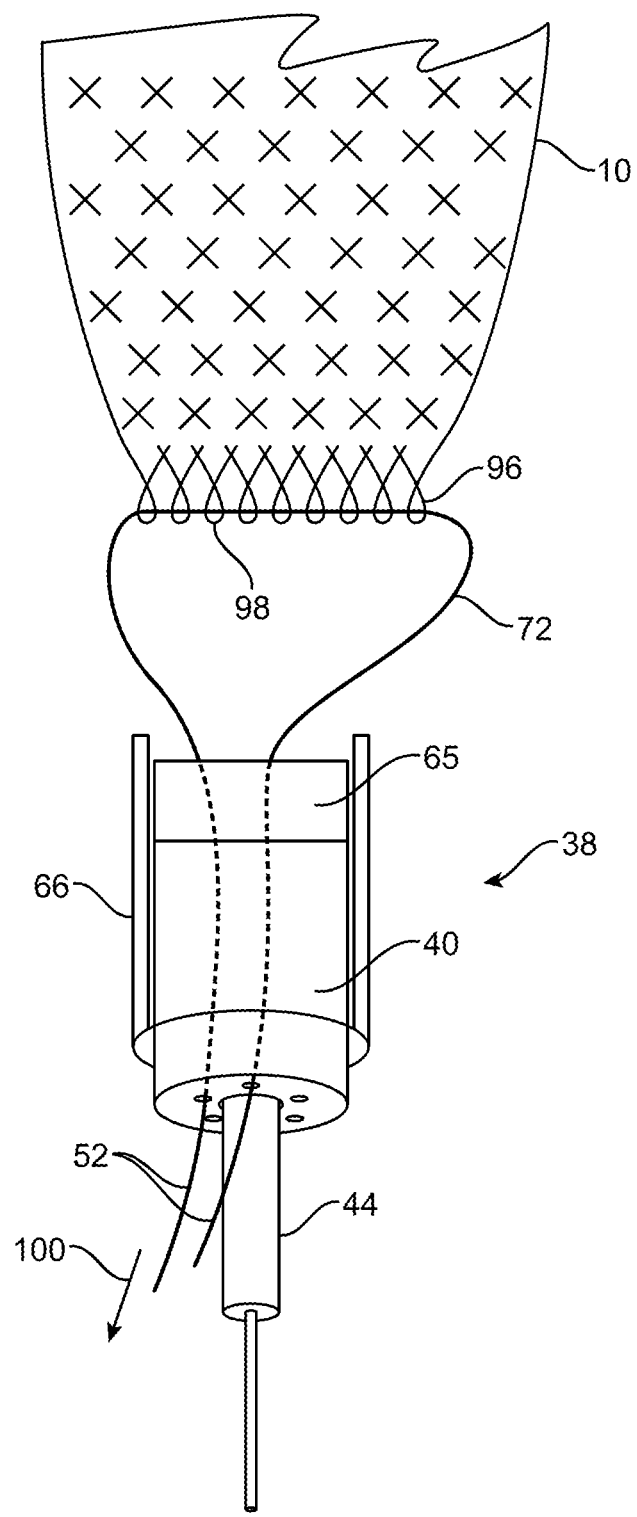
FIG. 36 shows the purse string looping of the proximal end of the personalized prosthesis using a single filament.

Still referring to FIG. 35A, the multilumen tube 40 terminates at its distal end at a collar 65 which has corresponding holes to match the lumens of the tube 40. The purpose of this collar 65 is to provide for a back stop for the PSG 10 during its deployment in the AAA. A slider tube or outer sheath 66 forms the outer part of the DC 38, and moves slidably over the multilumen tube 40. The distal end 68 of the slider tube 66 extends over the nosecone 54 creating an annular pocket 70 between the slider tube 66 and the guidewire tube 44. The spline 58 is contained in a collapsed configuration at the distal end of the pocket 70. The annular pocket 70 extends proximally between collars 60 and 65. The PSG 10, in its collapsed condition, is housed in this pocket 70. The proximal end of the PSG 10 constitutes loops 96 (shown in FIG. 36) of the wires 33 and 34. A purse string filament 72 is weaved through these loops 96 to capture the PSG 10. FIG. 36 shows a close up view of the purse string filament 72. The purse string filament traverses the length of the DC and resides in the lumen 50 of multilumen tube 40, forming a pair of filaments 52.

Figure 35B:
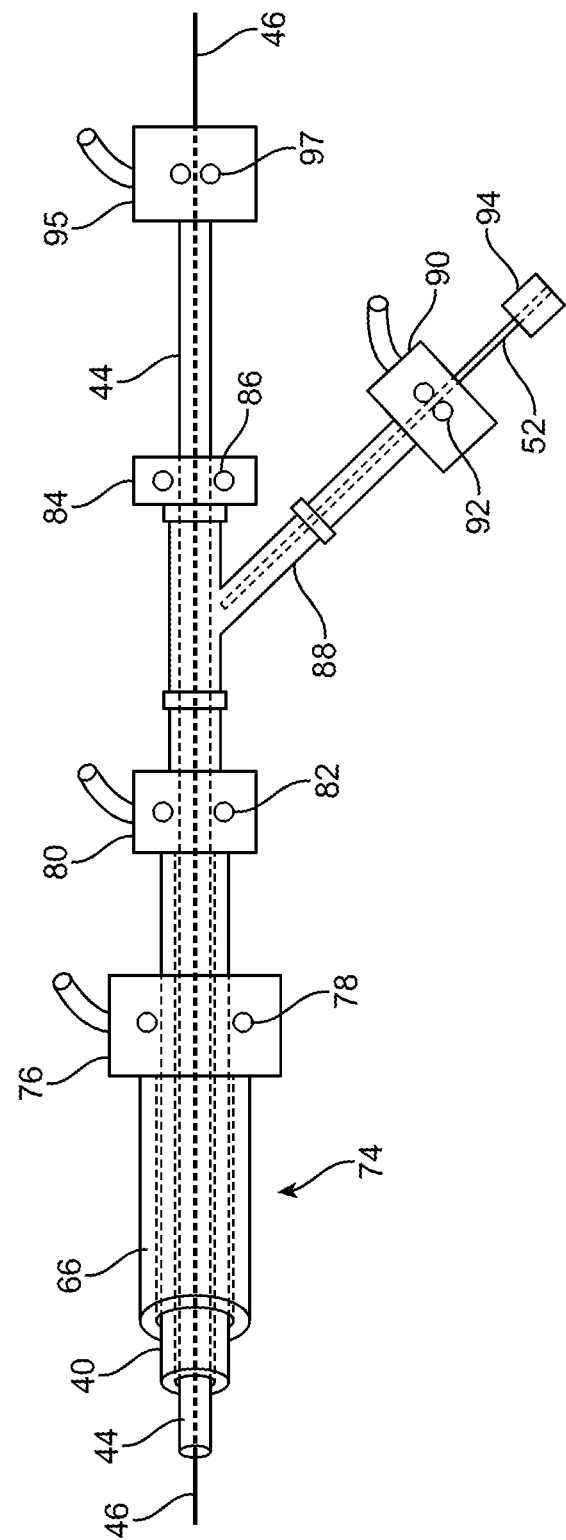
FIG. 35B illustrates the proximal end of the delivery catheter system that may be coupled to the distal end in FIG. 6A.

FIG. 35B shows the proximal portion 74 of the delivery catheter DC. Slider tube 66 terminates in a Tuohy Borst (TB) adapter 76. The multilumen tube 40 passes inside the slider tube 66 and passes through the TB adapter 76. The TB adapter provides a fluid seal 78 over tube 40 against a fluid leak from the body lumen to the outside. The tube 40 itself terminates at another TB adapter 80 which provides for a fluid-tight seal 82 around the guide wire tube 44 passing therethrough. The guidewire tube passes through a hemostatic valve splitter 84 which provides a fluid seal 86 against the guidewire tube 44. The hemostatic valve splitter 84 has a side arm 88 attached to yet another TB adapter 90 providing a fluid seal 92 against the purse string pull wire pair 52. The pull wire pair 52 is terminated in a plug 94 which allows the handling of the pull wires. The guidewire tube 44 terminates another TB adapter 95 which provides a fluid seal 97 against the guidewire 46.

Figure 35C:
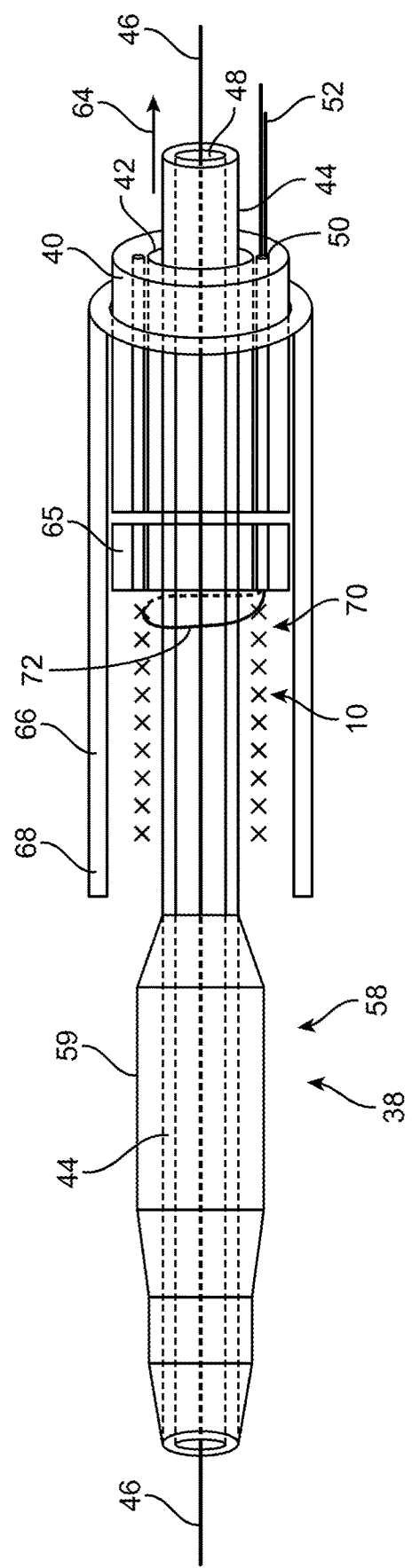
FIG. 35C illustrates the distal portion of an alternative embodiment of the delivery catheter system of FIG. 35A.

FIG. 35C shows the distal portion 38 of an alternative embodiment of the delivery catheter system (DC) of FIG. 35A. The DC of FIG. 35C is similar in many aspects to the DC of FIG. 35A, and comprises many of the same components as described with reference to FIG. 35A. However, instead of an expandable wire basket assembly or spline (58, FIG. 35A) coupled to the nosecone 54 and the collar 60, the distal portion 38 comprises an expandable balloon 59. The expandable balloon may comprise any expandable catheter balloon as known in the art, with suitable dimensions and material strength to form a firm apposition against the inner wall of the aneurysm when expanded. The expandable balloon may be used to hold the PSG in position while removing the purse string filament from the PSG 10, and/or during the final apposition of the PSG in the AAA. The delivery catheter system may further comprise an expansion lumen for expanding the balloon.

FIG. 36 shows the threading of the pull wire 72 (as shown in FIG. 35A) through the loops 96 at the proximal end of the PSG 10. As shown, the wire is threaded through the loops 96 to form a purse string 98 preferably extending circumferentially all the way around the proximal end of the PSG 10, then passing through one or two lumens of the collar 65 and the tube 40 becoming a pair 52. As the wire pair 52 is pulled proximally in a manner 100, the purse string tightens and collects the loops 96 in a compact bundle. This bundle can then be pulled proximally in to the slider tube 66. In this manner, the PSG 10 can be pulled inside the slider tube 66 in its entirety and it resides inside the slider 66 in a collapsed condition. This allows for multiple attempts of the deployment of the PSG 10 in the AAA. In the configuration shown in FIG. 36, only one pull wire is used to activate the reloading of the PSG 10 inside the slider tube 66. The pull wire 72 can be made of a metal, such as nitinol, or a non-metal, such as nylon. The pull wire 72 can also be made of a bio-degradable material.

Figure 37:
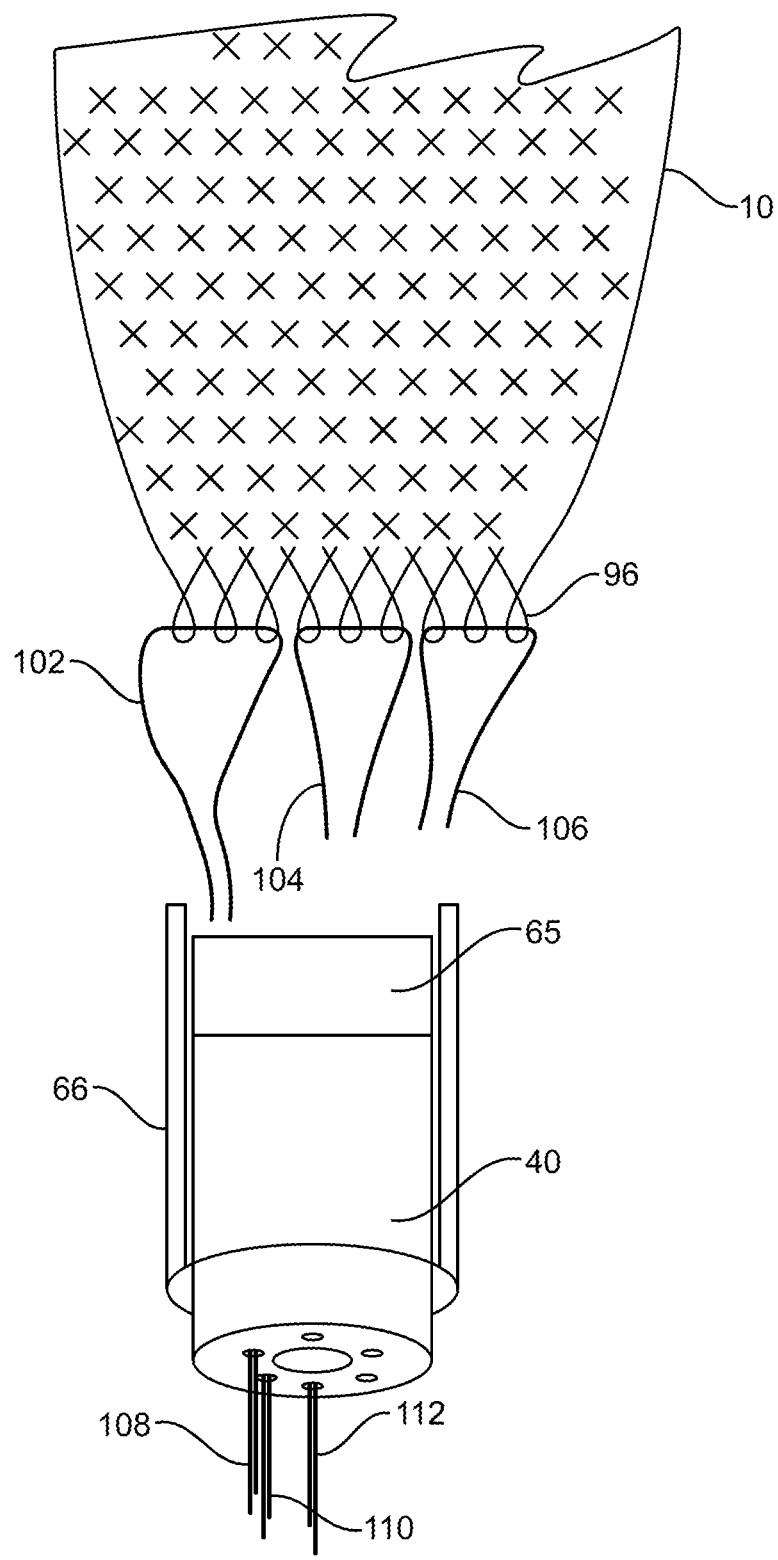
FIG. 37 illustrates shows the purse string looping of the proximal end of the personalized prosthesis using multiple filaments.

FIG. 37 shows a purse string pull wire mechanism employing a plurality of pull wires. Each pull wire may be threaded through a subset of the loops 96. For example, as shown in FIG. 37, pull wire 102 is threaded through few of the loops 96, and pull wires 104 and 106 are threaded through different sets of loops 96. These pull wires form their own pairs and can be fed through separate lumens of the tube 40. These pull wire pairs 108, 110, and 112 exit through the side port 88 at the proximal end of the delivery catheter terminating in their own individual plugs (plugs not shown). The retraction of the PSG 10 into the slider 66 is achieved by pulling the wire pairs proximally. The advantage of the multiple pull wires is that during removal of the pull wires, the wires encounter reduced friction by virtue of being engaged in fewer loops.

Figure 38:
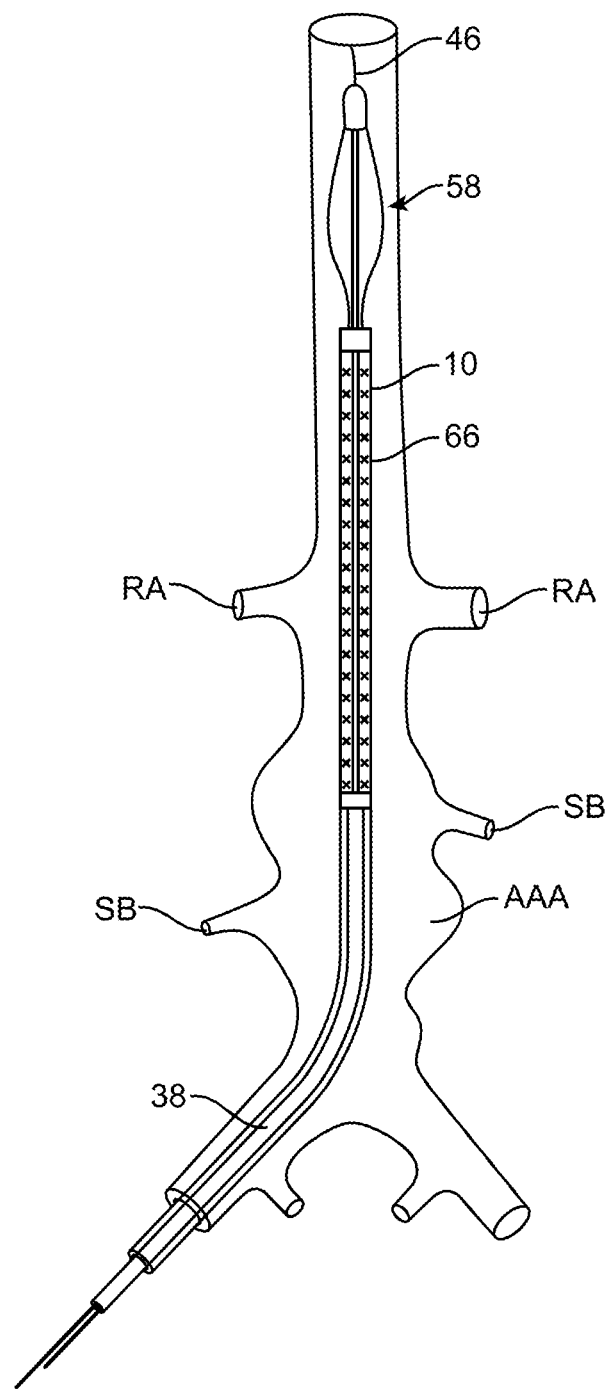
FIG. 38 shows the position of the delivery system in the aorta at a supra-renal location.

The method of deployment of a self-expanding, self-adjusting, and self-orienting PSG in the AAA is described next. As shown in FIG. 38, the distal portion 38 of delivery catheter (DC) is advanced over a guidewire 46 in a conventional manner from the femoral artery entrance to the site of the AAA. The DC is advanced until the spline basket 58 or an expandable balloon (not shown) is positioned in a suprarenal location. The PSG 10 is contained inside the slider tube 66 in a collapsed configuration. The delivery catheter may be advanced until the axial position of the prosthesis, along a longitudinal axis of the AAA, is slightly past the axial position of the target delivery region.

Figure 39:
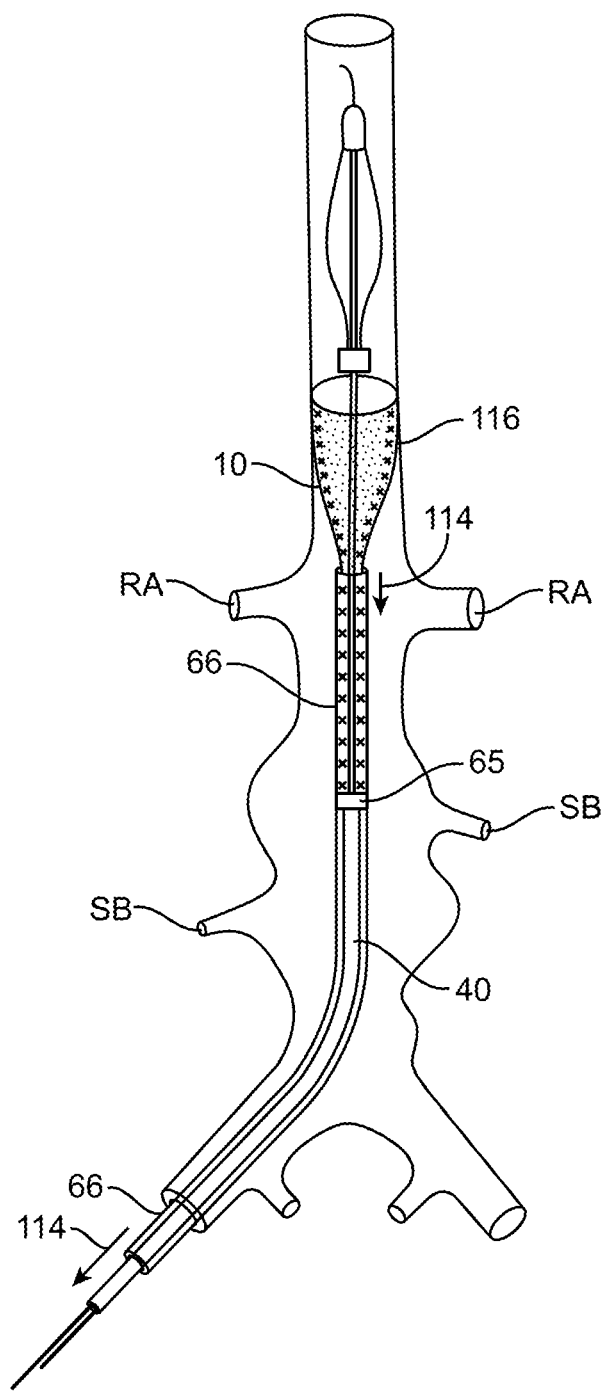
FIG. 39 illustrates the prosthesis partially deployed in the supra-renal space.

Now referring to FIG. 39, the slider tube 66 is moved proximally in a manner 114, from the far end towards the near end of the PSG, to allow the prosthesis to progressively self-expand. The proximal portion of the PSG 10 is held against collar 65 which serves a back stop. The distal or far end 116 of the PSG 10 is first released and it opens up in a self-deploying, self-adjusting manner as described herein. FIG. 39 thus shows the partial deployment of the PSG 10 in a suprarenal location at the site of the AAA.

Figure 40:
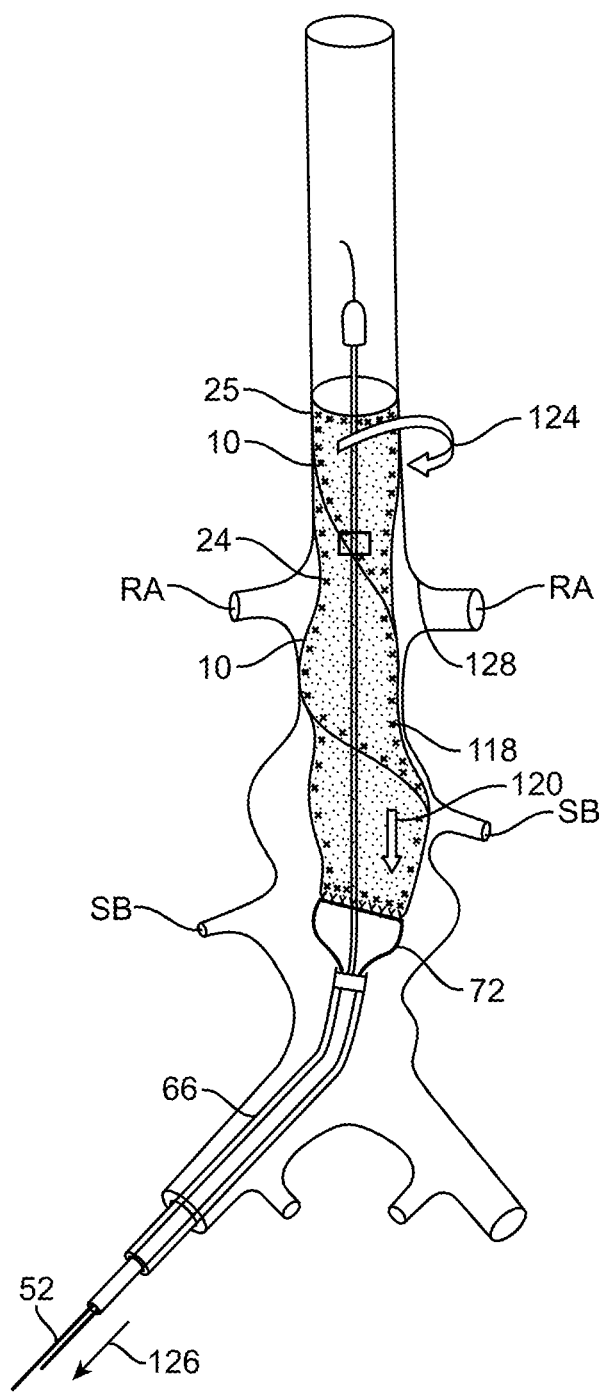
FIG. 40 shows the complete retraction of the slider allowing the prosthesis to reside in the suprarenal space.

FIG. 40 shows complete retraction of the slider tube 66 exposing the PSG 10 in the AAA space still in a suprarenal location, with the prosthesis positioned superior to its target delivery region. At this location, the shape of the exposed, self-expanded PSG 10 does not yet line up with the AAA, and the contours of the outer surface of the prosthesis do not axially and/or rotationally align with the contours of the inner wall of the AAA. Consequently, the internal shape of the AAA can place constrains on the PSG at some locations of mismatch between the PSG and the AAA. Constrains placed on the prosthesis by the shape of the target region of delivery can cause the prosthesis to remain in a collapsed or partially collapsed configuration at these locations. For example, at portion 118 of the body of the PSG, the tendency of the PSG to expand further is constrained by the inner wall of the AAA against which portion 118 is held. As described in further detail herein, the prosthesis in a collapsed or partially collapsed configuration comprises stored potential energy, urging the collapsed prosthesis to self-orient and self-adjust into a configuration that yields the lowest energy state.

To position and orient the PSG properly in the target delivery region, the prosthesis can be retracted slowly towards the target region, from a far end position to a near end position. The axial movement of the prosthesis towards the target region allows the prosthesis to self-orient by rotating about the longitudinal axis of the AAA into the proper orientation with respect to the AAA. For example, as illustrated in FIG. 40, the PSG 10 bundle is pulled slowly proximally in a manner 120 by pulling on the wire pair(s) 52 in a manner 126, towards the target region of delivery. As the PSG bundle moves linearly in the proximal direction along the axis of the vessel, the prosthesis bundle self-rotates in a manner 124 about the longitudinal axis of the AAA, due to factors described in further detail herein. The prosthesis can translate and self-rotate until the contours of the outer surface of the prosthesis are rotationally aligned with the contours of the inner walls of the AAA. It is important that the blood flow through the aorta not be blocked during the axial movement or retraction of the prosthesis. The incompletely deployed PSG, having pockets of mismatch between the PSG and the AAA, allows the blood to flow around the collapsed or partially collapsed portions.

The impetus for the self-rotation of the PSG comes from the fact there is potential energy stored in the collapsed PSG 10. The potential energy is made of two components. One portion is the radial compressional energy which is stored in the wire filaments 33 and 34 by virtue of their deformation as they are held in a constrained or collapsed configuration inside the slider tube 66. The second component, namely, the torsional or rotational potential energy is stored in the twisted structure of the PSG 10 bundle. This rotational potential energy is created by virtue of the fact that as the PSG 10 is being loaded inside the slider tube 66, the PSG 10 bundle is forced to rotate due to the direction of the wire twists, as described in further detail herein, such that the collapsed PSG bundle is stored in a twisted configuration. These two forms of potential energy are released during deployment of the PSG 10. PSG 10 finally takes a form of the lowest energy state, namely, a free state of deployed shape. However, in the situation when the PSG 10 is constrained in a suprarenal location, it is not yet able to release all the torsional (or rotational) potential energy. The torsional energy is released by self-rotation 124 of the PSG bundle. The tendency to self-rotate to a free shape encounters a friction between the surface 24 of the PSG 10 and the inner wall 128 of the blood flow lumen. When the PSG 10 is in a stationary state, the friction is termed 'static' friction and may be sufficiently high to prevent the PSG from self-rotating. However, as the PSG 10 is put into a slight axial motion 120, the surfaces 24 and 128 now are in 'kinetic' friction, which is much lower than the static friction. Therefore, the rotational forces are able to overcome the kinetic friction, resulting in a freer self-rotation of the PSG to achieve rotational alignment with the contours of the target delivery region.

The direction of the self-rotational motion is determined, in part, by the direction of the wire twists comprising the PSG 10. Referring to FIG. 12G, a PSG composed of substantially all the twists 35 in the clockwise (cw) direction will have a tendency to rotate in a clockwise direction as viewed from the inferior to superior direction. Conversely, as shown in FIG. 12H, a PSG composed of substantially all the twists 35 in the counterclockwise (ccw) direction will have a tendency to rotate in a counterclockwise direction as viewed from the inferior to superior direction. A PSG 10 composed of random twist patterns 35 will not have a preferential direction of rotation. Therefore, a prosthesis may be biased to twist in a pre-determined direction upon self-orientation, by constructing the prosthesis using a wire frame having a specific pattern or direction of wire twists, such that the direction of rotational motion of the prosthesis during its self-orientation in deployment can be controlled. The prosthesis can be constructed to rotate in one direction during self-orientation, or the prosthesis can be constructed to have a plurality of regions each configured to have its own rotational bias during self-orientation. For example, a first region of the prosthesis can be biased to twist in a first direction, while a second region can be biased to twist in a second direction opposite the first direction.

The tendency for a favored direction of rotation based on the direction of the wire twists 35 (cw or ccw) can be minutely explained in the following manner. As the PSG 10 bundle moves proximally in a manner 120, the interface between the twisted wire surface and lumen surface occurs at an angle whose direction is determined by the direction of the twist. During motion 120, in relative terms, the lumen surface is moving superiorly against wire twist(s). This motion imparts a sideways force on the wire of the twist as it presents itself at an angle (of the twist) to the luminal surface. This sideways force has a torsional vector component which results in a rotational movement of the PSG bundle 10. The same force vector comes in play when the PSG 10 is being loaded into slider 66 by pulling the PSG 10 in a linear fashion proximally.

Thus, as the PSG bundle 10 is being moved proximally along the axis of the lumen during deployment, the bundle also self-rotates, wherein the direction of the rotation is determined by the twist direction (cw or ccw) of the wire frame of the PSG. The intended result is the release of the torsional potential energy. The preferred direction of the rotation can be predetermined by examining the anatomy of the AAA, and the tendency of the lay and angle of the PSG in the collapsed or partially collapsed configuration as it is positioned in the location suprarenal to the AAA. This angle of the collapsed or partially collapsed PSG can help guide the direction of the required twist pattern with which the PSG is fabricated.

The twist pattern 35 can thus be configured to facilitate the self-rotation 124 of the PSG bundle during the deployment of the PSG, such that its torsional potential energy is released in the most efficient manner. The linear or axial motion 120 of the PSG in the inferior direction puts the bundle in a kinetic friction state allowing for an easier self-rotation of the PSG bundle.

The PSG 10 can be constructed in a manner such that its superior end is in line with an anatomical feature, such as the edge of a vertebra, when deployed in its target axial position. The superior edge of the PSG 10 may be disposed with radio-opaque markers 25 which are visible under fluoro x-ray guidance. Continuing with the movement of the PSG 10 inferiorly, the PSG 10 comes to a position where its superior end matches the target anatomical location (such as the edge of a vertebra) when viewed under fluoro guidance. At this point, substantially all the stored potential energy is released and the PSG 10 can take a self-oriented, rotationally conformal position against the AAA. In the rotationally aligned position, not only do the contours of the outer surface of the PSG align with the contours of the inner wall of the aneurysm, but also the lateral apertures or fenestrations 18 and 20 of the PSG align with the corresponding ostia of the renal arteries RA. As described herein, the locations of the RA may be determined based on one or more images of the aneurysm and the prosthesis may be manufactured to comprise lateral apertures configured to align with the ostia of the RA when implanted. Therefore, the self-orientation of the prosthesis to rotationally align with the contours of the aneurysm automatically results in the alignment of the lateral apertures with their corresponding ostia. In this way, the self-orienting prosthesis not only ensures complete conformation with the geometry of the aneurysm, but also facilitates the alignment of one or more lateral apertures of the prosthesis with their intended targets. By contrast, a conventional stent graft with no self-orienting capability or particular rotational orientation would require manual orientation to align the later apertures with their corresponding ostia.

Thus, the PSG is aided in self-aligning or self-orienting itself rotationally within the AAA pocket by (a) twist pattern (direction) of the wires of PSG 10 and (b) axial or linear motion of the PSG which puts the PSG in a kinetic friction mode, facilitating the rotational motion of the PSG. Helped by the aforementioned factors, the PSG can come to its lowest energy state by aligning itself conformally against the AAA.

While the PSG is herein described to be manually pulled or retracted axially along the lumen and towards the target deployment region, the axial movement of the PSG may also comprise a self-translation component. As described herein, the PSG self-orients rotationally as it is being retracted towards the intended final position, in order to reach the lowest energy state wherein the contours of the outer surface of the prosthesis substantially match the contours of the target region. As the PSG moves closer to its target axial position, the tendency of the PSG to rotate into its final orientation can cause axial self-translation of the PSG into the proper axial position, driven by the self-rotation of the PSG. Therefore, the PSG is not only translated manually, but in at least some stages of its placement into its target axial position, the PSG may self-translate axially along the lumen such that the contours of the outer surface of the prosthesis axially align with the contours of the target region.

Once the PSG reaches its proper axial position and rotational orientation with respect to the AAA, the prosthesis can self-adjust in one or more locations along its body to accommodate the exact shape and dimensions of the AAA, as described herein. For example, the PSG can be manufactured to be slightly oversized with respect to the shape of the AAA as determined from a CT scan, and constructed with self-adjustable wire frame construction as described herein (e.g., 41 or 31 configurations with 3-2-2-2 or 3-2-2 twist loop configurations). When the PSG is placed in the proper axial position and rotational orientation, the twist loops of the wire frame can open up appropriately to adjust the shape and dimensions of the frame at any locations of mismatch between the prosthesis and the AAA, to match the internal geometry of the AAA. For example, at locations of mismatch wherein the diameter of the PSG in its fully-expanded configuration is larger than the diameter of the AAA, the PSG may self-adjust to reduce its diameter to match the diameter of the AAA.

Figure 41:
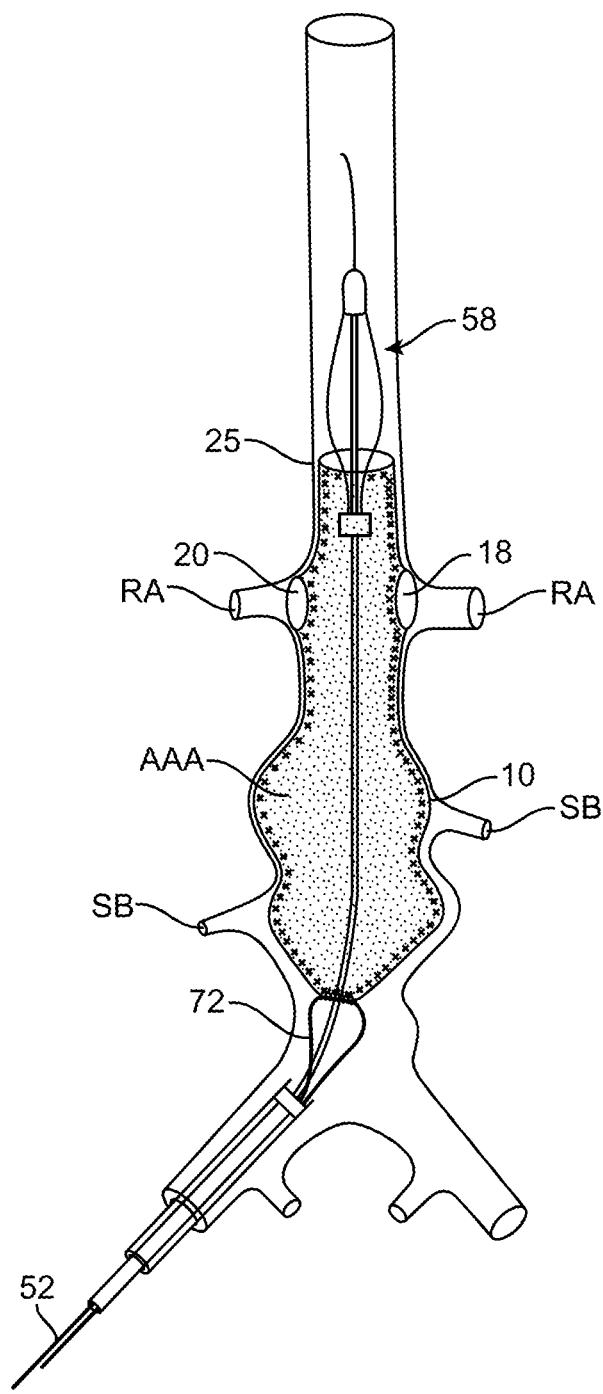
FIG. 41 shows the conformal deployment of the prosthesis in the aneurysm space.

FIG. 41 shows the PSG 10 deployed in the AAA space. The proximal end of the PSG is still held together by the purse string 72. The spline 58 (or the expandable balloon) remains in place supra-renally. If it is determined that another attempt is needed in placing the PSG, the PSG can be retracted back inside the slider tube 66 in a manner described in FIG. 40. Another attempt can then be made, as described above, to deploy the PSG 10 in the AAA. The goodness of the PSG placement in the AAA can be determined by comparing the before and after fluoro images of the AAA space. The fenestrations 18 and 20 of the PSG should be aligned with the ostia of the renal arteries RA. In addition, the flow of the contrast fluid can be observed, it should show that the contrast flow into the side branches SB is absent or largely diminished, unless the PSG comprises additional lateral apertures to accommodate the side branches.

Optionally, the PSG may be rotated manually about its longitudinal axis at any stage of the deployment, to facilitate the self-orientation of the PSG into its target rotational orientation and to ensure that the PSG is finally oriented into its proper rotational orientation.

Figure 42:
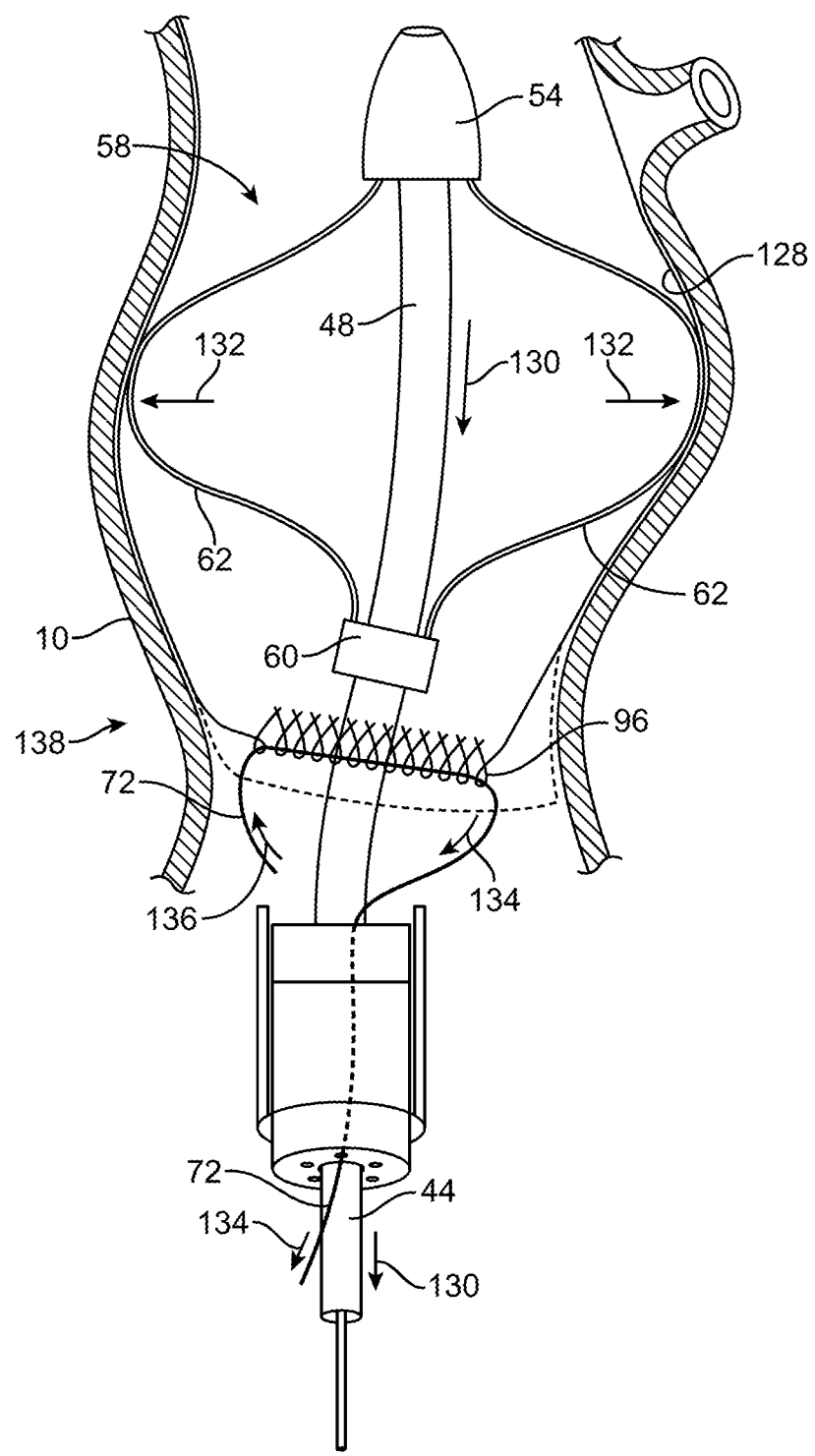
FIG. 42 shows the removal of the purse string filament releasing the proximal end of the prosthesis.

Once it is deemed that the PSG has been correctly implanted in the AAA, the pull wire string is preferably removed using the following method. Referring to FIG. 42, the spline assembly 58 is moved proximally such that the spline wires 62 are slightly superior to the proximal end of the PSG 10. The spline is deployed by pulling the nose cone 54 towards the collar 60 by moving the guidewire tube 44 in a manner 130. As the nosecone 54 moves closer to the collar 60, the wires 62 of the spline expand outwards in a manner 132 to form a basket. The basket continues to be expanded until the wire elements 62 are firmly against the inner surface 128 of the PSG 10. This position of the distended spline holds the PSG 10 in place to guard against any movement as the purse string wire is withdrawn. One of the filaments of pair 52 is pulled proximally in a manner 134. This causes the other end of the wire to move in a manner 136. The wire pulling motion is continued until the wires clears through the wire loops 96. Once the wire 72 is removed from the PSG 10, the proximal end 138 is released and the PSG self-deploys in its intended place in the AAA Similarly, for the case where multiple pull wires used (as shown in FIG. 37), each wire can be pulled out in the same manner as described above for the single wire pull string.

Figure 43:
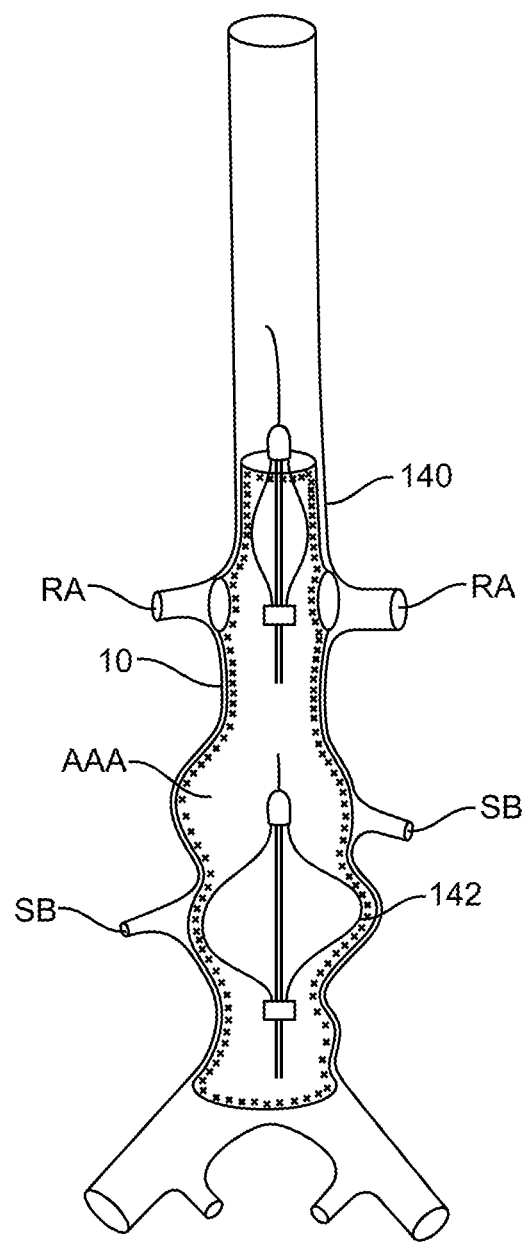
FIG. 43 illustrates use of the spline to achieve the enhanced apposition of the prosthesis against the blood vessel wall.

The final apposition of the PSG in the AAA is achieved by use of the spline assembly as shown in FIG. 43. The spline wires are deployed (as described above) from superior to the inferior locations. By way of example, the spline is deployed in the superior location 140 to further apposition or "tack" the PSG against the wall of the AAA. Similarly, the spline is shown deployed in an inferior location 142. The spline can be deployed in as many locations in any order as deemed necessary. The use of the spline for this purpose is advantageous as the open structure of the spline allows the flow of blood therethrough during the apposition process.

In embodiments of the delivery catheter system comprising an expandable balloon assembly (59, FIG. 35C) in the place of the wire basket or spline assembly 58, the expandable balloon may be used to facilitate the removal of the pull wire strings and the final apposition of the PSG in the AAA. The expandable balloon may be expanded to firmly engage the inner surface of the PSG while the pull wire strings are removed, thereby preventing axial movement or dislodging of the PSG from the target site. The expandable balloon may also be expanded at one or more locations along the PSG to tack the PSG against the wall of the AAA.

Finally, the delivery catheter is removed from the patient and the entry site at the femoral artery is sealed in a conventional manner. The PSG 10 is now implanted in the AAA as shown in FIG. 3B.

In any of the embodiments described herein, the filament may be any combination of wires having any cross-section such as round, square, rectangular, etc. and the size of the wire may be adjusted in order to various properties of the prosthesis such as its profile in the collapsed configuration, its stiffness and strength, and other properties. In preferred embodiments, a round nitinol wire is used having a diameter of 0.005 inches to 0.008 inches. Exemplary wire diameters of 0.005 inches, 0.0055 inches, 0.006. 0.0065, 0.007, 0.008 inches may be used.

Additionally, any of the prostheses may carry a therapeutic agent such as an antithrombotic agent, antibiotic, etc. for localized and controlled elution at the treatment site. One of skill in the art will also appreciate that the prosthesis described herein preferably has a mesh with a polymer or fabric cover disposed thereover, but the prosthesis could be a mesh only (without the membrane) to support the damaged or diseased tissue, or the prosthesis could be the polymer or fabric cover only. Thus, the fabrication methods and delivery methods described herein apply to either embodiment of prosthesis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for deploying a prosthesis personalized for a patient in a bodily lumen of the patient, the method comprising:
   providing a delivery catheter carrying the prosthesis, the prosthesis disposed in a collapsed and rotationally twisted configuration, and
   wherein the prosthesis is formed from a mesh comprising a plurality of filaments overlapping one another to form a repeating pattern of a first number of overlaps followed by a second number of overlaps different than the first number of overlaps;
   advancing the prosthesis in the collapsed and rotationally twisted configuration through the bodily lumen so the prosthesis is disposed at least partially upstream of a target region in the bodily lumen, the target region comprising a blood vessel;
   fully retracting a slider tube proximally away from the prosthesis to remove a constraint therefrom;
   allowing the prosthesis to progressively and radially self-expand from the collapsed and rotationally twisted configuration to an expanded configuration, wherein contours of the prosthesis are misaligned axially and rotationally with contours of the target region so that the prosthesis is at least partially constrained from further self-expansion;
   axially moving the prosthesis toward the target region thereby untwisting and rotating the prosthesis about a longitudinal axis of the prosthesis; and
   rotationally aligning and rotationally self-orienting the contours of the prosthesis with the contours of the target region.

2. The method of claim 1, wherein allowing the prosthesis to progressively self-expand comprises self-expanding from a far end portion to a near end portion of the prosthesis.

3. The method of claim 2, wherein the far end portion is further from an operator of the prosthesis than the near end portion.

4. The method of claim 1, wherein moving the prosthesis toward the target region concurrently removes a constraint from the prosthesis allowing the prosthesis to further self-expand, the constraint provided by the target region.

5. The method of claim 1, wherein self-orienting comprises urging the prosthesis to self-orient with the target region due to mismatching between the contours of the prosthesis and the contours of the target region.

6. The method of claim 5, wherein release of potential energy from the mismatching into a lower energy state urges the prosthesis to self-orient and conform with the target region.

7. The method of claim 1, wherein the target region comprises an aneurysm in the blood vessel.

8. The method of claim 7, wherein a far end portion of the prosthesis is closer to a heart of the patient than a near end portion of the prosthesis.

9. The method of claim 1, further comprising visualizing the prosthesis as the prosthesis is advanced or allowed to progressively self-expand.

10. The method of claim 1, wherein the prosthesis further comprises a polymeric coating covering the mesh.

11. The method of claim 1, wherein the prosthesis has a central lumen for fluid flow therethrough.

12. The method of claim 1, wherein rotationally self-orienting and rotationally aligning comprises aligning one or more ostia in the bodily lumen of the target region with one or more lateral apertures in the prosthesis that are sized to match the one or more ostia, and wherein the a location of the one or more lateral apertures is based on one or more images of the target region.

13. The method of claim 1, further comprising tacking the prosthesis into the target region with an expandable member.

14. The method of claim 1, wherein the repeating pattern forms a directional pattern on an outer surface of the prosthesis, and wherein during the self-expansion, the prosthesis rotationally untwists from the rotationally twisted configuration in a direction of the directional pattern.

15. The method of claim 1, wherein the contours of the prosthesis comprise a plurality of convex and concave regions, and wherein the contours of the target region comprise a plurality of convex and concave regions.

* * * * *